US008343753B2

(12) United States Patent  (10) Patent No.: US 8,343,753 B2
Chilton et al.  (45) Date of Patent: Jan. 1, 2013

(54) COMPOSITIONS, METHODS, AND KITS FOR POLYUNSATURATED FATTY ACIDS FROM MICROALGAE

(75) Inventors: Floyd Chilton, Winston Salem, NC (US); Fan Lu, Clemmons, NC (US)

(73) Assignee: Wake Forest University School of Medicine, Winston-Salem, NC (US)

( * ) Notice: Subject to any disclaimer, the term of this patent is extended or adjusted under 35 U.S.C. 154(b) by 665 days.

(21) Appl. No.: 12/436,542

(22) Filed: May 6, 2009

(65) Prior Publication Data

US 2010/0099765 A1 Apr. 22, 2010

Related U.S. Application Data

(63) Continuation-in-part of application No. 12/260,134, filed on Oct. 29, 2008, now abandoned, and a continuation-in-part of application No. PCT/US2008/081498, filed on Oct. 29, 2008.

(60) Provisional application No. 61/001,482, filed on Nov. 1, 2007.

(51) Int. Cl.
  *C12N 1/12* (2006.01)
(52) U.S. Cl. .................................... 435/257.1
(58) Field of Classification Search .............. 435/257.1
  See application file for complete search history.

(56) References Cited

U.S. PATENT DOCUMENTS

| 4,154,863 | A | 5/1979 | Kahn et al. |
| 4,309,415 | A | 1/1982 | Horrobin |
| 4,386,072 | A | 5/1983 | Horrobin et al. |
| 4,444,755 | A | 4/1984 | Horrobin |
| 4,560,514 | A | 12/1985 | Samuelsson et al. |
| 4,576,758 | A | 3/1986 | Morris |
| 4,666,701 | A | 5/1987 | Horrobin et al. |
| 4,758,592 | A | 7/1988 | Horrobin et al. |
| 4,868,212 | A | 9/1989 | Horrobin |
| 4,888,326 | A | 12/1989 | Horrobin |
| 4,918,104 | A | 4/1990 | Weiss et al. |
| 4,954,638 | A | 9/1990 | Young et al. |
| 4,965,075 | A | 10/1990 | Horrobin et al. |
| 4,977,187 | A | 12/1990 | Horrobin |
| 5,059,622 | A | 10/1991 | Sears |
| 5,069,903 | A | 12/1991 | Stitt |
| 5,073,561 | A | 12/1991 | Coughenour et al. |
| 5,116,624 | A | 5/1992 | Horrobin et al. |
| 5,116,871 | A | 5/1992 | Horrobin et al. |
| 5,141,958 | A | 8/1992 | Crozier-Willi et al. |
| 5,158,975 | A | 10/1992 | Guichardant et al. |
| 5,178,873 | A | 1/1993 | Horrobin et al. |
| 5,223,285 | A | 6/1993 | DeMichele et al. |
| 5,229,146 | A | 7/1993 | Tanaka |
| 5,244,921 | A | 9/1993 | Kyle et al. |
| 5,318,991 | A | 6/1994 | Horrobin et al. |
| 5,324,658 | A | 6/1994 | Cox et al. |
| 5,328,691 | A | 7/1994 | Horrobin et al. |
| 5,336,469 | A | 8/1994 | Tobiki et al. |
| 5,338,673 | A | 8/1994 | Thenepenier et al. |
| 5,352,700 | A | 10/1994 | Frithz et al. |
| 5,380,757 | A | 1/1995 | Horrobin |
| 5,397,591 | A | 3/1995 | Kyle et al. |
| 5,407,957 | A | 4/1995 | Kyle et al. |
| 5,411,988 | A | 5/1995 | Bockow et al. |
| 5,422,371 | A | 6/1995 | Liao et al. |
| 5,430,066 | A | 7/1995 | Cook et al. |
| 5,434,183 | A | 7/1995 | Larsson-Backström |
| 5,502,077 | A | 3/1996 | Breivik et al. |
| 5,508,307 | A | 4/1996 | Horrobin et al. |
| 5,516,800 | A | 5/1996 | Horrobin |
| 5,516,801 | A | 5/1996 | Horrobin et al. |
| 5,550,156 | A | 8/1996 | Kyle |
| 5,562,913 | A | 10/1996 | Horrobin |
| 5,567,732 | A | 10/1996 | Kyle et al. |
| 5,580,556 | A | 12/1996 | Horrobin |
| 5,589,508 | A | 12/1996 | Schlotzer et al. |
| 5,618,558 | A | 4/1997 | Horrobin et al. |
| 5,660,842 | A | 8/1997 | Petschow |
| 5,663,202 | A | 9/1997 | Horrobin et al. |
| 5,670,540 | A | 9/1997 | Horrobin et al. |
| 5,683,898 | A | 11/1997 | Yazawa et al. |
| 5,731,346 | A | 3/1998 | Egberg et al. |
| 5,734,034 | A | 3/1998 | Jayasena et al. |
| 5,747,533 | A | 5/1998 | Egberg et al. |
| 5,792,795 | A | 8/1998 | Buser et al. |
| 5,827,885 | A | 10/1998 | Cook et al. |
| 5,837,731 | A | 11/1998 | Vaddadi |
| 5,840,757 | A | 11/1998 | Dutot |
| 5,843,919 | A | 12/1998 | Burger |

(Continued)

FOREIGN PATENT DOCUMENTS

EP 0598365 A1 5/1994

(Continued)

OTHER PUBLICATIONS

International Bureau's International Preliminary Report on Patentability for PCT/US2008/081498.
Apt et al., Commercial Developments in Microalgal Biotechnology, J. Phycol. 35, pp. 215-226 (1999).
Bajpai et al., Eicosapentaenoic acid (EPA) production from microorganisms: a review, Journal of Biotechnology 30, pp. 161-183 (1993).
Bartual et al., Effect of irradiance on growth, photosynthesis, pigment content and nutrient consumption in dense cultures of *Rhodomonas salina* (Wislouch) (Cryptophyceae), Ciencias Marinas 28(4), pp. 381-392 (2002).

(Continued)

Primary Examiner — Jon P Weber
Assistant Examiner — Thane Underdahl
(74) Attorney, Agent, or Firm — Dann, Dorfman, Herrell & Skillman; Kathleen D. Rigaut

(57) ABSTRACT

The present invention provides compositions, methods, and kits comprising PUFAs produced by microalgae, in particular omega-3 and/or omega-6 fatty acids produced by members of the genus *Rhodomonas*, in particular *Rhodomonas salina*. The invention also provides compositions, methods, and kits comprising the PUFAs for the prophylactic and/or therapeutic treatment of a disease or condition, in particular a cardiovascular and/or inflammatory disease or condition.

9 Claims, 40 Drawing Sheets

U.S. PATENT DOCUMENTS

| | | |
|---|---|---|
| 5,855,917 A | 1/1999 | Cook et al. |
| 5,866,703 A | 2/1999 | Horrobin et al. |
| 5,888,541 A | 3/1999 | Horrobin et al. |
| 5,908,622 A | 6/1999 | Barclay |
| 5,914,347 A | 6/1999 | Grinda |
| 5,948,818 A | 9/1999 | Buser et al. |
| 5,993,221 A | 11/1999 | Bistrian |
| 6,107,334 A | 8/2000 | Chilton |
| 6,117,905 A | 9/2000 | Higashiyama et al. |
| 6,140,304 A | 10/2000 | Sears |
| 6,150,411 A | 11/2000 | Stordy |
| 6,184,251 B1 | 2/2001 | Stordy et al. |
| 6,255,505 B1 | 7/2001 | Bijl et al. |
| 6,277,417 B1 | 8/2001 | Anderson |
| 6,277,435 B1 | 8/2001 | Lacombe et al. |
| 6,297,280 B1 | 10/2001 | Ishihara et al. |
| 6,331,568 B1 | 12/2001 | Horrobin |
| 6,340,485 B1 | 1/2002 | Coupland et al. |
| 6,340,491 B1 | 1/2002 | Cain et al. |
| 6,340,705 B1 | 1/2002 | Obukowicz et al. |
| 6,344,482 B1 | 2/2002 | Stoll et al. |
| 6,407,075 B1 | 6/2002 | Scott et al. |
| 6,417,233 B1 | 7/2002 | Sears et al. |
| 6,479,544 B1 | 11/2002 | Horrobin |
| 6,551,596 B2 | 4/2003 | Kralovec |
| 6,576,666 B2 | 6/2003 | Hermelin et al. |
| 6,596,766 B1 | 7/2003 | Igarashi et al. |
| 6,599,939 B2 | 7/2003 | Wang et al. |
| 6,624,195 B2 | 9/2003 | Horrobin |
| 6,630,157 B1 | 10/2003 | Horrobin et al. |
| 6,656,969 B2 | 12/2003 | Young |
| 6,667,064 B2 | 12/2003 | Surette |
| 6,737,078 B1 | 5/2004 | Kelley |
| 6,812,009 B2 | 11/2004 | Gladue et al. |
| 7,001,610 B2 | 2/2006 | Stewart |
| 7,138,431 B1 | 11/2006 | Chilton |
| 7,157,254 B1 | 1/2007 | Akimoto et al. |
| 7,163,960 B2 | 1/2007 | Ursin et al. |
| 7,182,971 B2 | 2/2007 | Takase et al. |
| 7,195,914 B2 | 3/2007 | Surette |
| 7,199,112 B2 | 4/2007 | Llewellyn |
| 7,208,180 B2 | 4/2007 | Kiliaan et al. |
| 7,226,916 B1 | 6/2007 | Kiliaan et al. |
| 7,351,558 B2 | 4/2008 | Ruecker et al. |
| 2001/0025114 A1 | 9/2001 | Bijl et al. |
| 2001/0047036 A1 | 11/2001 | Vanderhoof et al. |
| 2002/0044968 A1 | 4/2002 | Van Lengerich |
| 2002/0146400 A1 | 10/2002 | Cincotta |
| 2002/0173450 A1 | 11/2002 | Chacon |
| 2003/0032674 A1 | 2/2003 | Hwang |
| 2003/0060509 A1 | 3/2003 | Elswyk |
| 2003/0152983 A1 | 8/2003 | Napier et al. |
| 2003/0166723 A1 | 9/2003 | Nakajima et al. |
| 2003/0175403 A1 | 9/2003 | Gurin |
| 2003/0203004 A1 | 10/2003 | Kelm et al. |
| 2003/0215465 A1 | 11/2003 | Cain et al. |
| 2004/0009208 A1 | 1/2004 | Edson et al. |
| 2004/0013788 A1 | 1/2004 | Seki et al. |
| 2004/0048919 A1 | 3/2004 | Dreon et al. |
| 2004/0048927 A1 | 3/2004 | Horrobin |
| 2004/0071825 A1 | 4/2004 | Lockwood |
| 2004/0092590 A1 | 5/2004 | Arterburn et al. |
| 2004/0106584 A1 | 6/2004 | Arterburn et al. |
| 2004/0109881 A1 | 6/2004 | Bertholet et al. |
| 2004/0132819 A1 | 7/2004 | Auestad et al. |
| 2004/0151757 A1 | 8/2004 | Heirler |
| 2004/0162349 A1 | 8/2004 | Shibuya |
| 2004/0191294 A1 | 9/2004 | Ramaprasad et al. |
| 2004/0208939 A1 | 10/2004 | Sears et al. |
| 2004/0235948 A1 | 11/2004 | Oelze et al. |
| 2004/0241286 A1 | 12/2004 | Markwell et al. |
| 2004/0266874 A1 | 12/2004 | Akimoto et al. |
| 2005/0009779 A1 | 1/2005 | Kiliaan et al. |
| 2005/0027004 A1 | 2/2005 | Kyle et al. |
| 2005/0032757 A1 | 2/2005 | Cho |
| 2005/0032892 A1 | 2/2005 | Kelm et al. |
| 2005/0037065 A1 | 2/2005 | Kirschner et al. |
| 2005/0054724 A1 | 3/2005 | Mustad et al. |
| 2005/0070008 A1 | 3/2005 | Wong et al. |
| 2005/0075398 A1 | 4/2005 | Bazan et al. |
| 2005/0101563 A1 | 5/2005 | Pulaski et al. |
| 2005/0113449 A1 | 5/2005 | Renshaw |
| 2005/0129739 A1 | 6/2005 | Kohn et al. |
| 2005/0129830 A1 | 6/2005 | Koike et al. |
| 2005/0137253 A1 | 6/2005 | Phinney et al. |
| 2005/0147665 A1 | 7/2005 | Horrobin et al. |
| 2005/0154059 A1 | 7/2005 | Cook et al. |
| 2005/0170479 A1 | 8/2005 | Weaver et al. |
| 2005/0171200 A1 | 8/2005 | Calder et al. |
| 2005/0202063 A1 | 9/2005 | Venturi |
| 2005/0209329 A1 | 9/2005 | Horrobin |
| 2005/0245610 A1 | 11/2005 | Verboom et al. |
| 2005/0266051 A1 | 12/2005 | Kelley et al. |
| 2005/0273885 A1 | 12/2005 | Singh et al. |
| 2006/0004099 A1 | 1/2006 | Roe |
| 2006/0009486 A1 | 1/2006 | Mitchell |
| 2006/0009522 A1 | 1/2006 | Dana et al. |
| 2006/0020031 A1 | 1/2006 | Berlin |
| 2006/0024404 A1 | 2/2006 | Kyle |
| 2006/0051847 A1 | 3/2006 | Gunnarsson et al. |
| 2006/0057185 A1 | 3/2006 | Akimoto et al. |
| 2006/0058384 A1 | 3/2006 | Hogg |
| 2006/0068076 A1 | 3/2006 | Bertholet et al. |
| 2006/0073187 A1 | 4/2006 | Akimoto et al. |
| 2006/0088502 A1 | 4/2006 | Sata et al. |
| 2006/0088573 A1 | 4/2006 | Ishikura et al. |
| 2006/0099321 A1 | 5/2006 | Sievert |
| 2006/0099693 A1 | 5/2006 | Kobzeff et al. |
| 2006/0105033 A1 | 5/2006 | Bendich |
| 2006/0127450 A1 | 6/2006 | Chinen |
| 2006/0135608 A1 | 6/2006 | Horrobin et al. |
| 2006/0142255 A1 | 6/2006 | Fabry |
| 2006/0142390 A1 | 6/2006 | Manku et al. |
| 2006/0153940 A1 | 7/2006 | Prous |
| 2006/0165735 A1 | 7/2006 | Abril et al. |
| 2006/0166935 A1 | 7/2006 | Bryhn |
| 2006/0178436 A1 | 8/2006 | Domingo Pedral |
| 2006/0182820 A1 | 8/2006 | Kluetz et al. |
| 2006/0205814 A1 | 9/2006 | Granata et al. |
| 2006/0211749 A1 | 9/2006 | Bobotas et al. |
| 2006/0211763 A1 | 9/2006 | Fawzy et al. |
| 2006/0217356 A1 | 9/2006 | Wright et al. |
| 2006/0217442 A1 | 9/2006 | Ishikura et al. |
| 2006/0229366 A1 | 10/2006 | Lifschitz et al. |
| 2006/0233762 A1 | 10/2006 | McMahon et al. |
| 2006/0270625 A1 | 11/2006 | Vinik et al. |
| 2006/0280776 A1 | 12/2006 | Koide |
| 2006/0287256 A1 | 12/2006 | Raederstorff et al. |
| 2006/0292217 A1 | 12/2006 | Schmidt et al. |
| 2007/0003639 A1 | 1/2007 | Le Hen Ferrenbach et al. |
| 2007/0003686 A1 | 1/2007 | Fichtali et al. |
| 2007/0004678 A1 | 1/2007 | Kohn et al. |
| 2007/0009495 A1 | 1/2007 | McMahon et al. |
| 2007/0010480 A1 | 1/2007 | Rusing et al. |
| 2007/0020340 A1 | 1/2007 | Rubin et al. |
| 2007/0032548 A1 | 2/2007 | Ellis |
| 2007/0036862 A1 | 2/2007 | Rongen et al. |
| 2007/0042008 A1 | 2/2007 | Kane et al. |
| 2007/0042953 A1 | 2/2007 | Bazan et al. |
| 2007/0060651 A1 | 3/2007 | Larson et al. |
| 2007/0082063 A1 | 4/2007 | Bibus et al. |
| 2007/0087957 A1 | 4/2007 | Kidron |
| 2007/0098787 A1 | 5/2007 | Kakiuchi |
| 2007/0104779 A1 | 5/2007 | Rongen et al. |
| 2007/0112071 A1 | 5/2007 | Bryhn et al. |
| 2007/0122452 A1 | 5/2007 | Moriguchi et al. |
| 2007/0128292 A1 | 6/2007 | Predal |
| 2007/0128341 A1 | 6/2007 | Bakkene et al. |
| 2007/0134349 A1 | 6/2007 | McDonnell et al. |
| 2007/0141096 A1 | 6/2007 | Van Lengerich |
| 2007/0141138 A1 | 6/2007 | Feuerstein et al. |
| 2007/0141220 A1 | 6/2007 | Lee et al. |
| 2007/0142456 A1 | 6/2007 | Kuhajda et al. |
| 2007/0149617 A1 | 6/2007 | Deckelbaum et al. |
| 2007/0154498 A1 | 7/2007 | Bortz et al. |
| 2007/0161705 A1 | 7/2007 | Bruzzese |
| 2007/0166411 A1 | 7/2007 | Anthony et al. |

| | | | |
|---|---|---|---|
| 2007/0166413 A1 | 7/2007 | Haber et al. |
| 2007/0184135 A1 | 8/2007 | Palu et al. |
| 2007/0191467 A1 | 8/2007 | Rongen et al. |
| 2007/0196505 A1 | 8/2007 | Friesen et al. |
| 2007/0202052 A1 | 8/2007 | Brenna et al. |
| 2007/0203235 A1 | 8/2007 | Rosales et al. |
| 2007/0203237 A1 | 8/2007 | Brenna et al. |
| 2007/0203238 A1 | 8/2007 | Jouni et al. |
| 2007/0207223 A1 | 9/2007 | DiRienzo et al. |
| 2007/0207975 A1 | 9/2007 | Menendez et al. |
| 2007/0218113 A1 | 9/2007 | Miller et al. |
| 2007/0225370 A1 | 9/2007 | Opheim |
| 2007/0243307 A1 | 10/2007 | Abril et al. |
| 2007/0248586 A1 | 10/2007 | Arterburn et al. |
| 2007/0259037 A1 | 11/2007 | Guivarc'h et al. |
| 2007/0264222 A1 | 11/2007 | Georgiades |
| 2007/0265341 A1 | 11/2007 | Dana et al. |
| 2007/0270493 A1 | 11/2007 | Sakakibara et al. |
| 2007/0280998 A1 | 12/2007 | Milligan et al. |
| 2007/0298079 A1 | 12/2007 | Rivera et al. |
| 2008/0005811 A1 | 1/2008 | Metz et al. |
| 2008/0015166 A1 | 1/2008 | Van Tol et al. |
| 2008/0020086 A1 | 1/2008 | Abril et al. |
| 2008/0020124 A1 | 1/2008 | Kawashima et al. |
| 2008/0031814 A1 | 2/2008 | Hageman |
| 2008/0031869 A1 | 2/2008 | Fontaine |
| 2008/0032957 A1 | 2/2008 | Xu |
| 2008/0039525 A1 | 2/2008 | Mustad et al. |
| 2008/0044481 A1 | 2/2008 | Harel |
| 2008/0044487 A1 | 2/2008 | Bruheim et al. |
| 2008/0045594 A1 | 2/2008 | Piccirilli et al. |
| 2008/0076823 A1 | 3/2008 | Watkins et al. |
| 2008/0085911 A1 | 4/2008 | Rongen et al. |
| 2008/0096964 A1 | 4/2008 | Subramanian et al. |
| 2008/0113046 A1 | 5/2008 | Gardette |
| 2008/0118441 A1 | 5/2008 | Washington |
| 2008/0125490 A1 | 5/2008 | Svensson et al. |
| 2008/0305210 A1 | 12/2008 | Peterson |
| 2009/0234007 A1 | 9/2009 | Hoffman |

FOREIGN PATENT DOCUMENTS

| | | |
|---|---|---|
| EP | 0711503 A2 | 5/1996 |
| EP | 0713653 A1 | 5/1996 |
| EP | 0782827 A1 | 7/1997 |
| WO | WO-96/31457 A1 | 10/1996 |
| WO | WO-97/21434 A1 | 6/1997 |
| WO | WO-98/16216 A1 | 4/1998 |
| WO | WO-01/46115 A1 | 6/2001 |
| WO | WO-02/092540 A1 | 11/2002 |
| WO | WO-03/101225 A1 | 12/2003 |
| WO | WO-2004/112507 A1 | 12/2004 |
| WO | WO-2005/018630 A1 | 3/2005 |
| WO | WO-2005/063231 A2 | 7/2005 |
| WO | WO-2006/017627 A2 | 2/2006 |
| WO | WO-2006/054316 A1 | 5/2006 |
| WO | WO-2006/062748 A2 | 6/2006 |
| WO | WO-2006/067498 A1 | 6/2006 |
| WO | WO-2006/085346 A1 | 8/2006 |
| WO | WO-2006/085672 A2 | 8/2006 |
| WO | WO-2006/088418 A1 | 8/2006 |
| WO | WO-2006/107736 A1 | 10/2006 |
| WO | WO-2006/111295 A1 | 10/2006 |
| WO | WO-2006/116755 A2 | 11/2006 |
| WO | WO-2006/120120 A1 | 11/2006 |
| WO | WO-2006/127627 A2 | 11/2006 |
| WO | WO-2007/002837 A2 | 1/2007 |
| WO | WO-2007/004685 A2 | 1/2007 |
| WO | WO-2007/004689 A1 | 1/2007 |
| WO | WO-2007/006672 A1 | 1/2007 |
| WO | WO-2007/011886 A2 | 1/2007 |
| WO | WO-2007/017240 A2 | 2/2007 |
| WO | WO-2007/030718 A2 | 3/2007 |
| WO | WO-2007/039596 A1 | 4/2007 |
| WO | WO-2007/041418 A2 | 4/2007 |
| WO | WO-2007/057090 A1 | 5/2007 |
| WO | WO-2007/057511 A1 | 5/2007 |
| WO | WO-2007/058538 A2 | 5/2007 |
| WO | WO-2007/062325 A1 | 5/2007 |
| WO | WO-2007/071733 A2 | 6/2007 |
| WO | WO-2007/086931 A1 | 8/2007 |
| WO | WO-2007/089685 A2 | 8/2007 |
| WO | WO-2007/090162 A2 | 8/2007 |
| WO | WO-2007/100566 A2 | 9/2007 |
| WO | WO-2007/116052 A1 | 10/2007 |
| WO | WO-2007/117511 A2 | 10/2007 |
| WO | WO-2007/135141 A1 | 11/2007 |
| WO | WO-2007/145520 A1 | 12/2007 |
| WO | WO-2007/149591 A2 | 12/2007 |
| WO | WO-2008/000440 A1 | 1/2008 |
| WO | WO-2008/004900 A1 | 1/2008 |
| WO | WO-2008/006607 A2 | 1/2008 |
| WO | WO-2008/011178 A2 | 1/2008 |
| WO | WO-2008/011179 A2 | 1/2008 |
| WO | WO-2008/028631 A2 | 3/2008 |
| WO | WO-2008/028632 A1 | 3/2008 |
| WO | WO-2008/028633 A1 | 3/2008 |
| WO | WO-2008/028634 A1 | 3/2008 |
| WO | WO-2008/028635 A1 | 3/2008 |
| WO | WO-2008/028636 A1 | 3/2008 |
| WO | WO-2008/036353 A2 | 3/2008 |
| WO | WO-2008/039855 A2 | 4/2008 |
| WO | WO-2008/063323 A2 | 5/2008 |

OTHER PUBLICATIONS

Bigogno et al., Accumulation of arachidonic acid-rich triacyglycerols in the microalga *Parietochloris incise* (Trebuxiophyceae, Chlorophyta), Phytochemistry 60, pp. 135-143 (2002).

Bigogno et al., Lipid and fatty acid composition of the green oleaginous alga *Parietochloris incise*, the richest plant source of arachidonic acid, Phytochemistry 60, pp. 497-503 (2002).

Bligh et al., Can. J. Biochem. Physiol. 37, pp. 911-917 (1959).

Broglio et al., Effect of heterotrophic versus autotrophic food on feeding and reproduction of the calanoid copepod *Acartia tonsa*: relationship with prey fatty acid composition, Aquatic Microbial Ecology, vol. 31, pp. 267-278 (2003).

Brosche et al., Effect of borage oil consumption on fatty acid metabolism, transepidermal water loss and skin parameters in elderly people, Archives of Gerontology and Geriatrics 30, pp. 139-150 (2000).

Brown et al., The nutritional value of four Australian microalgal strains fed to Pacific oyster *Crassostrea gigas* spat, Aquaculture 165, pp. 281-293 (1998).

Byars et al., Blackcurrant Seed Oil as a Source of Polyunsaturated Fatty Acids in the Treatment of Inflammatory Disease, (Abstract), Biochem. Soc. Trans. 20(12), 139s (1992).

Dunstan et al., Cryptophyceae and rhodophyceae; chemotaxonomy, phylogeny, and application, Phytochemistry 66, pp. 2557-2570 (2005).

Fan et al., Importance of Dietary gamma-Linolenic Acid in Human Health and Nutrition, Recent Advances in Nutritional Science, pp. 1411-1414 (1999).

Fernández-Reiriz et al., Biomass Production and Variation in the Biochemical Profile (Total Protein, Carbohydrates, RNA, Lipids and Fatty Acids) of Seven Species of Marine Microalage, Aquaculture 83, pp. 17-37 (1989).

Garrido et al., Oxygen Production Rate as a Test for Determining Toxicity of Copper to *Rhodomonas salina* Hill and Wehterbee (Cryptophyceae), Bull. Environ. Contam. Toxicol. 62, pp. 776-782 (1999).

Guil-Guerrero et al., Eicosapentaenoic and arachidonic acids purification from the red microalgae *Porphyridium cruentum*, Bioseparation 9, pp. 299-306 (2001).

Hammer et al., Light and temperature acclimation of *Rhodomonas salina* (Cryptophyceae): photosynthetic performance, Aquatic Microbial Ecology, vol. 29:287-296 (2002).

Hampel et al., Acute Toxicity of LAS Homologues in Marine Microalgae: Esterase Activity and Inhibition Growth as Endpoints of Toxicity, Ecotoxicology and Environmental Safety 48, pp. 287-292 (2001).

Hardman, (n-3) Fatty Acids and Cancer Therapy, J. Nutr. 134, pp. 3427S-3430S (2004).

Henz et al., Double-blind, multicentre analysis of the efficacy of borage oil in patients with atopic eczema, British Journal of Dermatology 140, pp. 685-688 (1999).

Horrobin et al., Clinical Biochemistry of Essential Fatty Acids, in: Omega-6 Essential Fatty Acid:, Pathophysiology and Roles in Clinical Medicine, pp. 21-53 (1990).

Huang et al., Modulation of Tissue Fatty Acid Composition, Prostaglandin Production and Cholesterol Levels by Dietary Manipulation of n-3 and n-6 Essential Fatty Acid Metabolites, Omega-6 Essential Fatty Acids, Pathophysiology and Roles in Clinical Medicine, pp. 127-144 (1990).

James et al., Metabolism of stearidonic acid in human subjects: comparison with the metabolism of other n-3 fatty acids, A.J. Clin. Nutr. 77, pp. 1140-1145 (2003).

Kawashima et al.,Inhibitory Effects of Alkyl Gallate and Its Derivatives on Fatty Acid Desaturation, Biochemica et Biophysica Acta 1299 pp. 34-38 (1996).

Khozin et al., Elucidation of the Biosynthesis of Eicosapentaenoic Acid in the Microalgal *Porphyridium cruentum*: II. Studies with Radiolabeled Precursors, Plant Physiol. 114, pp. 223-230 (1997).

Kitano et al., Changes in eicosapentaenoic acid content of *Navicula saprophila, Rhodomonas salina* and *Nitzschia* sp. under mixotrophic conditions, Journal of Applied Phycology 9:559-563 (1997).

Laposata et al., Eicosadiynoic Acid: A Non-Toxic Inhibitor of Multiple Enzymatic Steps in the Production of Icosanoids from Arachidonic Acid, Dept. of Pathology and Laboratory Medicine, University of Pennsylvania School of Medicine and Division of Hematology-Oncology, Depts. of Internal Medicine and Biological Chemistry, Washington University School of Medicine, vol. 33, N. 4:603-615, Apr. 1987.

Liu et al., Effect of Long-Term Dietary Supplementation of High-Gamma-Linolenic Canola Oil verses Borage Oil on Growth, Hematology, Serum Biochemistry, and N-6 Fatty Acid Metabolism in Rats, J. Agric, Food Chem. 52, pp. 3960-3966 (2004).

Maestrini et al., Relative Yields of Marine Algae Grown in Heavily Nutrient-enriched Seawater, La mer 21, pp. 145-150 (1983).

Mansour et al., Lipid and Fatty Acid Yield of Nine Stationary-Phase Microalgae: Applications and Unusual C24-C28 Polyunsaturated Fatty Acids, J. Appl. Phycol. 17, pp. 287-300 (2005).

McHugh et al., *Supercritical Fluid Extraction: Principles and Practice*, Butterworth Publishers, Boston, pp. 1-11 and 181-198 (1986).

Montero et al., Comparative Sensitivity of Seven Marine Microalgae to Cumulative Exposure to Ultraviolet-B Radiation with Daily Increasing Doses, Botanica Marina, vol. 45, pp. 305-315 (2002).

Nassar et al., Response of Tissue Phospholipid Fatty Acid Composition to Dietary (n-6) and Replacement with Marine (n-3) and Saturated Fatty Acids in the Rat, Nutrition Research, vol. 6, pp. 1397-1406 (1986).

Nassar et al., The Influence of Dietary Manipulation with n-3 and n-6 Fatty Acids on Liver and Plasma Phospholipid Fatty Acids in Rats, Lipids, vol. 21 (10), pp. 652-656 (1986).

Obukowicz et al., Identification and Characterization of a Novel Delta6/Delta 5 Fatty Acid Desaturase Inhibitor as a Potential Anti-Inflammatory Agent, vol. 55, pp. 1045-1058 (1998).

Oltra et al., Life history and fatty acid composition of the marine rotifer *Synchaeta cecilia valentina* fed different algae, Marine Ecology Progress Series, vol. 193, pp. 125-133 (2000).

Palombo et al., Metabolic Support: Cyclic vs Continuous Enteral Feeding with omega-3 and gama-linolenic Fatty Acids: Effects on Modulation of Phospholipid Fatty Acids in Rat Lung and Liver Immune Cells, Journal of Parenteral and Enternal Nutrition 21(3), pp. 123-132 (May 1996).

Pulz et al., Valuable Products from Biotechnology of Microalgae, Appl. Microbioal. Biotechnol, 65, pp. 635-548 (2004).

Remington, The Science and Practice of Pharmacy, $19^{th}$ Edition, vol. I, pp. 697-751 (1995).

Remington, The Science and Practice of Pharmacy, $19^{th}$ Edition, vol. II, pp. 1447-1675 (1995).

Renaud et al., Effect of temperature on growth, chemical composition and fatty acid composition of tropical Australian microalgae grown in batch cultures, Aquaculture 211, pp. 195-214 (2002).

Richmond, Editor, Handbook of Microalgal Culture: Biotechnology and Applied Phycology, Blackwell Science Ltd. Oxford OX2-OEL, UK, pp. 3-93, 312-391, and 513-524 (2004).

Rothman et al., Effects of Unsaturated Fatty Acids on Interleukin-1. Beta Production by Human Monocytes, Cytokine 9(12):1008-12 (1997).

Shiran et al., Biosynthesis of Eicosapentaenoic Acid in the Microalga *Porphyridium cruentum*. I: The Use of Externally Supplied Fatty Acids, Lipids, vol. 31, No. 12, pp. 1277-1282 (1996).

Simopoulos, Essential fatty acids in health and chronic disease, *Clin. Nutr.* 70, pp. 560S-569S (1999).

Takahashi et al., Effect of Different Ratios of Dietary n-6 and n-3 Fatty Acids on Fatty Acid Composition, Prostaglandin Formation and Platelet Aggregation in the Rat, Thrombosis Research, vol. 47, pp. 135-146 (1987).

Tremblay et al., Effect of *Rhodomonas salina* addition to a standard hatchery diet during the early ontogeny of the scallop *Pecten maximus*, Aquaculture 262, pp. 410-418 (2007).

Ursin, Modification of Plant Lipids for Human Health: Development of Functional Land-Based Omega-3 Fatty Acids, J. Nutr. 133, pp. 4271-4274 (2003).

Veloza et al., Trophic modification of essential fatty acids by heterotrophic protists and its effects on the fatty acid composition of the copepod *Acartia tonsa*, Marine Biology 148: pp. 779-788 (2006).

Wen et al., Heterotrophic production of eicosapentaenoic acid by microalgae, Biotechnology Advances 21, pp. 273-294 (2003).

Wiltshire et al., Extraction of pigments and fatty acids from the green alga *Scenedesmus obliquus* (Chlorophyceae), Aquatic Ecology 34, pp. 119-126 (2000).

Xu et al., High quality biodiesel production from a microalga *Chlorella protothecoides* by heterotrophic growth in fermenters, Journal of Biotechnology 126, pp. 499-507 (2006).

Zurier et al., Anti-Inflammatory Effects of γ-Linolenic Acid: Studies in Animals and in Cultured Cells, Omega-6 Essential Fatty Acids: Pathophysiology and Roles in Clinical Medicine, pp. 203-221 (1990).

PCT/US08/81498 International Search Report and Written Opinion, Jan. 16, 2009, 8 pgs.

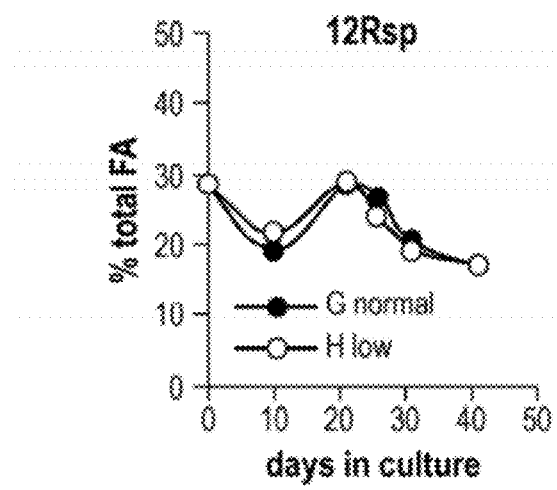
Fig. 20A
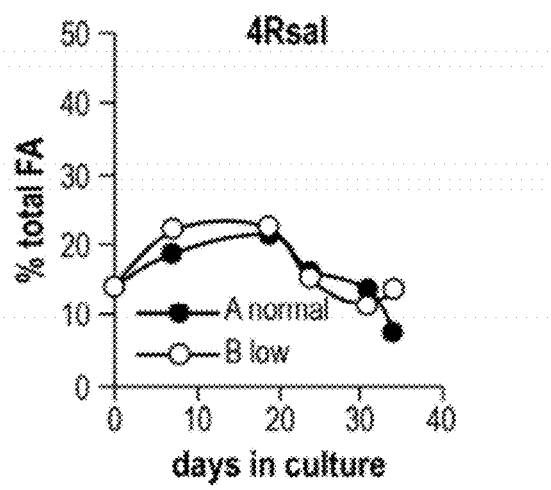
Fig. 20B
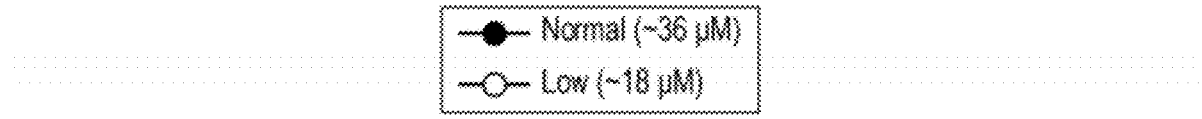
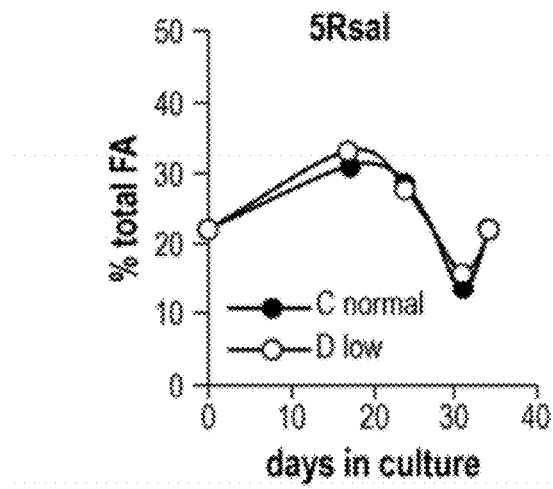
Fig. 20C
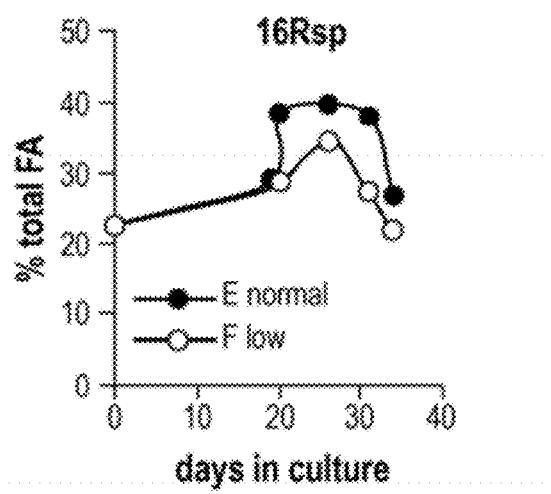
Fig. 20D

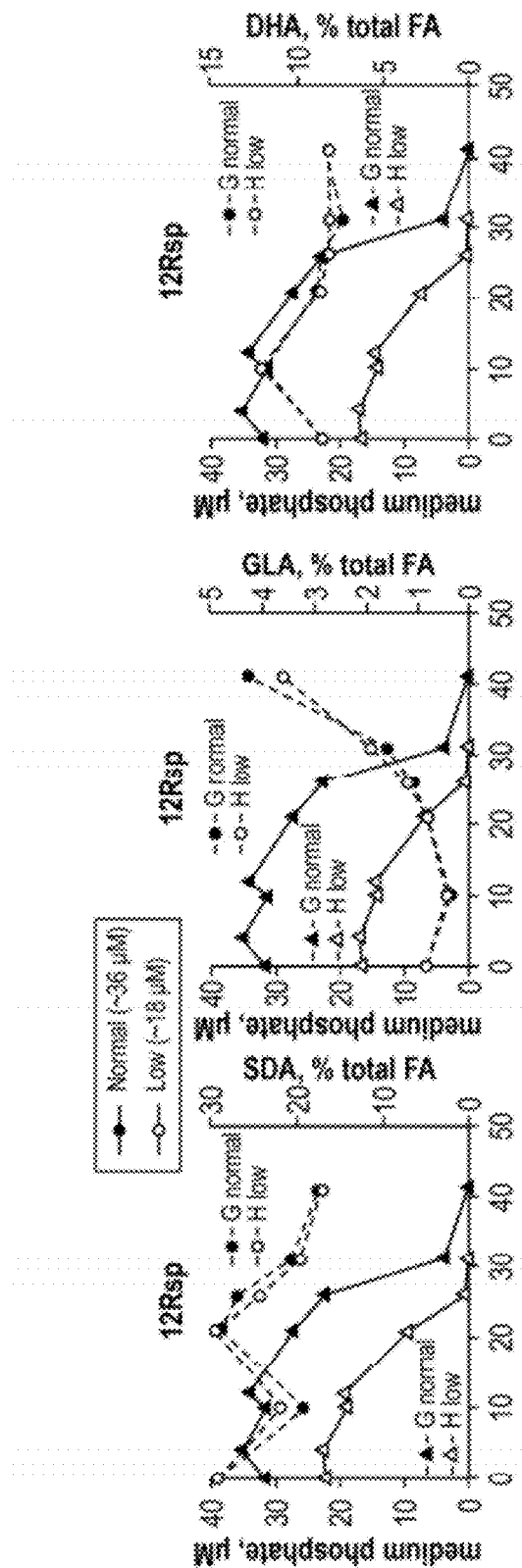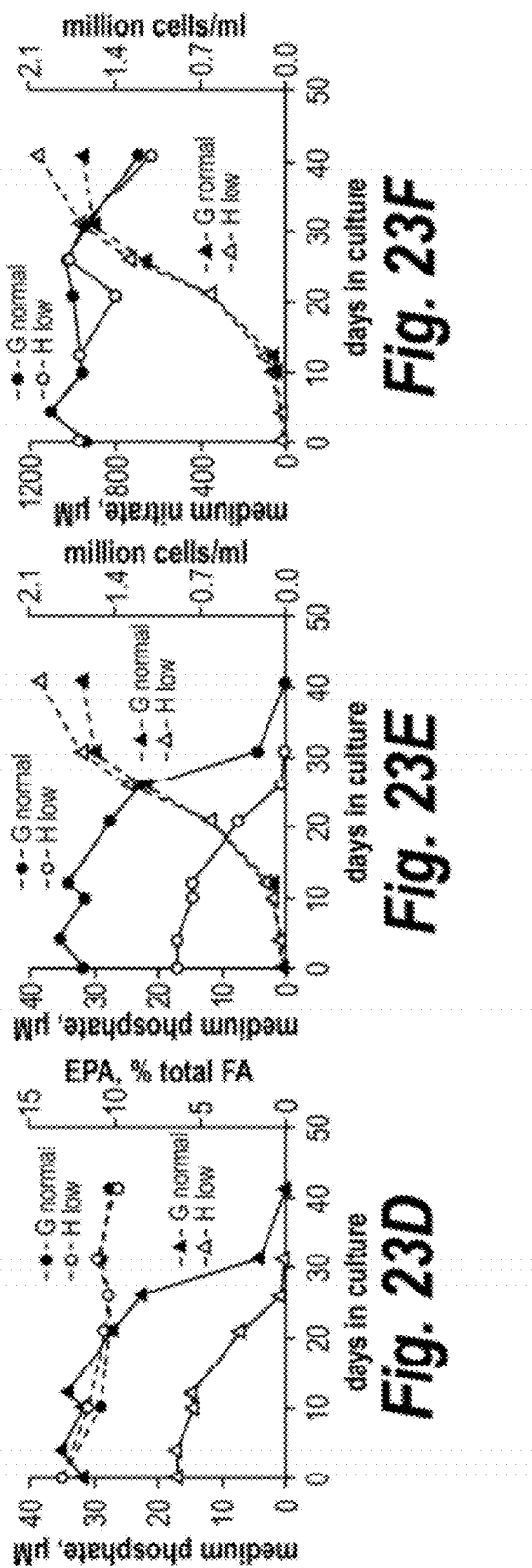

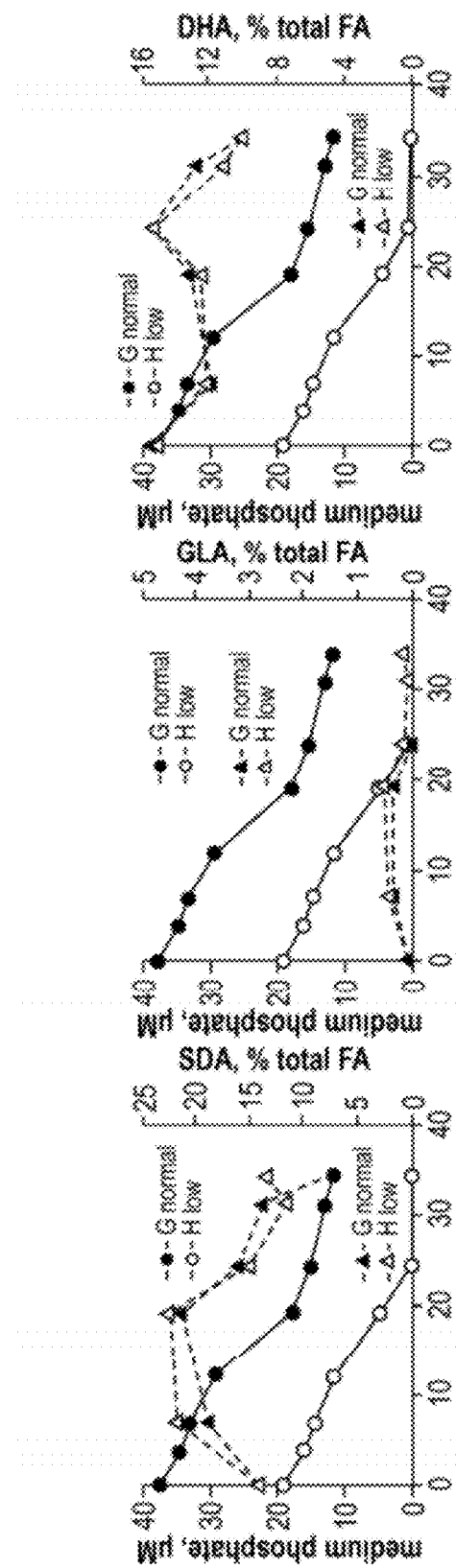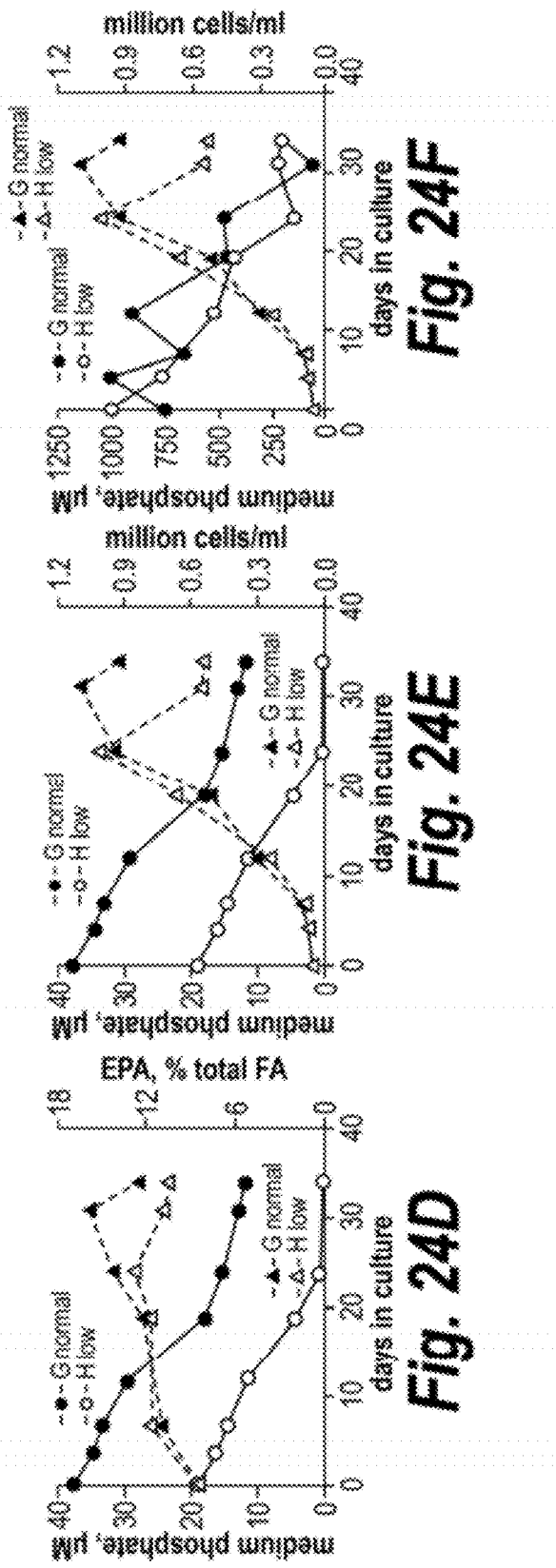

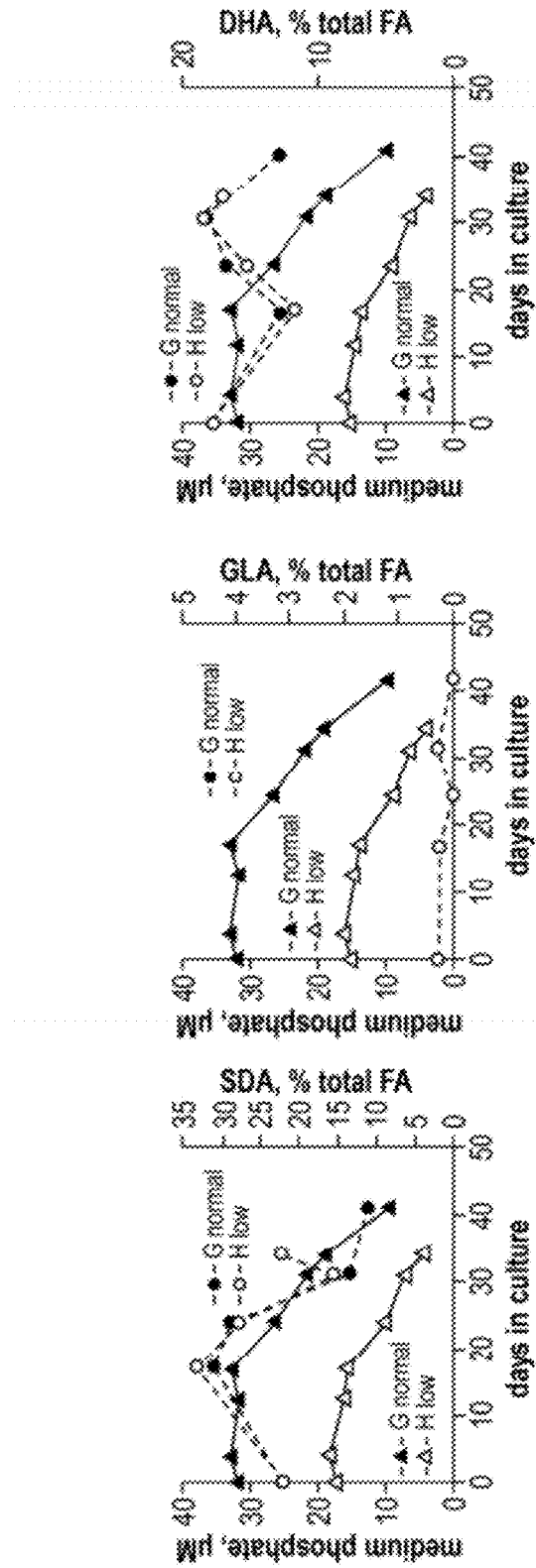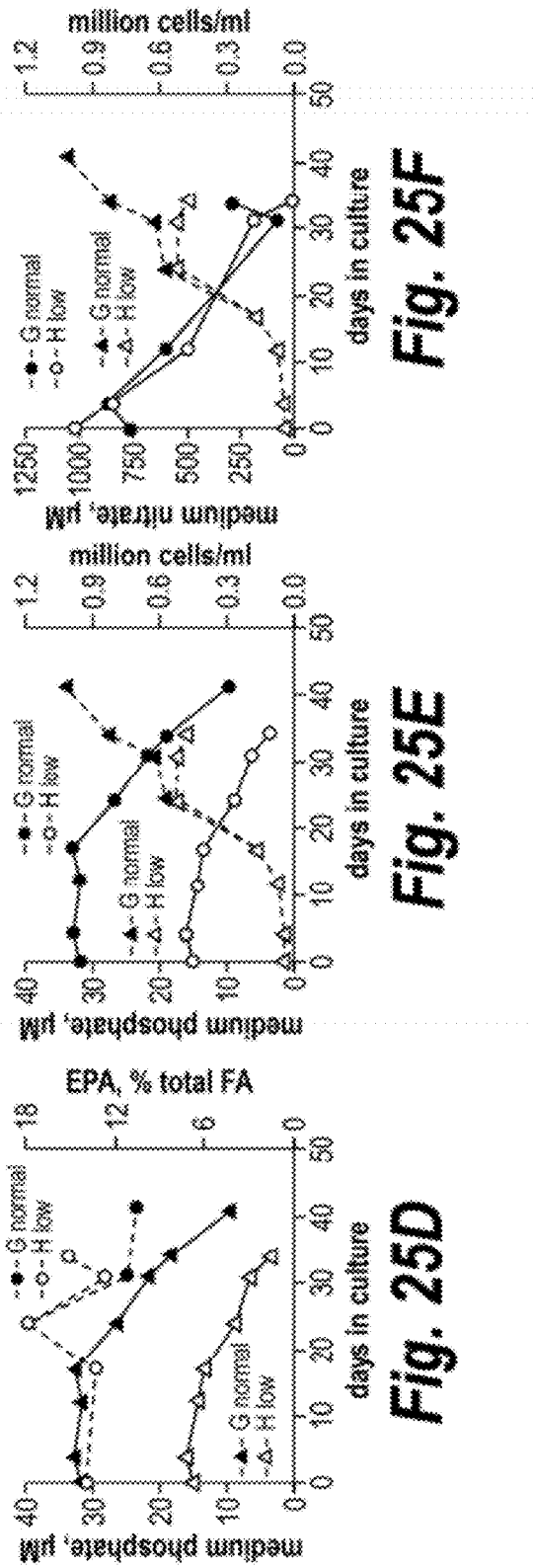

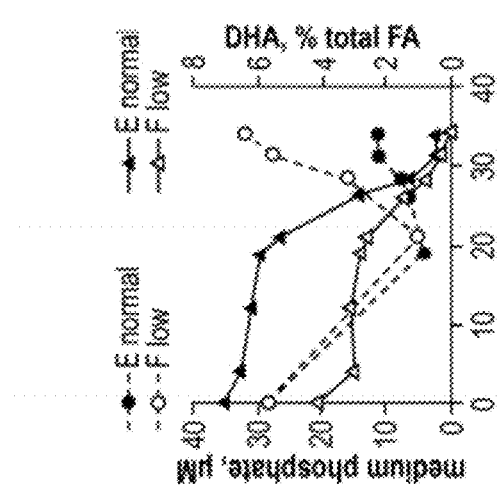
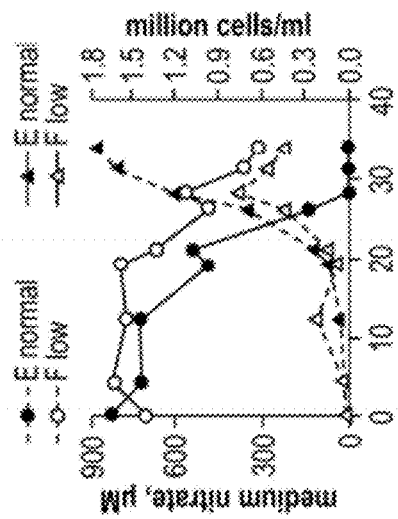
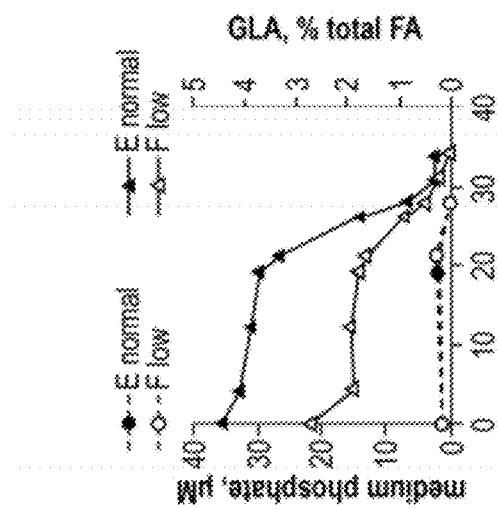
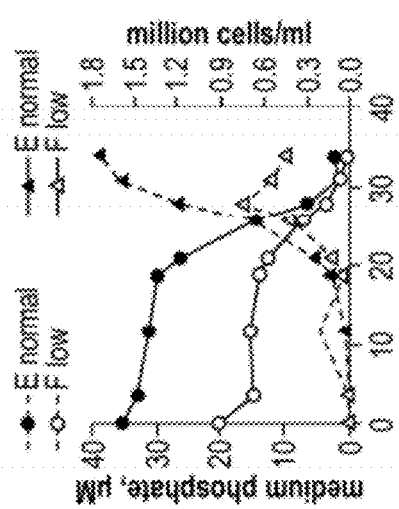
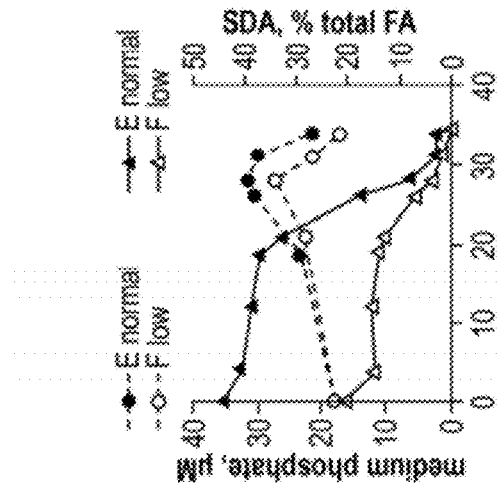
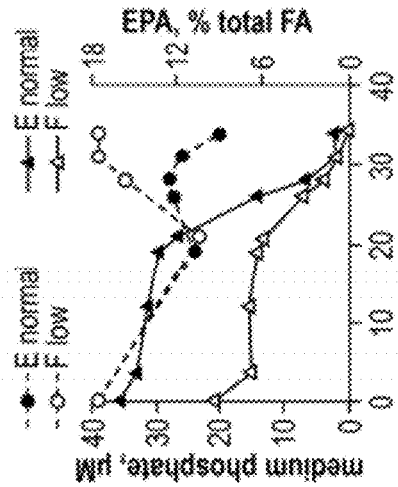

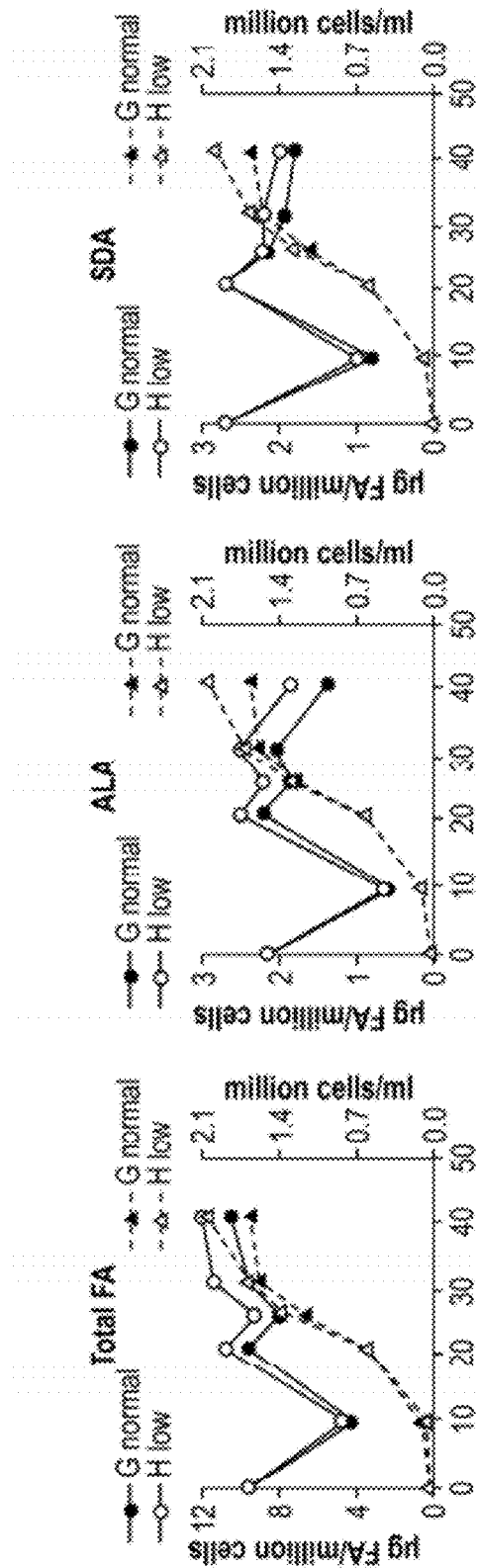
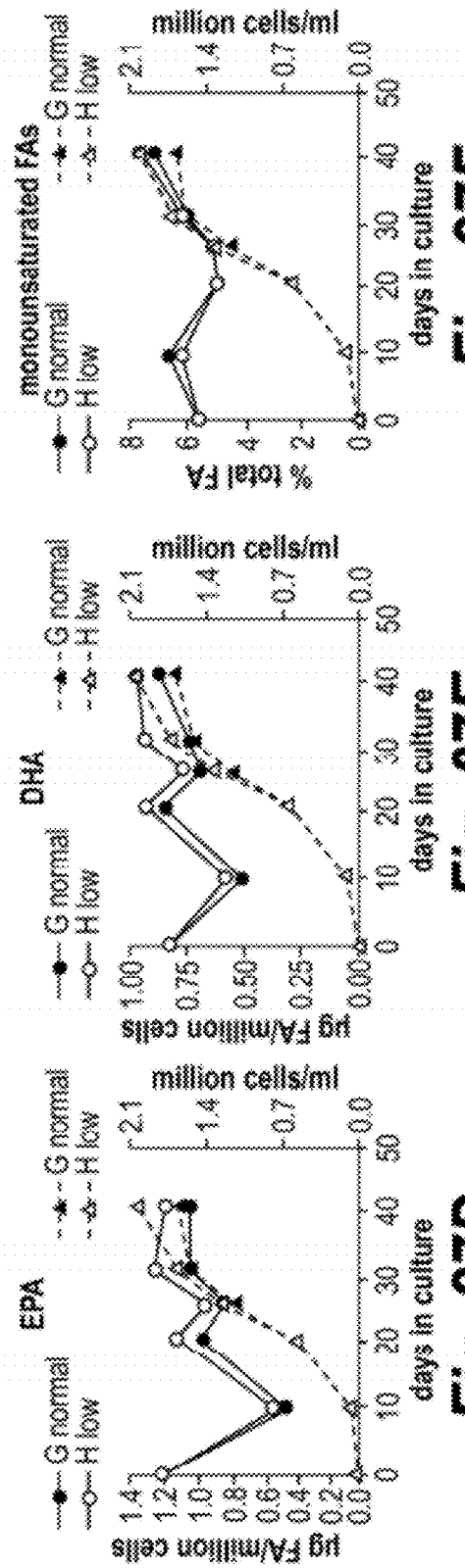

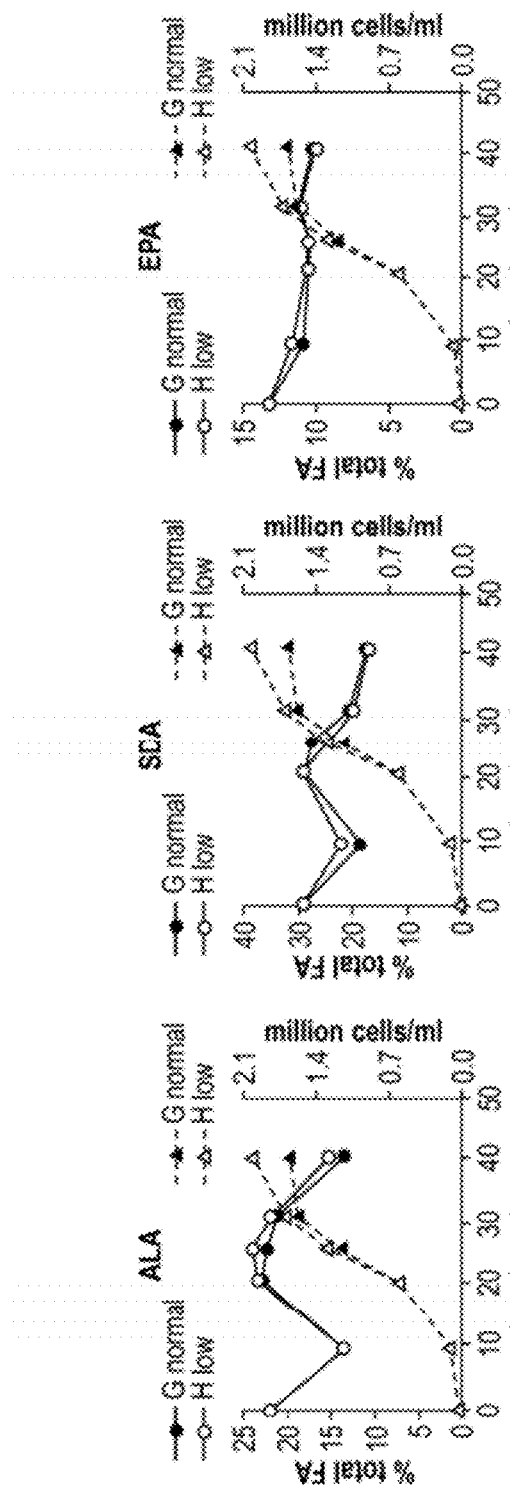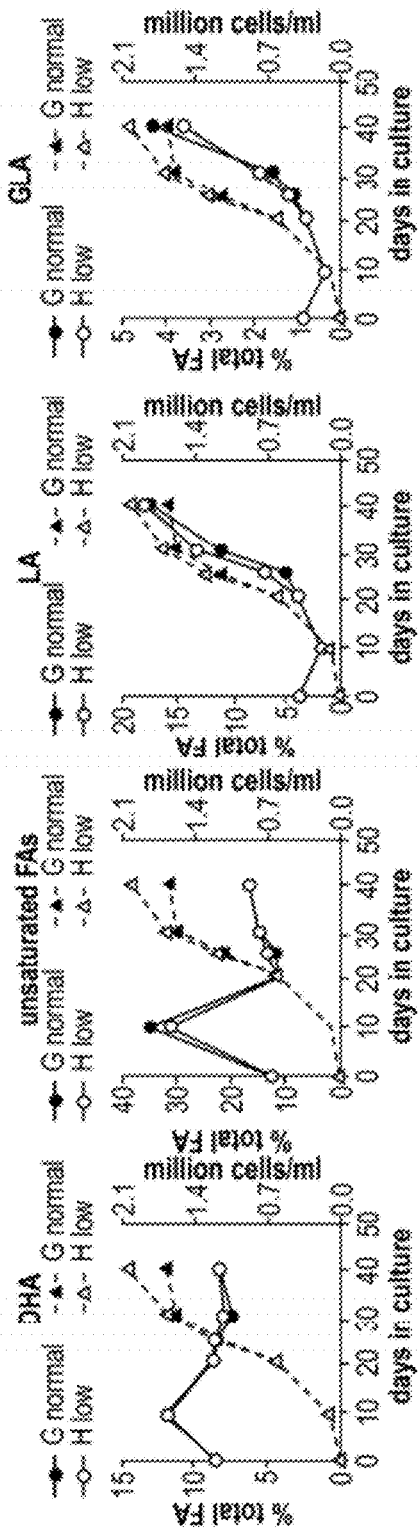

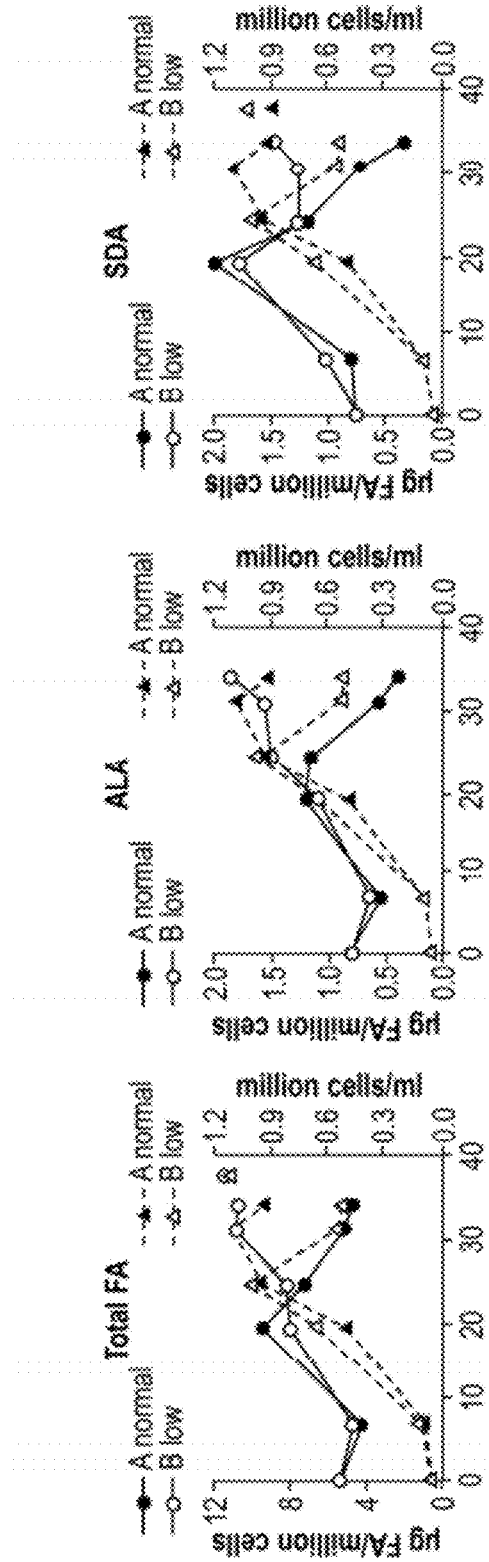
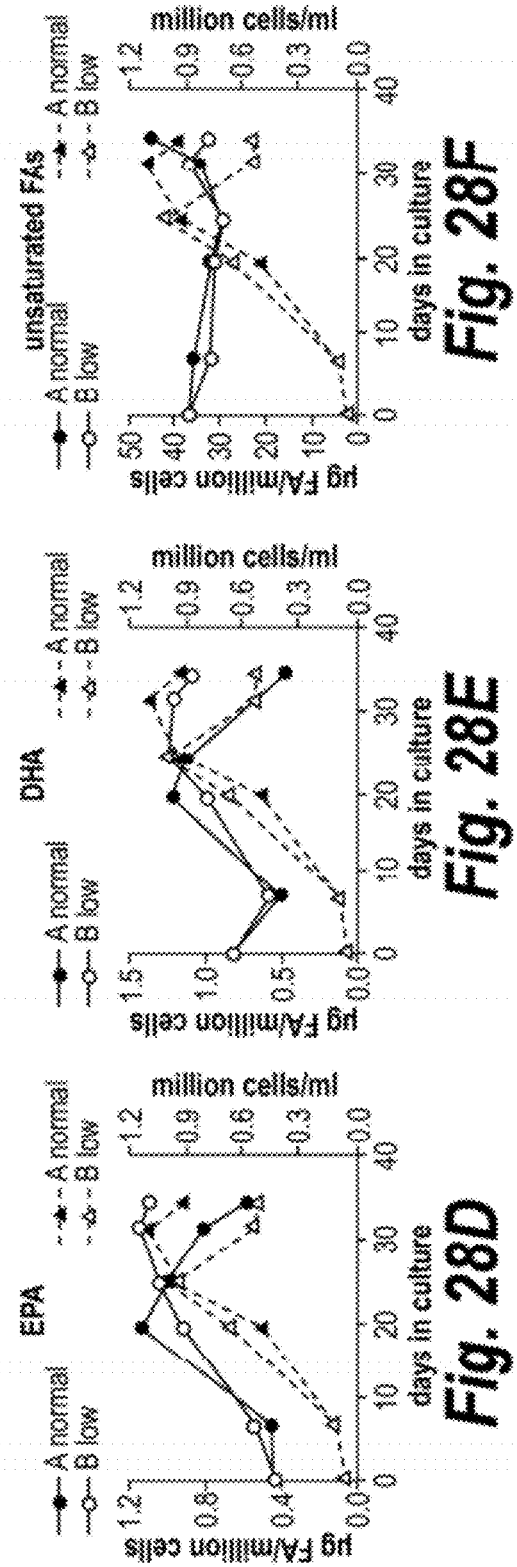

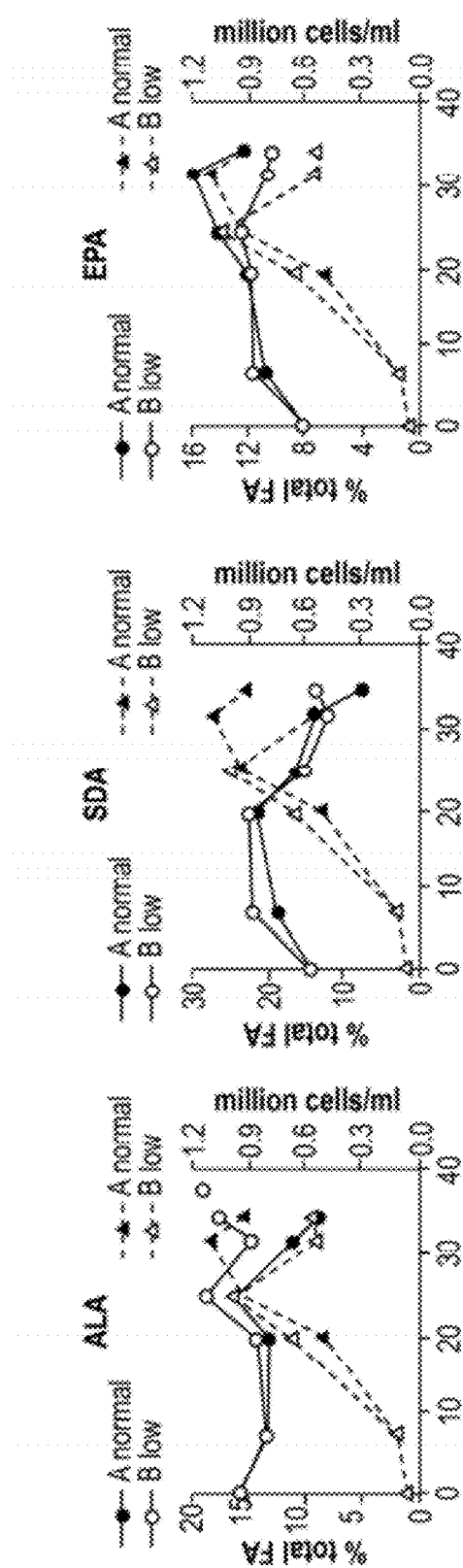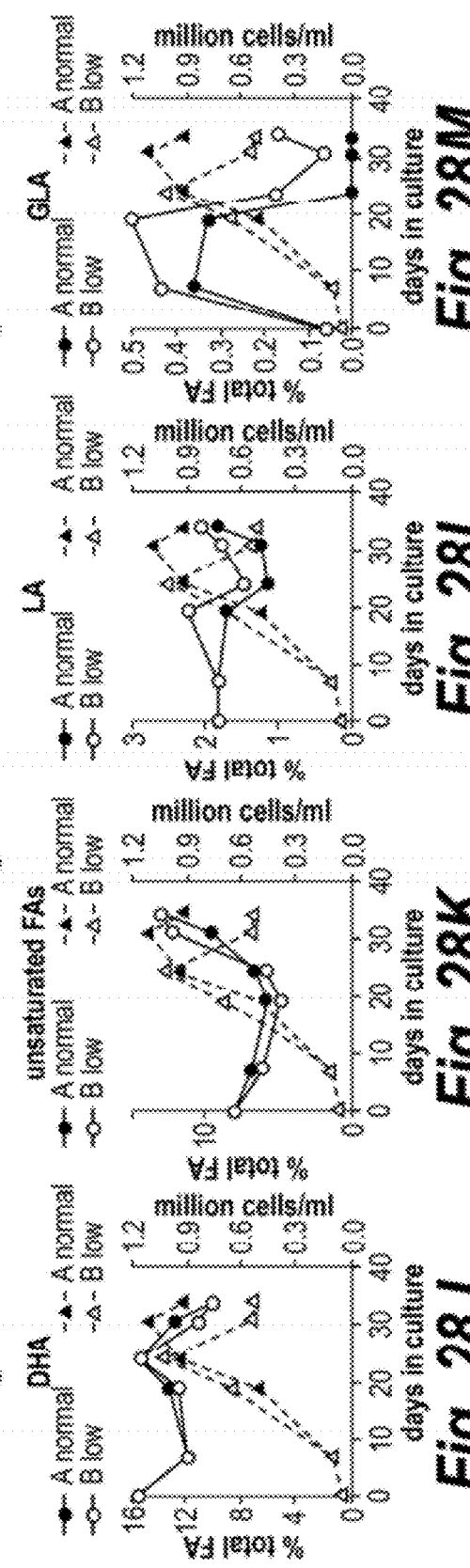

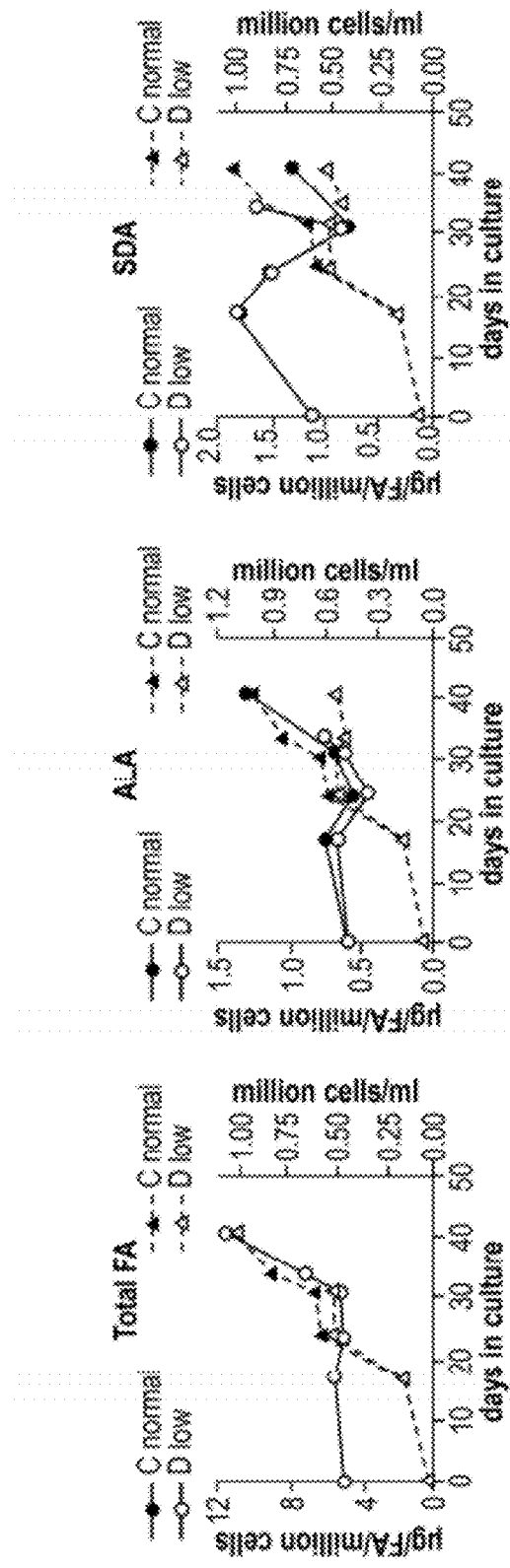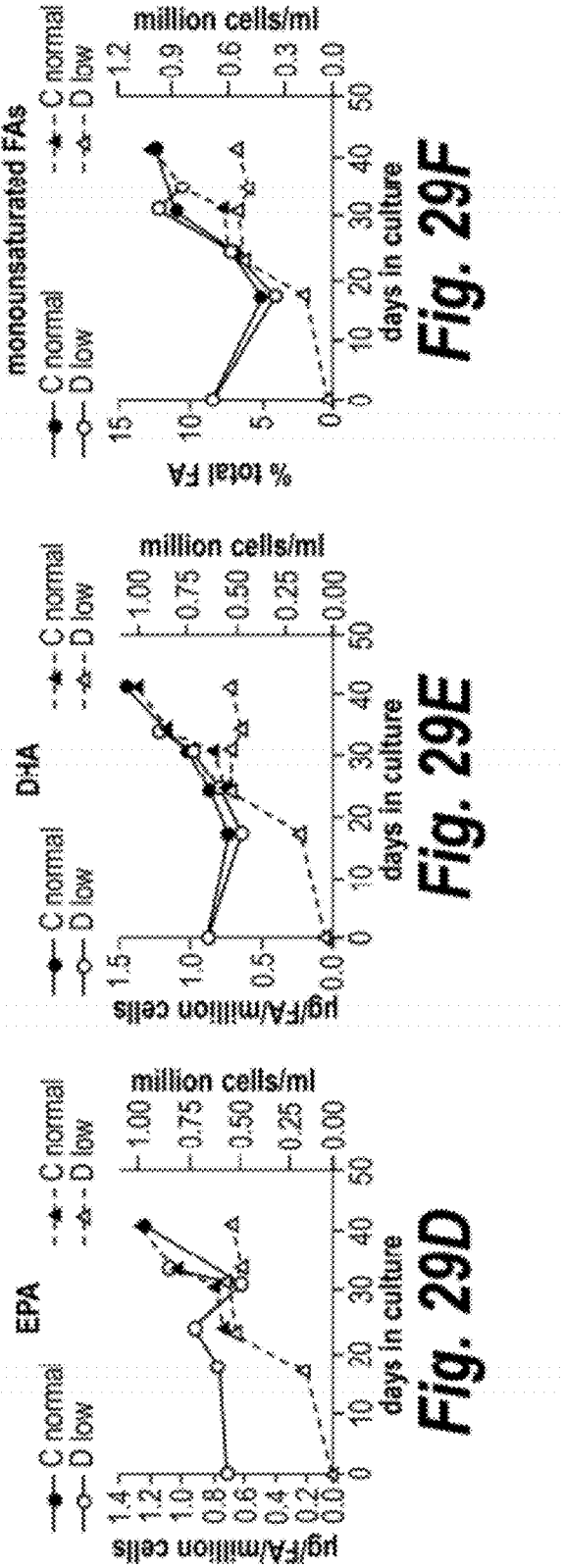

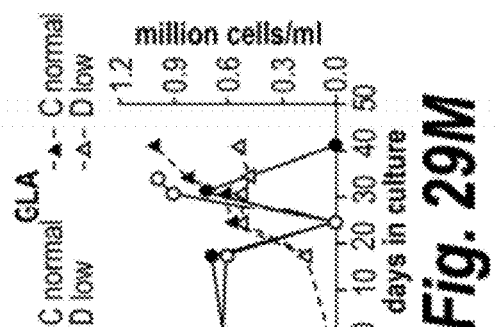
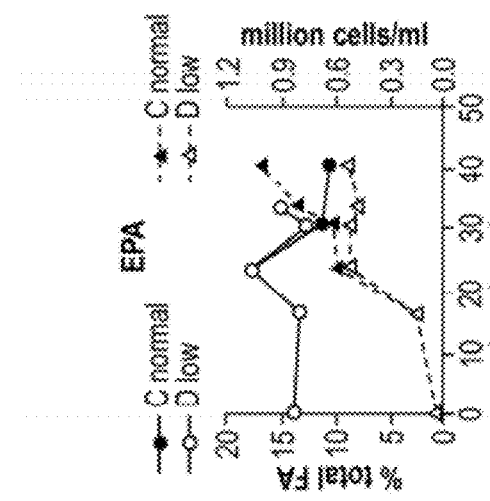
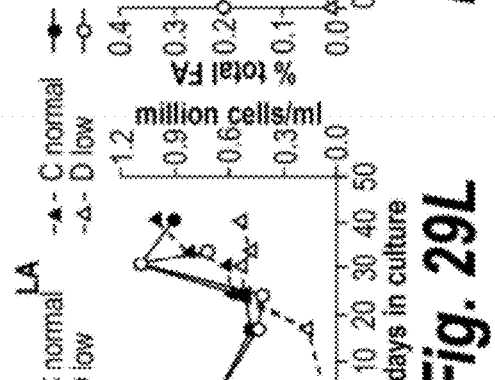
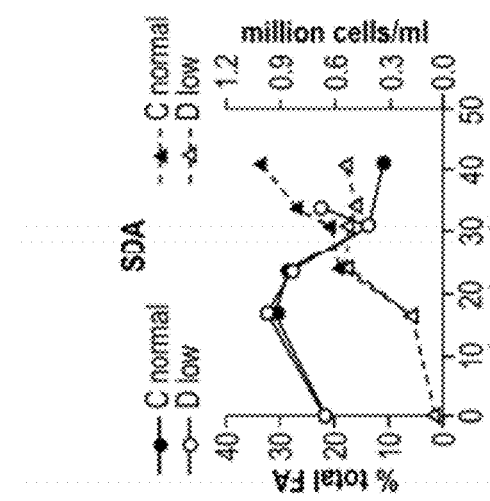
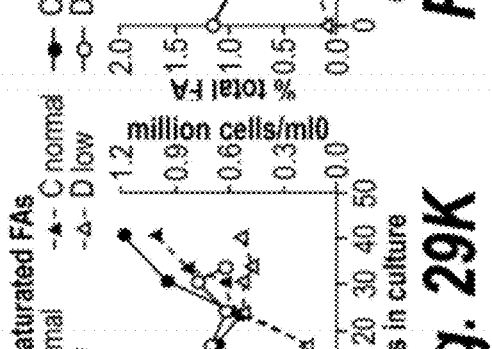
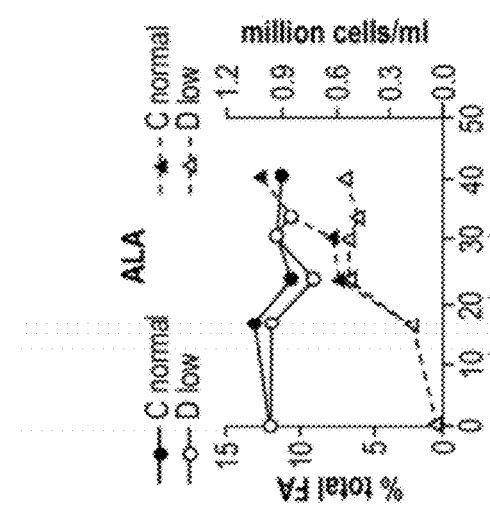
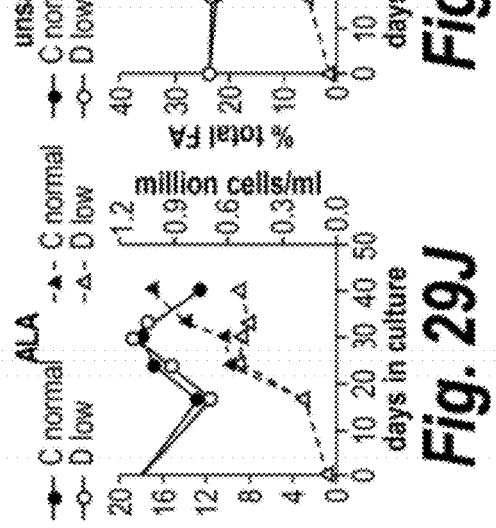

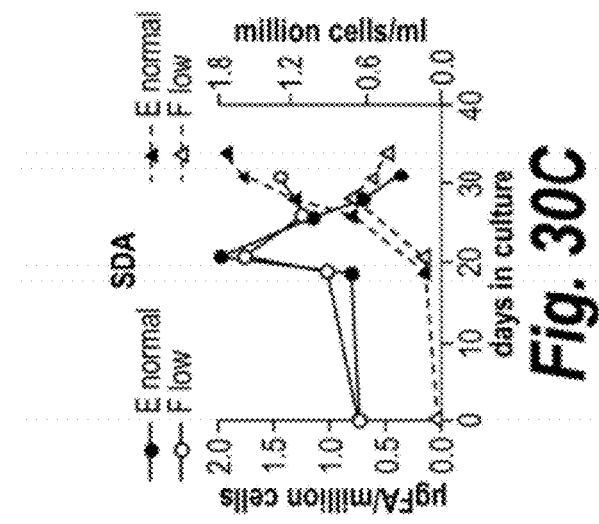
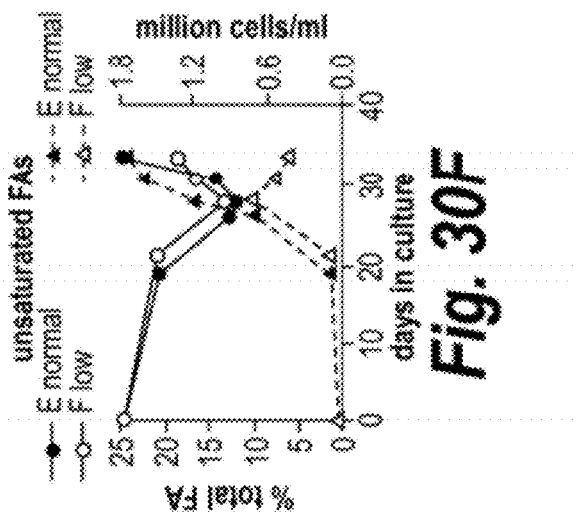
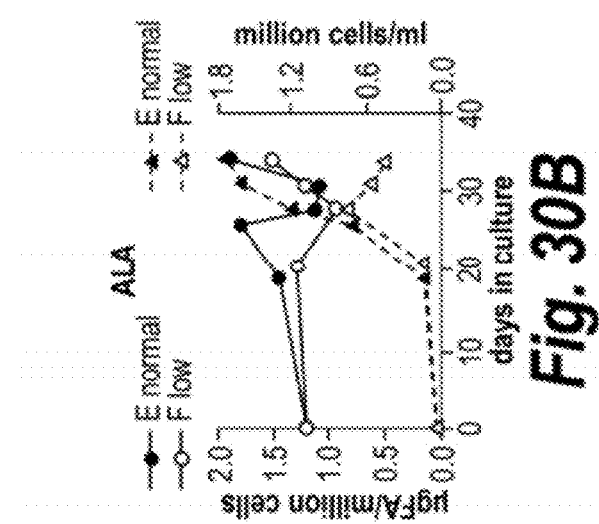
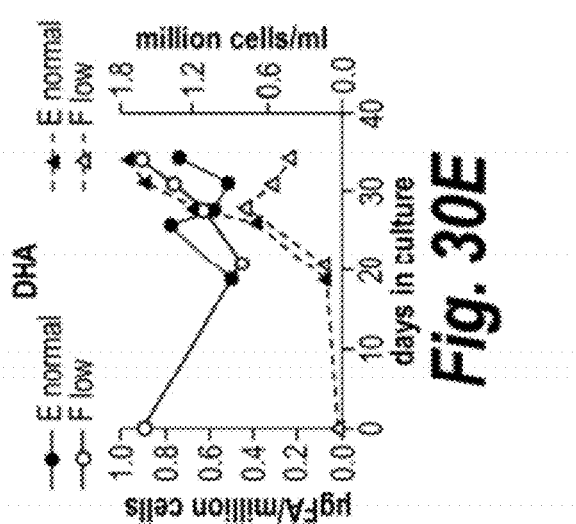
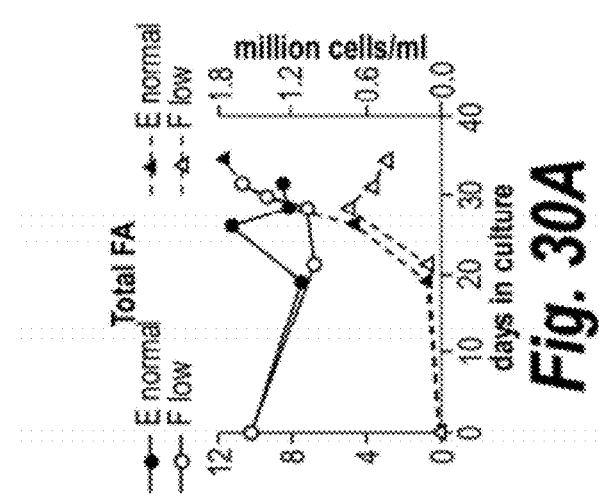
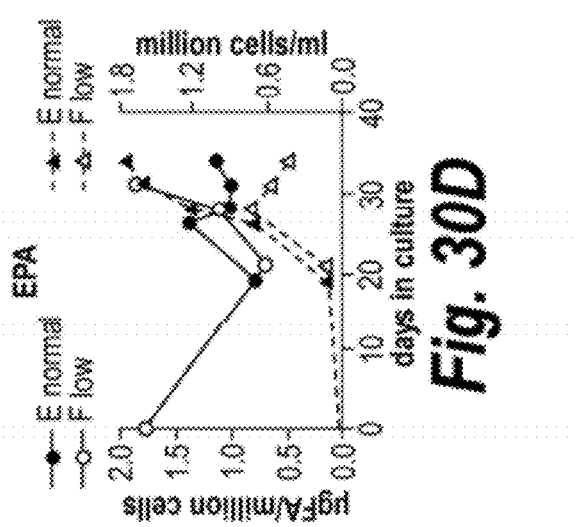

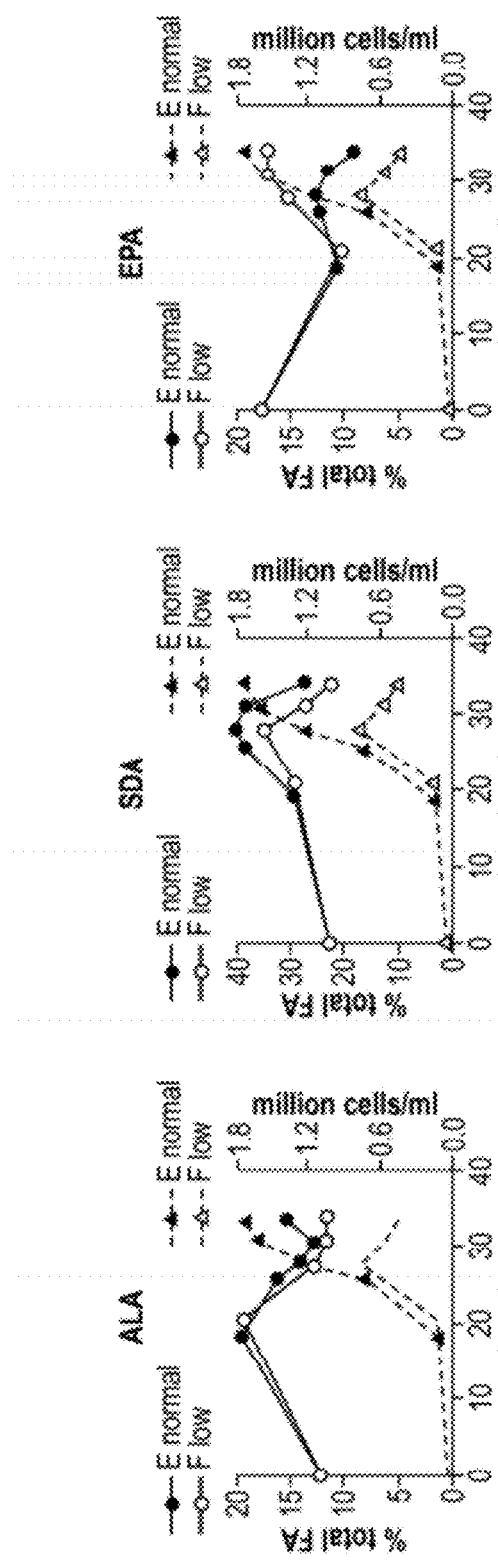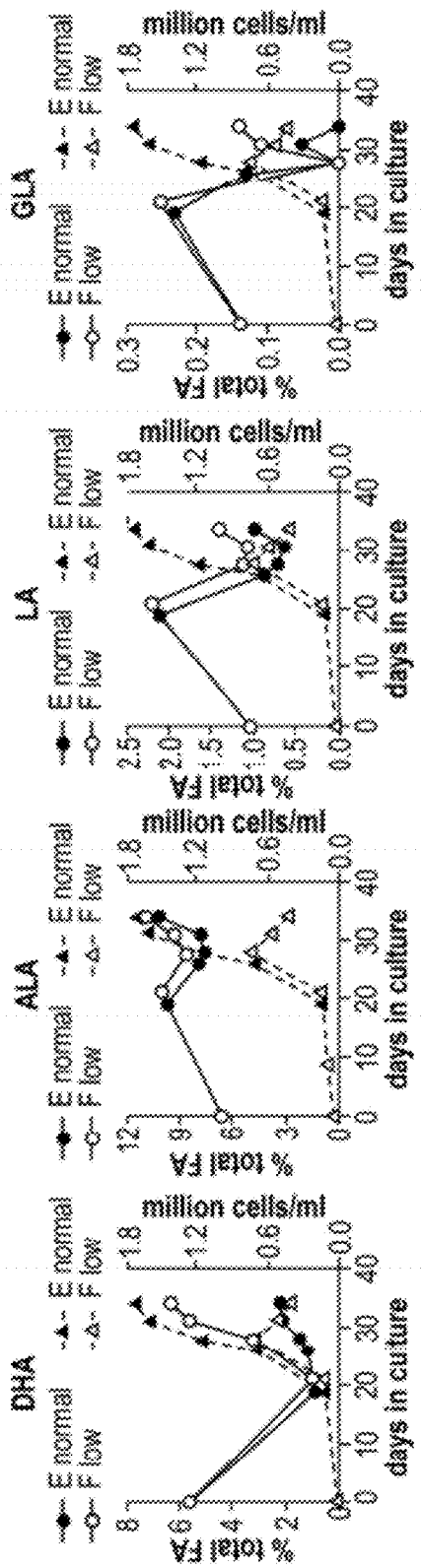
Fig. 30G, Fig. 30H, Fig. 30I, Fig. 30J, Fig. 30K, Fig. 30L, Fig. 30M

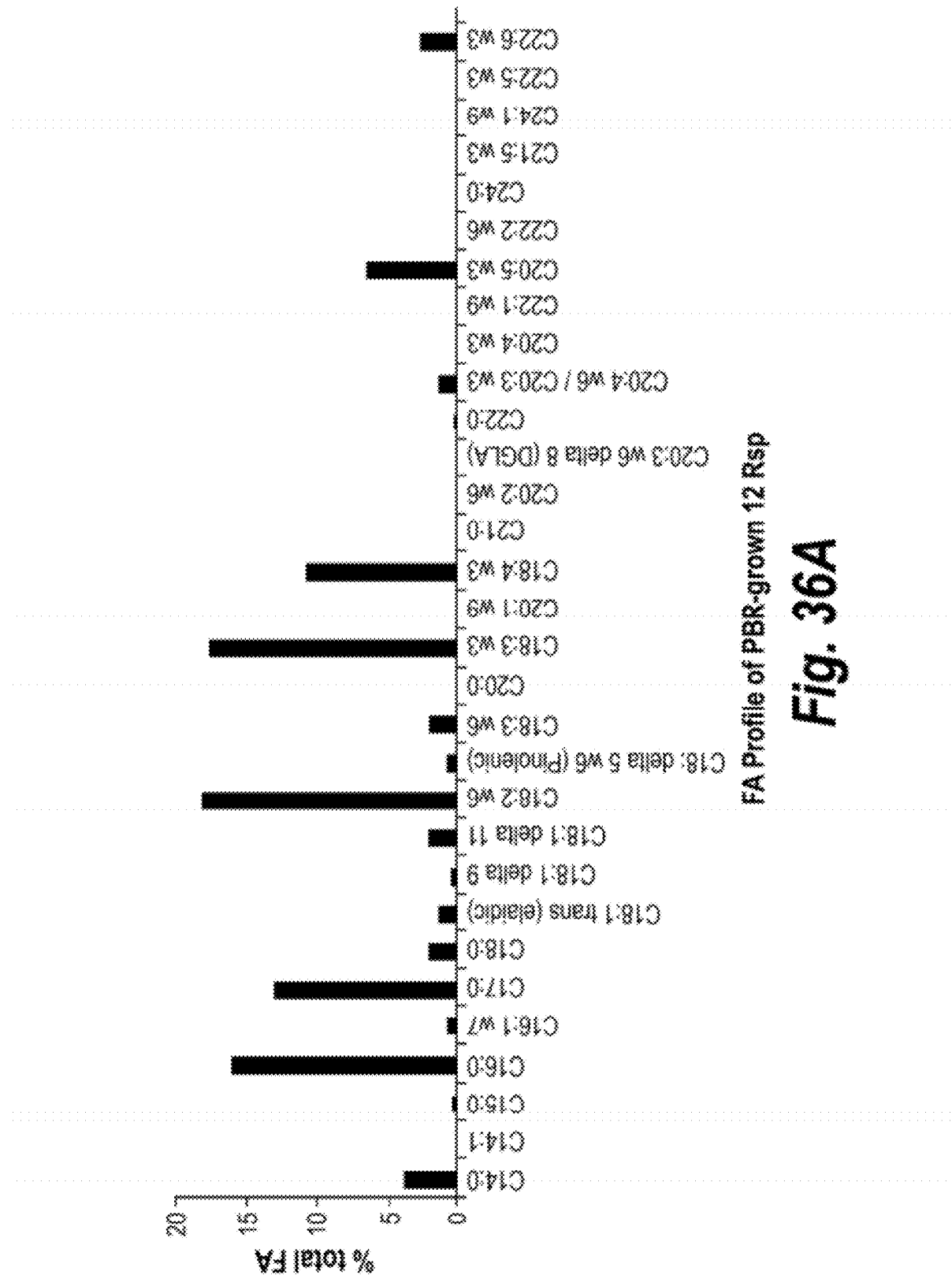

COMPOSITIONS, METHODS, AND KITS FOR POLYUNSATURATED FATTY ACIDS FROM MICROALGAE

CROSS REFERENCE TO RELATED APPLICATIONS

This application is a continuation-in-part of U.S. application Ser. No. 12/260,134, filed Oct. 29, 2008 now abandoned, herein incorporated by reference in its entirety, which claims priority from U.S. Provisional Application No. 61/001,482, filed Nov. 1, 2007, also herein incorporated by reference in its entirety.

This application also is a continuation-in-part of International Application No. PCT/U.S.08/81498, filed on Oct. 29, 2008, also herein incorporated by reference in its entirety, which also claims priority from U.S. Provisional Application No. 61/001,482, filed Nov. 1, 2007.

FIELD OF THE INVENTION

This invention relates generally to the fields of lipid metabolism and dietary supplementation. The present invention also relates to compositions, methods, and kits comprising polyunsaturated fatty acids (PUFAs) produced by a microalgae, in particular microalgae biomass and lipid compositions comprising omega-3 and/or omega-6 fatty acids produced by members of the genus *Rhodomonas*, in particular *Rhodomonas salina*. More particularly, it concerns compositions and methods for preventing and treating mammalian diseases using combinations of polyunsaturated fatty acids from different species of microalgae. Thus, the invention also relates to compositions, methods, and kits comprising the PUFAs produced by the microalgae for the prophylactic and/or therapeutic treatment of a disease or condition, in particular a cardiovascular and/or inflammatory disease or condition.

BACKGROUND OF THE INVENTION

Omega-3 fatty acids are essential for normal human growth and development, and their therapeutic and preventative benefits with regard to cardiovascular disease and rheumatoid arthritis have been well documented (James et al., *A. J. Clin. Nutr.* 77: 1140-1145 (2003); Simopoulos, *A. J. Clin, Nutr.* 70: 560S-569S (1999)). Multiple studies have documented a protective role of fish oil and n-3 polyunsaturated fatty acids (PUFAs) with regard to the development of cardiovascular diseases. The cardioprotective benefits of fish oil have been largely attributed to 20 and 22 carbon fatty acids such as eicosapentaenoic acid (EPA, 20:5n-3) and docosahexanoic acid (DHA, 22:6, n-3) whose enrichment in cells and plasma lipoproteins results in decreased inflammation, thrombosis, blood pressure, arrhythmias, endothelial activation, and plasma triglyceride (TG) concentrations.

Mammals, including humans, can synthesize saturated fatty acids and monounsaturated (n-9) fatty acids but cannot synthesize either the (n-6) or the (n-3) double bond. The (n-3) and (n-6) fatty acids are essential components in cell membrane phospholipids and as a substrate for various enzymes; thus fatty acids containing these bonds are essential fatty acids and must be obtained in the diet. The (n-6) fatty acids are consumed primarily as linoleic acid [18:2(n-6)] from vegetable oils and arachidonic acid [AA, 20:4(n-6)] from meats. The (n-3) fatty acids may be consumed as γ-linolenic acid [GLA, 18:3(n-3)] from some vegetable oils. Longer-chain (n-3) fatty acids, mainly EPA and docosahexaenoic acid [DHA, 22:6(n-3)], are found in fish and fish oils (Hardman, *J. Nutr.* 134: 3427S-3430S (2004)).

In spite of the overwhelming evidence for the beneficial effects of fish oil, the consumption of n-3 PUFAs in the North American population is very low. Since the (n-3)- and (n-6) fatty acids cannot be interconverted in humans, the balance between (n-3) and (n-6) fatty acids in humans can only be achieved through appropriate diets. However, the current Western diet contains predominantly (n-6) fatty acids with a small portion of (n-3) fatty acids. In fact, it is estimated that actual dietary intakes of fatty acid from fish oil are as low as one-tenth of the levels recommended by the American Heart Association (Ursin, *J. Nutr.* 133: 4271-4272 (2003)). Such an imbalance in (n-3) and (n-6) fatty acids has been linked to various diseases, including asthma, cardiovascular diseases, arthritis, cancer.

Research has revealed that (n-3) and (n-6) fatty acids affect the various disease conditions through the action of two types of enzymes: cyclooxygenase (COX) and lipoxygenase (LOX). COX and LOX act on 20-carbon fatty acids to produce cell-signaling molecules. COX activity on AA or EPA produces prostaglandins or thromboxanes; LOX activity on AA or EPA produces the leukotrienes. The 2-series prostaglandins produced from AA tend to be proinflammatory and proliferative in most tissues. The 3-series prostaglandins produced from EPA tend to be less promotional for inflammation and proliferation. Thus, EPA-derived prostaglandins are less favorable for inflammation and for the development and the growth of cancer cells (Hardman, *J. Nutr.* 134: 3427S-3430S (2004)).

An alternative approach to affecting inflammatory diseases has been to supplement diets with the 18-carbon polyunsaturated fatty acid of the (n-6) series, γ-linolenic acid [GLA, 18:3(n-6)]. This fatty acid is found primarily in the oils of the evening primrose and borage plants and to a lesser extent in meats and eggs. Animal data as well as some clinical studies suggest that dietary supplementation with GLA may attenuate the signs and symptoms of 20 chronic inflammatory diseases including rheumatoid arthritis and atopic dermatitis. Echium oil, another botanical oil, which contains stearidonic acid [SDA, 18:4 (n-3)], has been shown to have protective effects in hypertriglyceridemic patients.

However, a major concern in many dietary studies to date is that various sources of the PUFAs, whether it be fish oil, borage, evening primrose or echium oil or combinations of these oils, provide active ingredients (certain PUFAs) that are anti-inflammatory, but they also provide n-6 fatty acids that are potentially pro-inflammatory or that block the anti-inflammatory effects of the active PUFAs. Two such fatty acids are AA and linoleic acid [18:2 (n-6)]. The n-6 fatty acids are consumed primarily as linoleic acid from vegetable oils and AA from meats. Linoleic acid is converted to AA by a series of desaturation and elongation steps. The high amount of dietary linoleic acid is the primary culprit that has resulted in the major imbalance in omega 6 to omega 3 fatty acids observed in western nations. Diets high in linoleic acid have been demonstrated to be pro-inflammatory in several animal models.

Arachidonic acid is a twenty carbon n-6 fatty acid that is converted in mammals to products called leukotrienes, prostaglandins and thromboxanes. These products induce inflammation, and blocking their production utilizing drugs such as aspirin, ibuprofen, celecoxib (Celebrex™), and montelukast sodium (Singulair™) reduces signs and symptoms of inflammatory diseases including asthma and arthritis. In addition to the importance of AA in producing pro-inflammatory products, AA also regulates gene expression in mammals through transcription factors such as peroxisome proliferator-activated receptors (PPAR)-alpha leading to low level whole body inflammation. As indicated above, recent studies reveal that AA is present in high concentrations in many items in our food supply. Ironically, it is found in high concentrations in certain fish. AA in human diets has been correlated with increased levels of pro-inflammatory products, platelet aggregation and atherosclerosis.

SUMMARY OF THE INVENTION

A major advance in the design and development of formulations containing anti-inflammatory fatty acids would be to develop complex oils that contain optimal ratios of anti-inflammatory or anti-cardiovascular disease fatty acids in which non-beneficial or harmful fatty acids are minimized. This may allow for an increase in the dietary intake of anti-inflammatory or anti-cardiovascular disease fatty acids and, thus, allow management and treatment of certain preventable diseases and promote human well-being.

Accordingly, the present invention is directed to processes of making anti-inflammatory fatty acid compositions derived from microalgae. The invention is further directed to the compositions and methods of using the compositions.

In an embodiment, a process of making a polyunsaturated fatty acid composition comprising at least 8% polyunsaturated fatty acids is disclosed; the process comprising: extracting the polyunsaturated fatty acids from a microalgae, wherein (a) GLA is in an amount of 1% to 10% of total fatty acids; (b) SDA is in an amount of 5% to 50% of total fatty acids; (c) EPA is in an amount of 2% to 30% of total fatty acids; and (d) DHA is in an amount of 2% to 30% of total fatty acids; wherein composition comprises at least 8% polyunsaturated fatty acids.

In another embodiment, a process of making a composition comprising at least 5% stearidonic acid is disclosed, the process-comprising: (a) cultivating a microalgae to produce a microalgae biomass; and either (b) extracting said microalgae oil from said microalgae biomass; or (c) removing water from said microalgae biomass to achieve a solids content from about 5 to 100%; wherein the composition comprises at least 5% stearidonic acid.

In yet another embodiment, a process of making an animal feed additive comprising fatty acids from a microalgae is disclosed, the process comprising: (a) cultivating microalgae to produce a microalgae biomass; and either (b) extracting microalgae oil from said microalgae biomass to produce a microalgae oil; or (c) removing water from said microalgae biomass to produce a microalgae biomass with a solids content from about 5% to 100%; wherein the animal feed additive comprises fatty acids from a microalgae.

In a further embodiment, a process of making an animal feed additive comprising at least 8% polyunsaturated fatty acids is disclosed; the process comprising: extracting the fatty acids from a microalgae, wherein (a) GLA is in an amount of 1% to 10% of total fatty acids; (b) SDA is in an amount of 5% to 50% of total fatty acids; (c) EPA is in an amount of 2% to 30% of total fatty acids; and (d) DHA is in an amount of 2% to 30% of total fatty acids, wherein the animal feed additive comprises at least 8% polyunsaturated fatty acids.

In yet a further embodiment, a process of producing an animal having an increased tissue content of long chain omega-3 fatty acids, the method comprising feeding to an animal an animal feed additive comprising fatty acids collected from microalgae, the animal feed additive further comprising: (a) a microalgae oil extracted from a cultivated microalgae biomass and/or (b) a microalgae biomass from a cultivated microalgae, wherein water is removed from microalgae biomass to achieve a solids content from about 5 to 100%; wherein an animal is produced having increased tissue content of long chain omega-3 fatty acids.

In an additional embodiment, a process of producing an animal having an increased tissue content of long chain omega-3 fatty acids is provided, the process comprising feeding to an animal an animal feed additive comprising at least 8% polyunsaturated fatty acids; the animal feed additive comprising fatty acids extracted from a microalgae, wherein (a) GLA is in an amount of 1% to 10% of total fatty acids; (b) SDA is in an amount of 5% to 50% of total fatty acids; (c) EPA is in an amount of 2% to 30% of total fatty acids; and (d) DHA is in an amount of 2% to 30% of total fatty acids; wherein an animal is produced having an increased tissue content of long chain omega-3 fatty acids.

In a subsequent embodiment, a method of treating a mammalian disease in a subject in need thereof by administration to the subject a therapeutically effective amount of a polyunsaturated fatty acid composition comprising at least 8% polyunsaturated fatty acids is provided; the composition further comprising fatty acids extracted from a microalgae, wherein the microalgae fatty acid extract comprises: (a) GLA in an amount of 1% to 10% of total fatty acids; (b) SDA in an amount of 5% to 50% of total fatty acids; (c) EPA in an amount of 2% to 30% of total fatty acids, and (d) DHA in an amount of 2% to 30% of total fatty acids.

In another subsequent embodiment, a method of treating a mammalian disease in a subject in need thereof by administration to the subject a therapeutically effective amount of a composition comprising at least 5% SDA is provided, the composition comprising either (a) a microalgae oil extracted from a cultivated microalgae biomass or (b) a microalgae biomass from a cultivated microalgae, wherein water is removed from microalgae biomass to achieve a solids content from about 5 to 100%.

In a further subsequent embodiment, a polyunsaturated fatty acid composition comprising at least 8% polyunsaturated fatty acids is provided; the composition comprising fatty acids extracted from a microalgae, wherein the microalgae fatty acid extract comprises: (a) GLA in an amount of 1% to 10% of total fatty acids; (b) SDA in an amount of 5% to 50% of total fatty acids; (c) EPA in an amount of 2% to 30% of total fatty acids; and (d) DHA in an amount of 2% to 30% of total fatty acids.

In yet a further subsequent embodiment, a composition comprising at least 5% SDA is provided, the composition comprising either: (a) microalgae oil extracted from a cultivated microalgae biomass or (b) a microalgae biomass from a cultivated microalgae, wherein water is removed from microalgae biomass to achieve a solids content from about 5 to 100%.

In an additional subsequent embodiment, a food product is provided comprising: (a) from 0.01-99.99 percent by weight of a composition comprising at least 8% polyunsaturated fatty acids, wherein the fatty acids are extracted from a microalgae, further wherein the microalgae fatty acid extract comprises: (i) GLA in an amount of 1% to 10% of total fatty acids; (ii) SDA in an amount of 5% to 50% of total fatty acids; (iii) EPA in an amount of 2% to 30% of total fatty acids, and (iv) DHA in an amount of 2% to 30% of total fatty acids; in combination with (b) from 99.99-0.01 percent by weight of at least one additional ingredient selected from the group consisting of proteins, carbohydrates and fiber, and combinations thereof.

Further embodiments of the invention provide a food product comprising: (a) from 0.01-99.99 percent by weight of a composition comprising at least 5% stearidonic acid, the composition comprising either: (i) a microalgae oil extracted from a cultivated microalgae biomass or (ii) a microalgae biomass from a cultivated microalgae, wherein water is removed from microalgae biomass to achieve a solids content from about 5 to 100% weight percent; in combination with (b) from 99.99 to 0.01 percent by weight of at least one additional ingredient selected from the group consisting of proteins, carbohydrates and fiber, and combinations thereof.

In other embodiments of the invention, an animal feed additive is provided wherein the animal feed additive comprises fatty acids collected from microalgae either in the form of: a) a microalgae oil extracted from a cultivated microalgae biomass or (b) a microalgae biomass from a cultivated microalgae, wherein water is removed from microalgae biomass to achieve a solids content from about 5 to 100% weight percent.

Additionally provided herein is an animal feed additive comprising at least 8% polyunsaturated fatty acids; the additive comprising fatty acids extracted from a microalgae, wherein the microalgae fatty acid extract further comprises: (a) GLA in an amount of 1% to 10% of total fatty acids; (b) SDA in an amount of 5% to 50% of total fatty acids; (c) EPA in an amount of 2% to 30% of total fatty acids; and (d) DHA in an amount of 2% to 30% of total fatty acids.

An other embodiment of the invention includes an animal product produced by feeding to an animal an animal feed additive comprising fatty acids collected from microalgae either in the form of: (a) a microalgae oil extracted from a cultivated microalgae biomass or (b) a microalgae biomass from a cultivated microalgae, wherein water is removed from microalgae biomass to achieve a solids content from about 5 to 100% weight percent.

Still other embodiments of the invention provide an animal product produced by feeding to an animal an animal feed additive comprising at least 8% polyunsaturated fatty acids; the additive comprising fatty acids extracted from a microalgae, wherein the microalgae fatty acid extract further comprises (a) GLA in an amount of 1% to 10% of total fatty acids; (b) SDA in an amount of 5% to 50% of total fatty acids; (c) EPA in an amount of 2% to 30% of total fatty acids, and (d) DHA in an amount of 2% to 30% of total fatty acids.

In one aspect, the present invention provides a method for preparing a microalgae biomass comprising one or more PUFAs. The method comprises:
culturing a microalgae under a culture condition sufficient to provide a microalgae biomass comprising the one or more PUFAs, wherein the microalgae biomass is harvested at a logarithmic growth phase of the microalgae.

In another aspect, the present invention provides a method for preparing a microalgae biomass comprising one or more PUFAs, the method comprising:
culturing a microalgae under a culture condition sufficient to provide a microalgae biomass comprising the one or more PUFAs, wherein the microalgae biomass is harvested at a logarithmic growth phase of the microalgae, wherein the omega-3 fatty acid is stearidonic acid (SDA), wherein the omega-6 fatty acid is γ-linolenic acid (GLA), wherein the SDA at harvest is at least about 30% of the total fatty acid, wherein the GLA at harvest is less than about 1% of total fatty acid.

In some aspects, the present invention provides a lipid composition prepared from a microalgae biomass, wherein the lipid composition, upon extraction from the microalgae biomass, comprises:
(a) a microalgae-produced SDA in a total SDA amount of at least 10% of the total fatty acids; and
(b) a microalgae-produced GLA in a total GLA amount of less than about 5% of the total fatty acids.

In other aspects, the present invention provides a microalgae biomass comprising lipids having at least 30% by weight of total fatty acids as omega-3 fatty acids.

In one aspect, the present invention provides a microalgae biomass comprising lipids having at least 40% by weight of total fatty acids as omega-3 and omega-6 fatty acids.

In another aspect, a microalgae biomass comprising an omega-3 fatty acid content of at least 10% dry weight of the biomass is provided.

In one aspect, the present invention provides a method for preparing a microalgae biomass comprising one or more PUFAs, the method comprising:
culturing a micro algae under a culture condition sufficient to provide a microalgae biomass comprising the one or more PUFAs, wherein the microalgae biomass is harvested at a negative growth acceleration phase or a stationary phase of the microalgae.

In still other aspects, the present invention provides a lipid composition prepared from a microalgae biomass, wherein the lipid composition, upon extraction from the microalgae biomass, comprises:
(a) a microalgae-produced SDA in a total SDA amount of at least 5% of the total fatty acids; and
(b) a microalgae-produced GLA in a total GLA amount of at least 5% of the total fatty acids.

In one aspect, the present invention provides isolated *Rhodomonas* strains, ATCC Nos. PTA-9986, PTA-9987, PTA-9988, PTA-9989, and PTA-9990, which were deposited on Apr. 30, 2009.

In other aspects, the present invention provides a biologically pure culture of isolated *Rhodomonas* strains, ATCC Nos.: PTA-9986, PTA-9987, PTA-9988, PTA-9989, and PTA-9990, which were deposited on Apr. 30, 2009.

In some aspects, the present invention provides a kit comprising a microalgae biomass, lipid composition, and/or fraction thereof prepared in accordance with the present invention.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

BRIEF DESCRIPTION OF THE DRAWINGS

FIG. 20 shows SDA content of *Rhodomonas* strains as function of time in culture grown in the presence of normal (N; ~36 μM) or low (L; ~18 μM) phosphate.

FIG. 23 shows FA content (A-D) and cell numbers (E) in antibiotic treated strain 12Rsp in relation to medium phosphate concentration in the presence of normal (N; ~36 μM) or low (L; ~18 μM) phosphate. Also shown is cell numbers (F) in relation to medium nitrate concentration in the presence of normal (N; ~36 μM) or low (L; ~18 μM) phosphate. The cell density (dashed curves) is shown in each panel.

FIG. 24 shows FA content (A-D) and cell numbers (E) in strain 4Rsal in relation to medium phosphate concentration in the presence of normal (N; ~36 μM) or low (L; ~18 μM) phosphate. Also shown is cell numbers (F) in relation to medium nitrate concentration in the presence of normal (N; ~36 μM) or low (L; ~18 μM) phosphate. The cell density (dashed curves) is shown in each panel.

FIG. 25 shows FA content (A-D) and cell numbers (E) in strain 5Rsal in relation to medium phosphate concentration in the presence of normal (N; ~36 μM) or low (L; ~18 μM) phosphate. Also shown is cell numbers (F) in relation to medium nitrate concentration in the presence of normal (N; ~36 μM) or low (L; ~18 μM) phosphate. The cell density (dashed curves) is shown in each panel.

FIG. 26 shows FA content (A-D) and cell numbers (E) in strain 16Rsp in relation to medium phosphate concentration in the presence of normal (N; ~36 μM) or low (L; ~18 μM) phosphate. Also shown is cell numbers (F) in relation to medium nitrate concentration in the presence of normal (N; ~36 μM) or low (L; ~18 μM) phosphate. The cell density (dashed curves) is shown in each panel.

FIG. 27 shows the FA profiles (solid curves) of strain 12Rsp in the presence of normal (N; ~36 μM) or low (L; ~18 μM) phosphate. The cell density (dashed curves) is shown in each panel.

FIG. 28 shows the FA profiles (solid curves) of strain 4Rsal in the presence of normal (N; ~36 μM) or low (L; ~18 μM) phosphate. The cell density (dashed curves) is shown in each panel.

FIG. 29 shows the FA profiles (solid curves) of strain 5Rsal in the presence of normal (N; ~36 μM) or low (L; ~14 μM) phosphate. The cell density (dashed curves) is shown in each panel.

FIG. 30 shows the FA profile (solid curves) of strain 16Rsp in the presence of normal (N; ~36 μM) or low (L; ~18 μM) phosphate. The cell density (dashed curves) is shown in each panel.

DETAILED DESCRIPTION

Figure 1:
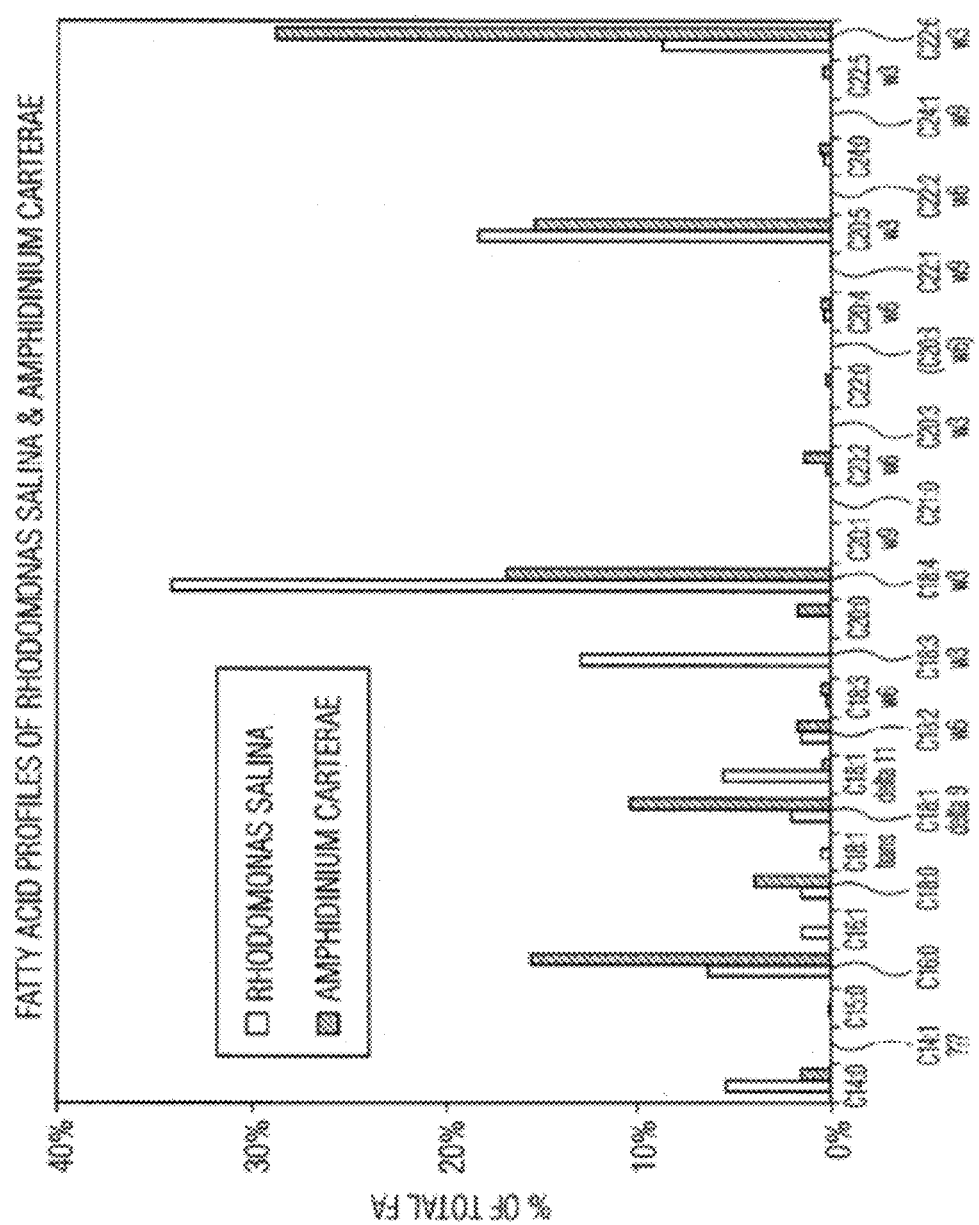
FIG. 1 shows the fatty acid profiles of *Rhodomonas salina* and *Amphidinium carterae*.

As used herein, the phrase "therapeutically effective amount" refers to an amount of a compound or composition that is sufficient to produce the desired effect, which can be a therapeutic or agricultural effect. The therapeutically effective amount will vary with the application for which the compound or composition is being employed, the microorganism and/or the age and physical condition of the subject, the severity of the condition, the duration of the treatment, the nature of any concurrent treatment, the pharmaceutically or agriculturally acceptable carrier used, and like factors within the knowledge and expertise of those skilled in the art. An appropriate "therapeutically effective amount" in any individual case can be determined by one of ordinary skill in the art by reference to the pertinent texts and literature and/or by using routine experimentation. (See, for example for pharmaceutical applications, Remington, *The Science And Practice of Pharmacy* (9th Ed. 1995).

Disclosed is a novel process for producing polyunsaturated fatty acids, and a novel composition of polyunsaturated fatty acids derived from microalgae.

Generally, the process of making a polyunsaturated fatty acid composition comprising at least 8% polyunsaturated fatty acids comprises: extracting at least one fatty acid from a microalgae, wherein (a) GLA is in an amount of 0.1% to 10% of total fatty acids; (b) SDA is in an amount of 5% to 50% of total fatty acids; (c) EPA is in an amount of 2% to 30% of total fatty acids, and (d) DHA is in an amount of 2% to 30% of total fatty acids, wherein the composition comprises at least 8% polyunsaturated fatty acids.

In one embodiment, the microalgae can be a mixture of different microalgae species. In some embodiments, one of the fatty acids, GLA, SDA, EPA or DHA, is not included in the composition. In other aspects of the invention the polyunsaturated fatty acid composition is supplemented with polyunsaturated fatty acids from other sources including, but not limited to plant sources. Plant sources of polyunsaturated fatty acids include, but are not limited to, borage, black currant, echium and primrose.

In some embodiments, the polyunsaturated fatty acid composition produced by the process of the invention can comprise polyunsaturated fatty acids at a concentration in a range from 5% to 35%. Thus, the polyunsaturated fatty acid composition can comprise polyunsaturated fatty acids at a concentration of 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, and the like. In other embodiments, the polyunsaturated fatty acid composition can comprise polyunsaturated fatty acids in a range from 5% to 7%, 5% to 8%, 5% to 10%, 5% to 12%, 5% to 15%, 5% to 20%, 5% to 25%, 5% to 30%, 6% to 8%, 6% to 10%, 6% to 12%, 6% to 15%, 6% to 20%, 6% to 25%, 6% to 35%, 7% to 9%, 7% to 11%, 7% to 13%, 7% to 14%, 7% to 15%, 7% to 20%, 7% to 25%, 7% to 30%, 7% to 35%, 8% to 10%, 8% to 12%, 8% to 14%, 8% to 15%, 8% to 20%, 8% to 25%, 8% to 35%, 9% to 11%, 9% to 13%, 9% to 15%, 9% to 20%, 9% to 25%, 9% to 30%, 9% to 35%, 10% to 12%, 10% to 13%, 10% to 14%, 10% to 15%, 10% to 20%, 10% to 25%, 10% to 30%, 10% to 35%, 15% to 20%, 15% to 25%, 15% to 30%, 20% to 25%, 20% to 30%, 20% to 35%, 25% to 30%, 25% to 35%, 30% to 35%, and the like. In one embodiment, the polyunsaturated fatty acid composition comprises polyunsaturated fatty acids at a concentration of at least 8%.

In other embodiments, the amount of GLA that can be included in the composition is in a range from 0.1% to 10% of total fatty acids. Thus, the GLA can be included in the composition in an amount of total fatty acids of 0.1%, 0.2%, 0.3%, 0.4%, 0.5%, 0.6%, 0.7%, 0.8%, 0.9%, 1.0%, 2%, 3%, 4%, 5%, 6%, 7%, 8%, 9%, 10%, and the like. In other embodiments, the GLA can be included in the composition in an amount of total fatty acids in a range from 0.1% to 1%, 1% to 3%, 1% to 5%, 1% to 7%, 1% to 9%, 2% to 4%, 2% to 6%, 2% to 8%, 2% to 10%, 3% to 5%, 3% to 7%, 3% to 9%, 3% to 10%, 4% to 6%, 4% to 8%, 4% to 10%, 5% to 7%, 5% to 8%, 5% to 9%, 5% to 10%, 6% to 8%, 6% to 9%, 6% to 10%, 7% to 9%, 7% to 10%, 8% to 10%, 9% to 10%, and the like.

In some embodiments, the amount of SDA that is included in the composition of the present invention is in a range from 5% to 50% of total fatty acids. Thus, the SDA can be provided in the composition in an amount of total fatty acids of 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, and the like. In other embodiments, the SDA can be included in the composition in an amount of total fatty acids in a range from 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 5 10% to 45%, 10% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, 45% to 50%, and the like.

In other embodiments, the EPA can be included in the composition in a range from 2% to 30% of total fatty acids. Thus, the EPA can be provided in the composition in an amount of total fatty acids of 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, and the like. In other embodiments, the EPA can be included in the composition in an amount of percent of total fatty acids in a range from 1% to 5%, 1% to 10%, 1% to 15%, 1% 15 to 20%, 1% to 25%, 1% to 30%, 5% to 10%, 5% to 15%, 5% to 20%, 5% to 25%, 5% to 30%, 10% to 15%, 10% to 20%, 10% to 25%, 10% to 30%, 15% to 20%, 15% to 25%, 15% to 30%, 20% to 25%, 20% to 30%, 25% to 30%, and the like.

In some embodiments of the present invention, the DHA can be included in the composition in a range from 2% to 30% of total fatty acids. Thus, the DHA can be provided 20 in the composition in an amount of total fatty acids of 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, and the like. In other embodiments, the DHA can be included in the composition in an amount of total fatty acids in a range from 1% to 5%, 1% to 10%, 1% to 15%, 1% to 20%, 1% to 25%, 1% to 30%, 5% to 10%, 5% to 15%, 5% to 20%, 5% to 25%, 5% to 30%, 10% to 15%, 10% to 20%, 10% to 25%, 10% to 30%, 15% to 20%, 15% to 25%, 15% to 30%, 20% to 25%, 20% to 30%, 25% to 30%, and the like.

Other aspects of the invention provide a process of making a composition comprising at least 5% SDA, the process comprising: (a) cultivating a microalgae to produce a microalgae biomass; and either (b) extracting said microalgae oil from said microalgae biomass; or (c) removing water from said microalgae biomass to achieve a solids content from about 5 to 100% weight percent; wherein a composition is produced comprising at least 5% stearidonic acid.

In some embodiments, the SDA is in a triglyceride form. In other embodiments, the SDA is not in a phospholipid form.

In some embodiments, the SDA is present in the composition in an amount in a range from 2% to 10%. Thus, the SDA is present in the composition in an amount of 2%, 3%, 4%, 5%, 6%, 7%, 8%, 9%, 10%, and the like. In other embodiments, the SDA can be included in the composition in a range from 2% to 4%, 2% to 6%, 2% to 8%, 2% to 10%, 3% to 5%, 3% to 7%, 3% to 9%, 3% to 10%, 4% to 6%, 4% to 8%, 4% to 10%, 5% to 7%, 5% to 8%, 5% to 9%, 5% to 10%, 6% to 8%, 6% to 9%, 6% to 10%, 7% to 9%, 7% to 10%, 8% to 10%, 9% to 10%, and the like.

Additional embodiments of the invention include processes of making animal feed additives. Thus, one aspect of the present invention is a process of making an animal feed additive comprising polyunsaturated fatty acids from a microalgae, the process comprising: (a) cultivating microalgae to produce a microalgae biomass; and either (b) extracting microalgae oil from said microalgae biomass to produce a microalgae oil; or (c) removing water from said microalgae biomass to produce a microalgae biomass with a solids content from about 5% to 100% weight percent; wherein the animal feed additive comprises polyunsaturated fatty acids from microalgae.

In some embodiments, the fatty acids collected from the microalgae are short chain omega-3 fatty acids. Medium chain omega-3 fatty acids include but are not limited to SDA and alpha linolenic acid (ALA).

In further embodiments, the microalgae oil extracted from the microalgae biomass can be combined with a microalgae biomass with a solids content from about 5% to 100% weight percent.

An additional aspect of the invention provides a process of making an animal feed additive comprising at least 8% polyunsaturated fatty acids; the process comprising: extracting the fatty acids from a microalgae, wherein the fatty acids may include (a) GLA is in an amount of 0.1% to 10% of total fatty acids; (b) SDA is in an amount of 5% to 50% of total fatty acids; (c) EPA is in an amount of 2% to 30% of total fatty acids; and (d) DHA is in an amount of 2% to 30% of total fatty acids; wherein the animal feed additive comprises at least 8% polyunsaturated fatty acids.

In some embodiments, the animal feed additive produced by the process of the invention can comprise polyunsaturated fatty acids at a concentration in a range of 5% to 35%. Thus, the animal feed additive can comprise polyunsaturated fatty acids at a concentration of 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, and the like. In other embodiments, the animal feed additive can comprise polyunsaturated fatty acids at a concentration in a range from 5% to 7%, 5% to 8%, 5% to 10%, 5% to 12%, 5% to 15%, 5% to 20%, 5% to 25%, 5% to 30%, 6% to 8%, 6% to 10%, 6% to 12%, 6% to 15%, 6% to 20%, 6% to 25%, 6% to 35%, 7% to 9%, 7% to 11%, 7% to 13%, 7% to 14%, 7% to 15%, 7% to 20%, 7% to 25%, 7% to 30%, 7% to 35%, 8% to 10%, 8% to 12%, 8% to 14%, 8% to 15%, 8% to 20%, 8% to 25%, 8% to 35%, 9% to 11%, 9% to 13%, 9% to 15%, 9% to 20%, 9% to 25%, 9% to 30%, 9% to 35%, 10% to 12%, 10% to 13%, 10% to 14%, 10% to 15%, 10% to 20%, 10% to 25%, 10% to 30%, 10% to 35%, 15% to 20%, 15% to 25%, 15% to 30%, 20% to 25%, 20% to 30%, 20% to 35%, 25% to 30%, 25% to 35%, 30% to 35%, and the like. In one embodiment, the animal feed additive comprises polyunsaturated fatty acids at a concentration of at least 8%.

In further embodiments, the amount of GLA that can be included in the animal feed additive is in a range from 0.1% to 10% of total fatty acids. Thus, the GLA can be included in the animal feed additive in an amount of total fatty acids of 0.1%, 0.2%, 0.3%, 0.4%, 0.5%, 0.6%, 0.7%, 0.8%, 0.9%, 1.0%, 2%, 3%, 4%, 5%, 6%, 7%, 8%, 9%, 10% and the like. In other embodiments, the GLA can be included in the animal feed additive in an amount of total fatty acids in a range from 0.1% to 1%, 1% to 3%, 1% to 5%, 1% to 7%, 1% to 9%, 2% to 4%, 2% to 6%, 2% to 8%, 2% to 10%, 3% to 5%, 3% to 7%, 3% to 9%, 3% to 10%, 4% to 6%, 4% to 8%, 4% to 10%, 5% to 7%, 5% to 8%, 5% to 9%, 5% to 10%, 6% to 8%, 6% to 9%, 6% to 10%, 7% to 9%, 7% to 10%, 8% to 10%, 9% to 10%, and the like.

In still further embodiments, the amount of SDA that is included in the animal feed additive of the present invention is in a range from 5% to 50% of total fatty acids. Thus, the animal feed additive can comprise SDA in an amount of total fatty acids of 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, and the like. In other embodiments, the SDA can be included in the animal feed additive in an amount of total fatty acids in a range from 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, 45% to 50%, and the like.

In other embodiments, the EPA can be included in the animal feed additive in a range from 2% to 30% of total fatty acids. Thus, the EPA can be provided in the animal feed additive in an amount of total fatty acids of 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, and the like. In other embodiments, the EPA can be included in the animal feed additive in an amount of percent of total fatty acids in a range from 1% to 5%, 1% to 10%, 1% to 15%, 1% to 20%, 1% to 25%, 1% to 30%, 5% to 10%, 5% to 15%, 5% to 20%, 5% to 25%, 5% to 30%, 10% to 15%, 10% to 20%, 10% to 25%, 10% to 30%, 15% to 20%, 15% to 25%, 15% to 30%, 20% to 25%, 20% to 30%, 25% to 30%, and the like.

In some embodiments of the present invention, the DHA can be included of the animal feed additive in a range from 2% to 30% of total fatty acids. Thus, the DHA can be provided in the animal feed additive in an amount of total fatty acids of 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, and the like. In other embodiments, the DHA can be included in the animal feed additive in an amount of total fatty acids in a range from 1% to 5%, 1% to 10%, 1% to 15%, 1% to 20%, 1% to 25%, 1% to 30%, 5% to 10%, 5% to 15%, 5% to 20%, 5% to 25%, 5% to 30%, 10% to 15%, 10% to 20%, 10% to 25%, 10% to 30%, 15% to 20%, 15% to 25%, 15% to 30%, 20% to 25%, 20% to 30%, 25% to 30%, and the like.

Further embodiments of the present invention provide a process of making an animal feed additive comprising at least 5% SDA, the process comprising: (a) cultivating a microalgae to produce a microalgae biomass; and either (b) extracting said microalgae oil from said microalgae biomass; or (c) removing water from said microalgae biomass to achieve a solids content from about 5 to 100% weight percent; wherein an animal feed additive is produced comprising at least 5% SDA.

In some embodiments, the SDA produced by the process of the invention is present in the composition in an amount in a range from 2% to 10%. Thus, the SDA is present in the composition in an amount of 2%, 3%, 4%, 5%, 6%, 7%, 8%, 9%, 10%, and the like. In other embodiments, the SDA can be included in the composition in a range from 2% to 4%, 2% to 6%, 2% to 8%, 2% to 10%, 3% to 5%, 3% to 7%, 3% to 9%, 3% to 10%, 4% to 6%, 4% to 8%, 4% to 10%, 5% to 7%, 5% to 8%, 5% to 9%, 5% to 10%, 6% to 8%, 6% to 9%, 6% to 10%, 7% to 9%, 7% to 10%, 8% to 10%, 9% to 10%, and the like.

A feed additive according to the present invention can be combined with other food components to produce processed animal feed products. Such other food components include one or more enzyme supplements, vitamin food additives and mineral food additives. The resulting (combined) feed additive, including possibly several different types of compounds can then be mixed in an appropriate amount with the other food components such as cereal and plant proteins to form a processed food product. Processing of these components into a processed food product can be performed using any of the currently used processing apparatuses. The animal feed additives of the present invention may be used as a supplement in animal feed by itself, in addition with vitamins, minerals, other feed enzymes, agricultural co-products (e.g., wheat middlings or corn gluten meal), or in a combination therewith.

Additional embodiments of the invention provide processes of producing an animal having increased tissue content of long chain omega-3 fatty acids, the process comprising feeding to an animal an animal feed additive described herein. The increase in tissue content of long chain omega-3 fatty acids is relative to that of an animal not fed the animal feed additives of the present invention.

Thus, one aspect of the present invention provides a process of producing an animal having an increased tissue content of long chain omega-3 fatty acids, the process comprising feeding to an animal an animal feed additive comprising fatty acids collected from microalgae, the animal feed additive further comprising: (a) a microalgae oil extracted from a cultivated microalgae biomass and/or (b) a microalgae biomass from a cultivated microalgae, wherein water is removed from microalgae biomass to achieve a solids content from about 5 to 100% weight percent, wherein an animal is produced having an increased tissue content of long chain omega-3 fatty acids.

In some embodiments, a process of producing an animal having an increased tissue content of long chain omega-3 fatty acids is provided, the process comprising feeding to an animal an animal feed additive comprising at least 8% polyunsaturated fatty acids; the animal feed additive comprising fatty acids extracted from a microalgae, wherein the fatty acids can be (a) GLA in an amount of 0.1% to 10% of total fatty acids; (b) SDA in an amount of 5% to 50% of total fatty acids; (c) EPA in an amount of 2% to 30% of total fatty acids; and (d) DHA in an amount of 2% to 30% of total fatty acids; wherein an animal is produced having an increased tissue content of long chain omega-3 fatty acids.

In other embodiments, a process of producing an animal having an increased tissue content of long chain omega-3 fatty acids is provided, the process comprising feeding to an animal an animal feed additive comprising at least 5% SDA, the animal feed additive comprising either (a) a microalgae oil extracted from a cultivated microalgae biomass or (b) a microalgae biomass from a cultivated microalgae, wherein water is removed from microalgae biomass of (b) to achieve a solids content from about 5 to 100% weight percent.

An animal of the present invention includes, but is not limited to, any animal whose eggs, meat, milk or other products are consumed by humans or other animals. Thus, animals of the invention include, but are not limited to, fish, poultry (chickens, turkeys, ducks, etc.), pigs, sheep, goats, rabbits, beef and dairy cattle. The term "tissue content" as used herein refers to the various parts of the animal body, including but not limited to muscle, bone, skin, hair, and blood.

The present invention additionally provides methods for treating a mammalian disease in a subject in need thereof by administration to said subject a therapeutically effective amount of the compositions of the present invention. In some embodiments, the mammalian diseases that are treated include, but are not limited to, cardiovascular diseases, inflammatory diseases, and various cancer diseases. In other embodiments, the cardiovascular diseases to be treated include, but are not limited to, hypertriglyceridemia, coronary heart disease, stroke, acute myocardial infarction and atherosclerosis. In further embodiments, the inflammatory diseases to be treated include, but are not limited to, asthma, arthritis, allergic rhinitis, psoriasis, atopic dermatitis, inflammatory bowel diseases, Crohn's disease, and allergic rhinoconjunctitis. In still further embodiments, the cancer diseases to be treated include, but are not limited to, prostate cancer, breast cancer and colon cancer. In additional embodiments, the mammalian diseases to be treated include psychiatric disorders. Psychiatric disorders include, but are not limited to, depression, bipolar disorder, schizophrenia. In addition, the compositions of the invention can be used to maintain and/or enhance cognitive function.

Another embodiment of the present invention provides a method of treating a mammalian disease in a subject in need thereof by administration to the subject a therapeutically effective amount of a polyunsaturated fatty acid composition comprising at least 8% polyunsaturated fatty acids extracted from a microalgae, wherein the fatty acids can be (a) GLA in an amount of 0.1% to 10% of total fatty acids; (b) SDA in an amount of 5% to 50% of total fatty acids; (c) EPA in an amount of 2% to 30% of total fatty acids, and (d) DHA in an amount of 2% to 30% of total fatty acids. Further details on the amounts and ranges of polyunsaturated fatty acids, GLA, SDA, EPA and DHA in the compositions are as described above in the descriptions of the compositions.

An additional aspect of the invention provides a method of treating a mammalian disease in a subject in need thereof by administration to the subject a therapeutically effective amount of a composition comprising at least 5% SDA, the composition comprising either (a) a microalgae oil extracted from a cultivated microalgae biomass or (b) a microalgae biomass from a cultivated microalgae, wherein water is removed from microalgae biomass of (b) to achieve a solids content from about 5 to 100% weight percent. In some other embodiments, the microalgae oil and the microalgae biomass can be combined in the composition comprising 5% SDA. Further details on the amounts and ranges of SDA in the compositions are as described above in the descriptions of the compositions.

Subjects suitable to be treated according to the present invention include, but are not limited to, avian and mammalian subjects. Illustrative avians according to the present invention include chickens, ducks, turkeys, geese, quail, pheasant, ratites (e.g., ostrich), domesticated birds (e.g., parrots and canaries), and birds in ovo. Mammals of the present invention include, but are not limited to, canines, felines, bovines, caprines, equines, ovines, porcines, rodents (e.g. rats and mice), lagomorphs, primates (including non-human primates), humans, and the like, and mammals in utero. Any mammalian subject in need of being treated according to the present invention is suitable. According to some embodiments of the present invention, the mammal is a non-human mammal. In some embodiments, the mammal is a human subject. Mammalian subjects of both genders and at any stage of development (i.e., neonate, infant, juvenile, adolescent, adult) can be treated according to the present invention.

Microalgae Any microalgae capable of producing a microalgae oil or microalgae biomass containing at least one polyunsaturated fatty acid from GLA, SDA, EPA, and DHA can be used in the processes, compositions, dietary supplements, and feed additives of the present invention. Thus, in some embodiments, the microalgae of the present invention is selected from the group consisting of Dinophyceae, Cryptophyceae, Trebouxiophyceae, Pinguiophyceae, and combinations thereof. In other embodiments, the microalgae of the invention are selected from the group consisting of *Parietochloris* spp., *Rhodomonas* spp., *Cryptomonas* spp., *Parietochloris* spp., *Hemisebnis* spp.; *Porphyridium* spp., *Glossomastix* spp., and combinations thereof. In further embodiments, the microalgae of the invention are selected from the group consisting of *Parietochloris incise, Rhodomonas salina, Hemiselmis brunescens, Porphyridium cruentum* and *Glossomastix chrysoplasta*, and combinations thereof. In still further embodiments, the microalgae of the invention is *Rhodomonas salina*.

In some embodiments of the invention, the microalgae can be a mixture of different microalgae species. In other embodiments, the microalgae is a single microalgae species. In some embodiments of the present invention, the microalgae fatty acids are provided as a microalgae oil. In other embodiments, the microalgae fatty acids are provided as a microalgae biomass.

Further, the microalgae of the invention include, but are not limited to, wild-type, mutant (naturally or induced) or genetically engineered microalgae.

Additionally, the microalgae of the present invention includes microalgae having cells with cell walls of reduced thickness as compared to the cells of wild-type microalgae, whereby the cell wall of reduced thickness improves extractability and/or bioavailability of the microalgae lipid fraction (e.g., improving the ease of digestibility of the microalgae and the ease of extractability of the microalgae oils from the cells of the microalgae biomass). Microalgae having cells with cell walls of reduced thickness as compared to the cells of wild-type microalgae can be naturally occurring, mutated and/or genetically engineered to have cell walls of reduced thickness as compared to wild-type strains. Thus, in one embodiment of the invention the microalgae is a microalgae having a cell wall of reduced thickness as compared to the wild-type microalgae, whereby said cell wall of reduced thickness improves extractability and/or bioavailability of the microalgae lipid fraction.

Methods of producing microalgae with reduced cell walls include those found in WO 2006/107736 A1, herein incorporated by reference in its entirety. Thus, the microalgae can be mutagenized with mutagens known to those of skill in the art including, but not limited to, chemical agents or radiation. In particular embodiments the chemical mutagens include, but are not limited to, ethyl methanesulfonate (EMS), methylmethane sulfonate (MMS), N-ethyl-N-nitrosourea (ENU), triethylmelamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine (MNNG), nitrosoguanidine, 2-aminopurine, 7,12 dimethyl-benz(a)anthracene (DMBA), ethylene oxide, hexamethylphosphoramide, bisulfan, diepoxyalkanes (diepoxyoctane (DEO), diepoxybutane (BEB), and the like), 2-methoxy-6-chloro-9[3-(ethyl-2-chlor-o-ethypaminopropylamino]acridine dihydrochloride (ICR-170), formaldehyde, and the like. Methods of radiation mutagenesis include, but are not limited to, x-rays, gamma-radiation, ultra-violet light, and the like.

Cell wall mutants can be selected for on the basis of increased sensitivity to detergents or by microscopic observation of alterations in cell wall thickness (WO 2006/107736 A1) or any other method known in the art to detect reduced cell wall thickness or reduced cell wall integrity.

The microalgae of the present invention can be cultured according to techniques described below in Example 1. In addition, the microalgae of the present invention can be cultured according to techniques known in the art including those techniques described by U.S. Pat. No. 5,244,921; U.S. Pat. No. 5,324,658; U.S. Pat. No. 5,338,673; U.S. Pat. No. 5,407,957; Mansour et al., J. Appl. Phycol. 17: 287-300 (2005); and Bigogno et al., Phytochemistry, 60: 497-503 (2002), the disclosures of which are to be incorporated by reference herein in their entirety.

Accordingly, in some embodiments the microalgae are cultured at a temperature in a range from 10° C. to 25° C. Thus, the microalgae can be cultured at a temperature of 10° C., 11° C., 12° C., 13° C., 14° C., 15° C., 16° C., 17° C., 18° C., 19° C., 20° C., 21° C., 22° C., 23° C., 24° C., 25° C., and the like. In other embodiments, the microalgae can be grown in ranges from 10° C. to 15° C., 10° C. to 20° C., 10° C. to 25° C., 12° C. to 15° C., 12° C. to 17° C., 12° C. to 20° C., 12° C. to 22° C., 12° C. to 24° C., 14° C. to 17° C., 14° C. to 19° C., 14° C. to 22° C., 14° C. to 25° C., 15° C. to 18° C., 15° C. to 20° C., 15° C. to 23° C., 15° C. to 25° C., 16° C. to 18° C., 16° C. to 19° C., 16° C. to 21° C., 16° C. to 23° C., 16° C. to 25° C., 17° C. to 19° C., 17° C. to 20° C., 17° C. to 23° C., 17° C. to 25° C., 18° C. to 20° C., 18° C. to 22° C., 18° C. to 23° C., 18° C. to 25° C., 19° C. to 21° C., 19° C. to 23° C., 19° C. to 25° C., 20° C. to 23° C., 20° C. to 25° C., 23° C. to 25° C., and the like. In a particular embodiment, the microalgae are grown at 14° C. In another embodiment, the microalgae are grown at 22° C.

In some embodiment, the microalgae are cultured at a light intensity in a range from 75 $\mu mol\ m^{-2}\ s^{-1}$ to 150 $\mu mol\ m^{-2}\ s^{-1}$. Accordingly, the microalgae can be grown at a light intensity of 75, 80, 85, 90, 95, 100, 105, 110, 115, 120, –125, 130, 135, 140, 145, 150} $\mu mol\ m^{-2}\ s^{-1}$. In other embodiments, the microalgae can be grown at a light intensity in a range from 75 to 85 $\mu mol\ m^{-2}\ s^{-1}$, 75 to 95 $\mu mol\ m^{-2}\ s^{-1}$, 75 to 105 $\mu mol\ m^{-2}\ s^{-1}$, 75 to 115 $\mu mol\ m^{-2}\ s^{-1}$, 75 to 125 $\mu mol\ m^{-2}\ s^{-1}$, 75 to 135 $\mu mol\ m^{-2}\ s^{-1}$, 75 to 150 $\mu mol\ m^{-2}\ s^{-1}$, 85 to 100 $\mu mol\ m^{-2}\ s^{-1}$, 85 to 115 $\mu mol\ m^{-2}\ s^{-1}$, 85 to 130 $\mu mol\ m^{-2}\ s^{-1}$, 85 to 150 $\mu mol\ m^{-2}\ s^{-1}$, 95 to 115 $\mu mol\ m^{-2}\ s^{-1}$, 95 to 125 $\mu mol\ m^{-2}\ s^{-1}$, 95 to 135 $\mu mol\ m^{-2}\ s^{-1}$, 95 to 150 $\mu mol\ m^{-2}\ s^{-1}$, 100 to 115 $\mu mol\ m^{-2}\ s^{-1}$, 100 to 125 $\mu mol\ m^{-2}\ s^{-1}$, 100 to 140 $\mu mol\ m^{-2}\ s^{-1}$, 100 to 150 $\mu mol\ m^{-2}\ s^{-1}$, 110 to 125 $\mu mol\ m^{-2}\ s^{-1}$, 110 to 135 $\mu mol\ m^{-2}\ s^{-1}$, 110 to 150 $\mu mol\ m^{-2}\ s^{-1}$, 120 to 130 $\mu mol\ m^{-2}\ s^{-1}$, 120 to 140 $\mu mol\ m^{-2}\ s^{-1}$, 120 to 150 $\mu mol\ m^{-2}\ s^{-1}$, 130 to 140 $\mu mol\ m^{-2}\ s^{-1}$, 130 to 150 $\mu mol\ m^{-2}\ s^{-1}$, 140 to 150 $mol\ m^{-2}\ s^{-1}$, and the like. In a particular embodiment, the microalgae are cultivated at a light intensity of 100 $\mu mol\ m^{-2}\ s^{-1}$.

Following cultivation of the microalgae to the desired density, the microalgae are harvested using conventional procedures known to those of skill in the art and may include centrifugation, flocculation or filtration. The harvested microalgae cells or microalgae biomass can then be used directly as a fatty acid source or extracted to obtain microalgae oil comprising the fatty acids. In some embodiments in which the microalgae biomass is to be used directly, water is removed from the microalgae biomass to achieve a solids content from about 5 to 100 weight percent. In additional embodiments, a microalgae biomass that is to be used directly is comprised of microalgae cells further comprising cell walls that are at least partially disrupted to increase the extractability and/or bioavailability of the microalgae oil within the cells. The disruption of the microalgae cells can be carried out according to conventional techniques including, but not limited to, treating the cells with boiling water or by mechanical breaking such as grinding, pulverizing, sonication or the French press, or any other method known to those of skill in the art.

As stated above, in some embodiments, when the microalgae biomass is to be used directly, water is removed from the microalgae biomass to achieve a solids content from about 5 to 100%. Accordingly, water is removed from the microalgae biomass to achieve a solids content of 5%, 10%, 15%, 20%, 25%, 30%, 35%, 40%, 45%, 50%, 55%, 60%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, and the like. In additional embodiments, water is removed from the microalgae biomass to achieve a solids content in the range from about 5% to 50%, 5% to 60%, 5% to 70%, 5% to 80%, 5% to 90%, 5% to 95%, 10% to 30%, 10% to 40%, 10% to 50%, 10% to 60% 10% to 65%, 10% to 70%, 10% to 75%, 10% to 80%, 10% to 85%, 10% to 90%, 10% to 95%, 10% to 100%, 15% to 40%, 15% to 50%, 15% to 60%, 15% to 65%, 15% to 70%, 15% to 75%, 15% to 80%, 15% to 85%, 15% to 90%, 15% to 95%, 15% to 100%, 20% to 50%, 20% to 60%, 20% to 65%, 20% to 70%, 20% to 75%, 20% to 80%, 20% to 85%, 20% to 90%, 20% to 95%, 20% to 100%, 25% to 50%, 25% to 60%, 25% to 70%, 25% to 75%, 25% to 80%, 25% to 85%, 25% to 90%, 25% to 95%, 25% to 100%, 30% to 50%, 30% to 60%, 30% to 70%, 30% to 75%, 30% to 80%, 30% to 85%, 30% to 90%, 30% to 95%, 45% to 100%, 50% to 70%, 50% to 75%, 50% to 80%, 50% to 85%, 50% to 90%, 50% to 95%, 50% to 100%, 55% to 75%, 55% to 80%, 55% to 85%, 55% to 90%, 55% to 95%, 55% to 100%, 60% to 75%, 60% to 80%, 60% to 85%, 60% to 90%, 60% to 95%, 60% to 100%, 70% to 80%, 70% to 85%, 70% to 90%, 70% to 95%, 70% to 100%, 75% to 85%, 75% to 90%, 75% to 95%, 75% to 100%, 80% to 85%, 80% to 90%, 80% to 95%, 80% to 100%, 85% to 90%, 85% to 95%, 85% to 100%, 90% to 95%, 95% to 100%, and the like.

In some embodiments, the microalgae cells of the biomass can be disrupted or lysed and the microalgae oils extracted. The microalgae cells can be extracted wet or dry according to conventional techniques known to those of skill in the art, to produce a complex containing fatty acids. The disruption or lysis of the microalgae cells can be carried out according to conventional techniques including, but not limited to, treating the cells with boiling water or by mechanical breaking such as grinding, pulverizing, sonication or the French press, or any other method known to those of skill in the art. Extraction of the fatty acids from the lysed cells follow standard procedures used with microalgae and other organisms that are known to those of skill in the art, including, but not limited to, separating the liquid phase from the solid phase following cell lysis, extracting the fatty acids in the liquid phase by the addition of a solvent, evaporating the solvent, and recovering the polyunsaturated fatty acids obtained from the liquid phase of the lysed cells. See also, Bligh and Dyer, *Can. J. Biochem. Physiol.* 37:911-917 (1959); U.S. Pat. No. 5,397,591; U.S. Pat. No. 5,338,673, and U.S. Pat. No. 5,567,732; the disclosures herein incorporated by reference in their entirety.

Solvents that can be used for extraction include, but are not limited to, hexane, chloroform, ethanol, methanol, isopropanol, diethyl ether, dioxan, isopropyl ether, dichloromethane, tetrahydrofuran, and combinations thereof. In a further embodiment the microalgae cells can be extracted using supercritical fluid extraction with solvents such as $CO_2$ or NO. Extraction techniques using supercritical extraction are known to those of skill in the art and are described in McHugh et al. *Supercritical Fluid Extraction*, Butterworth, 1986, herein incorporated by reference in its entirety.

In the processes, compositions, food products, dietary supplements, feed additives and the like, of the present invention, the polyunsaturated fatty acids may be provided in the form of free fatty acids, cholesterol esters, salt esters, fatty acid esters, monoglycerides, diglycerides, triglycerides, diacylglycerols, monoglycerols, sphingophospholipids, sphingoglycolipids, or any combination thereof. In some embodiments of the present invention, the fatty acids are provided in the Rolm of triglycerides. In other embodiments, the fatty acids are not provided in the form of phospholipids (e.g., are provided in a non phospholipid form).

The GLA of the present invention can be supplemented with additional GLA obtained from other sources, including, but not limited to, plants. Thus, the GLA of the present invention can be supplemented with GLA obtained from plant sources that include, but are not limited to, borage, black currant, echium, and primrose. In particular embodiments, the supplemental GLA is from borage or borage oil. In some embodiments, the microalgae GLA is supplemented with additional GLA from microalgae sources. In other embodiments, the GLA of the invention is not supplemented.

Method for Preparing A Microalgae Biomass

In other aspects, the present invention provides a method for preparing a microalgae biomass comprising one or more PUFAs. The method comprises:

culturing a micro algae under a culture condition sufficient to provide a microalgae biomass comprising the one or more PUFAs, wherein the microalgae biomass is harvested at a logarithmic growth phase of the microalgae.

Generally, the microalgae biomass comprises the microalgae. In some embodiments, the biomass contains little or no contaminating microorganisms such as, for example, yeast, bacteria, virus, etc. In some embodiments, the microalgae biomass has a microalgae purity of at least about 50%, illustratively, at least about 50, 60, 70, 80, 90, 95, 98, 99, 99.5, and 100%. In other embodiments, the microalgae biomass comprises a single strain of a microalgae.

In some embodiments, the microalgae is a member of the genus *Rhodomonas*. Examples of species belonging to the genus *Rhodomonas* include, but are not limited to, *Rhodomonas salina, Rhodomonas abbreviate, Rhodomonas astrosea, Rhodomonas baltica, Rhodomonas chrysoidea, Rhodomonas duplex, Rhodomonas falcate, Rhodomonas lens, Rhodomonas maculate, Rhodomonas mariana*, and *Rhodomonas ovalis*.

In some embodiments, the microalgae is a genetically modified variant of a *Rhodomonas* species or strain.

The term a "genetically modified variant," as used herein is intended to refer to a strain that has a genome which is modified (e.g., mutated, changed) from its normal (e.g., wildtype, naturally occurring) form such that a desired result is achieved. For example, a genetically modified variant of a microalgae species or strain can include a microalgae species or strain in which nucleic acid molecules (e.g., fatty acid synthase, desaturase, elongase) have been inserted, deleted, and/or modified in such a manner that such modifications provide the desired effect within the microalgae. Also, for example, a nucleic acid molecule of the species or strain can be modified by subjecting the microalgae species or strain to a condition and/or a mutagen whereby the nucleic acid molecule is modified (e.g., one or more mutations in a protein coding or a non-coding region) such that a desired result is achieved.

In one embodiment, the microalgae is a *Rhodomonas salina*.

In other embodiments, the microalgae is a strain deposited under a Provasoli-Guillard National Center for Culture of Marine Phytoplankton (CCMP) (West Boothbay Harbor, Me.) strain number selected from the group consisting of: CCMP272, CCMP273, CCMP275, CCMP318, CCMP322, CCMP323, CCMP324, CCMP739, CCMP740, CCMP741, CCMP742, CCMP743, CCMP744, CCMP746, CCMP747, CCMP748, CCMP749, CCMP750, CCMP751, CCMP752, CCMP753, CCMP754, CCMP755, CCMP756, CCMP757, CCMP758, CCMP759, CCMP760, CCMP761, CCMP762, CCMP763, CCMP766, CCMP767, CCMP768, CCMP1170, CCMP1171, CCMP1178, CCMP1319, CCMP1419, CCMP1420, CCMP1533, CCMP1749, CCMP2005, and CCMP2045. In some embodiments, a strain derived from the deposited microalgae is provided by the present invention.

In one embodiment, the microalgae is a genetically modified variant of a strain deposited under a Provasoli-Guillard National Center for Culture of Marine Phytoplankton (CCMP) (West Boothbay Harbor, Me.) strain number selected from the group consisting of: CCMP272, CCMP273, CCMP275, CCMP318, CCMP322, CCMP323, CCMP324, CCMP739, CCMP740, CCMP741, CCMP742, CCMP743, CCMP744, CCMP746, CCMP747, CCMP748, CCMP749, CCMP750, CCMP751, CCMP752, CCMP753, CCMP754, CCMP755, CCMP756, CCMP757, CCMP758, CCMP759, CCMP760, CCMP761, CCMP762, CCMP763, CCMP766, CCMP767, CCMP768, CCMP1170, CCMP1171, CCMP1178, CCMP1319, CCMP1419, CCMP1420, CCMP1533, CCMP1749, CCMP2005, and CCMP2045.

In another embodiment, the microalgae is a strain deposited under strain number CCMP757 or a genetically modified variant thereof.

Isolated microalgae strains having the following identifiers: 4Rsal, 5Rsal, 9Rsal, 12Rsp, and 16Rsp were each deposited with the American Type Culture Collection (ATCC), 10801 University Boulevard Manassas, Va., 20110, on Apr. 30, 2009, and assigned the following Accession Numbers: ATCC No. PTA-9986; ATCC No. PTA-9987; ATCC No. PTA-9988; ATCC No. PTA-9989; and ATCC No. PTA-9990.

In one embodiment, the microalgae is the 12Rsp strain deposited under ATCC strain number ATCC No. PTA-9989 or a genetically modified variant thereof.

In another embodiment, the microalgae has a small subunit ribosomal RNA (SSU rRNA) gene sequence comprising that of SEQ. ID No. 1 or SEQ ID NO:2.

In one embodiment, the one or more PUFAs is an omega-3, an omega-6 fatty acid, or both.

In another embodiment, the omega-3 fatty acid is selected form the group consisting of: C16:3 (n-3), C18:3 (n-3), C18:4 (n-3), C20:3 (n-3), C20:4 (n-3), C20:5 (n-3), C22:5 (n-3), C22:6 (n-3), C24:5 (n-3), and C24:6 (n-3), wherein the letter "C" accompanied by a number denotes the number of carbons in the hydrocarbon chain, followed by a colon and a number indicating the number of double bonds, wherein (n-3) denotes "omega-3."

In some embodiments, the one or more PUFAs is an omega-3-fatty acid selected from the group consisting of α-Linolenic acid (ALA), stearidonic acid (SDA), eicosatrienoic acid, eicosatetraenoic acid, eicosapentaenoic acid (EPA), docosapentaenoic acid (DPA), clupanodonic acid, docosahexaenoic acid (DHA), tetracosapentaenoic acid, and tetracosahexaenoic acid. In another embodiment, the omega-3-fatty acid is selected from the group consisting of α-Linolenic acid (ALA), stearidonic acid (SDA), eicosapentaenoic acid (EPA), and docosapentaenoic acid (DPA).

In one embodiment, the omega-3-fatty acid is stearidonic acid (SDA).

The term "logarithmic growth phase," as used herein refers to a stage of culturing characterized by exponentially increasing numbers of microalgae cells. Generally, in a culture system, there is a characteristic growth pattern following inoculation that includes a lag phase, an exponential or "logarithmic growth phase," a negative growth acceleration phase, and a plateau or "stationary phase." For example, in the logarithmic growth phase, as growth of the microalgae continues, cells can reach their maximum rate of cell division and numbers of cells increase in log relationship to time. Within time after the commencement of the log phase, the rate of cell division can begin to decline and some of the cells can begin to die. This can be reflected on the growth curve by a gradual flattening out of the line. Eventually the rate of cells dying is essentially equal to the rate of cells dividing, and the total viable population can remain the same for a period of time. This is known as the stationary or plateau phase and is represented on the growth curve as a flattening out of the line where the slope approaches zero.

In some embodiments, the culture condition is sufficient for the microalgae to produce the one or more PUFAs (e.g., omega-3 fatty acid) and/or other lipid products. The culture condition comprises a culture medium suitable for growing the microalgae thereby providing the microalgae biomass comprising the PUFAs. Such a culture medium can be an aqueous medium (e.g., seawater) comprising a carbon, a nitrogen (e.g., nitrate), and a phosphorus (e.g., phosphate) source. The medium also can comprise salts, vitamins, minerals, metals, and other nutrients. Preferably, the culture condition is sufficient to provide a suitable amount of light and temperature for the microalgae.

In some embodiments, the step of culturing further comprises limiting a nutrient (e.g., nitrogen, phosphorous) for a suitable time to increase the amount of the PUFAs, preferably at least one omega-3 fatty acid. For example, the culture can be transferred to a phosphorus-free or nitrogen-free (or -less medium) and/or the initial nitrogen content of the growth medium can be provided such that nitrogen becomes depleted at a later time, for example later in the exponential phase. In one embodiment, the ratio of carbon to nitrogen of the culture medium can be high.

In other embodiments, the culture medium comprises a first phosphorus concentration at a lag phase and a second phosphorus concentration at the logarithmic growth phase at harvest, wherein the second phosphorus concentration is at or within about 20% of the first phosphorus concentration.

In other embodiments, the second phosphorus concentration can be greater than about 20% of the first phosphorus concentration, illustratively, about 20 to about 90%, about 25 to about 80%, about 30 to about 70%, and about 40 to about 50% of the first phosphorus concentration.

In one embodiment, the source of phosphorus comprises a phosphate (e.g., sodium phosphate).

In other embodiments, the culture medium comprises a first nitrogen concentration at a lag phase and a second nitrogen concentration at the logarithmic growth phase at harvest, wherein the second nitrogen concentration is at or within about 20% of the first nitrogen concentration.

In other embodiments, the second nitrogen concentration can be greater than about 20% of the first nitrogen concentration, illustratively, about 20 to about 90%, about 25 to about 80%, about 30 to about 70%, and about 40 to about 50% of the first nitrogen concentration.

In one embodiment, the nitrogen source comprises a nitrate (e.g., sodium nitrate). In some embodiments, the nitrogen source includes ammonium (e.g., ammonium chloride).

In other embodiments, the culture condition is sufficient for the microalgae to produce the one or more PUFAs, wherein the one or more PUFAs comprises an omega-3-fatty acid, wherein the omega-3-fatty acid is SDA, wherein the amount of the SDA at the logarithmic phase at time of harvest is at least about 5% of the total fatty acid content of the microalgae, illustratively, about 5 to about 50%, about 15 to about 40%, and about 20 to about 30% of the total fatty acid content of the microalgae. In another embodiment, the omega-3-fatty acid is SDA and ALA, wherein the culture condition is sufficient such that the amount each of SDA and ALA at the logarithmic phase at harvest is at least about 5% of the total fatty acid content of the microalgae, illustratively, about 5 to about 50%, about 15 to about 40%, and about 20 to about 30% of the total fatty acid content of the microalgae.

In some embodiments, the culture condition is sufficient such that the amount of an omega-6-fatty acid at the logarithmic phase is less than about 50% of the total fatty acid content of the microalgae, illustratively, less than about 50, 45, 40, 35, 30, 35, 25, 10, 9, 8, 7, 6, 5, 4, 3, 2, 1, 0.5, and 0.1% of the total fatty acid content of the microalgae.

Culturing of the microalgae can be performed in a conventional bioreactor suitable for culturing the microalgae to provide the microalgae biomass. For example, the microalgae can be cultured by a fermentation process including, but not limited to, batch, fed-batch, cell recycle, and continuous fermentation. In one embodiment, the microalgae is cultured in a photobioreactor or pond. In another embodiment, culturing is performed using a flat panel or tubular reactor design.

A variety of methods can be used to harvest the microalgae cells from the culture medium. In one embodiment, harvesting comprises recovering the microalgae biomass from the culture medium by separating, for example by filtration (e.g., belt filtration, rotary drum filtration) and/or centrifugation. If desired, the harvested microalgae cells can then be washed, frozen, lyophilized, spray dried, and/or stored under a non-oxidizing atmosphere of a gas (e.g., $CO_2$, $N_2$) to reduce or eliminate the presence of $O_2$. Optionally, synthetic and/or natural antioxidants including, but not limited to, butylated hydroxytoluene (BHT), butylated hydroxyanisole (BHA), tert-butylhydroquinone (TBHQ), ethoxyquin, beta-carotene, vitamin E, and vitamin C also can be added to the harvested cells. The amount and/or type of antioxidant(s) provided can depend on the desired product formulation, packaging method, and/or the desired shelf life.

In still other embodiments, the present invention provides a method for preparing a microalgae biomass comprising one or more PUFAs, the method comprising:

culturing a micro algae under a culture condition sufficient to provide a microalgae biomass comprising the one or more PUFAs, wherein the microalgae biomass is harvested at a negative growth acceleration phase or a stationary phase of the microalgae.

In one embodiment, the microalgae is a strain deposited under strain number CCMP757 or a genetically modified variant thereof.

In another embodiment, the microalgae is the 12Rsp strain deposited under ATCC strain number ATCC No. PTA-9989 or a genetically modified variant thereof.

In yet another embodiment, the microalgae has a small subunit ribosomal RNA (SSU rRNA) gene sequence comprising that of SEQ. ID No. 1 or SEQ ID NO:2.

Microalgae Biomass

In other aspects, the present invention provides a microalgae biomass and/or a fraction and/or an extract thereof.

In one embodiment, the microalgae biomass comprises lipids having at least 5% by weight of total fatty acids as omega-3 fatty acids, illustratively, about 5 to about 100%, about 70 to about 90%, and about 70 to about 75% by weight of total fatty acids as omega-3 fatty acids.

In another embodiment, the microalgae biomass comprises lipids having at least 10% by weight of total fatty acids as omega-3 and omega-6 fatty acids, illustratively, at least about: 10, 20, 30, 40, 50, 60, 70, 80, 90, 95, 96, 97, 98, 99, and 100%.

In some embodiments, the microalgae biomass comprises an omega-3 fatty acid content of at least 1% dry weight of the biomass, illustratively, about 1% to about 50%, about 12% to about 40%, about 14% to about 30%, about 16% to about 20% dry weight of the biomass.

In one embodiment, the microalgae biomass is prepared in accordance with the methods of the present invention. For example, in some embodiments, the microalgae biomass is prepared by a method comprising: culturing a microalgae under a culture condition sufficient to provide the microalgae biomass, wherein the biomass comprises one or more PUFAs, wherein the microalgae biomass is harvested at a logarithmic growth phase of the microalgae. In other embodiments, the microalgae biomass is harvested at a negative growth acceleration phase or a stationary phase of the microalgae.

Method for Preparing a Lipid Composition

In other aspects, the present invention provides a method for preparing a lipid composition comprising one or more PUFAs. The method comprises:

obtaining the lipid composition from a microalgae biomass cultured under a culture condition sufficient to provide the microalgae biomass, wherein the biomass comprises the one or more PUFAs, wherein the microalgae biomass is harvested at a logarithmic growth phase of the microalgae. In other embodiments, the microalgae biomass is harvested at a negative growth acceleration phase or a stationary phase of the microalgae.

Methods for obtaining a lipid composition from the biomass include, but are not limited to, extraction, heat, pressure, saponification, sonication, freezing, grinding, ion exchange, chromatography, membrane separation, electrodialysis, reverse osmosis, distillation, chemical derivatization, crystallization, etc.

For example, cellular lipids comprising the one or more PUFAs (e.g., an omega-3 fatty acid) can be extracted from the microalgae cells by any suitable method including, but not limited to, extraction with a solvent including, but not limited to, ethanol, ethyl acetate, isopropyl alcohol, methanol, ethyl acetate, hexane, methylene chloride, methanol, chloroform, and the like, or by pressurized liquid hydrocarbons such as butane, pentane, propane, or others (with our without co-solvents), or through supercritical fluid extraction (with or without co-solvents). Optionally, the extracted oil can be evaporated under reduced pressure to reduce or remove the solvent and/or produce a sample of concentrated lipid material.

In other embodiments, the cells can be broken or lysed to obtain the lipid composition, for example into vegetable or other edible oil.

Extracted oils can be subjected to refining (e.g. chemical refining, physical refining). A refining process can remove some or all impurities from extracted oils. The refining process can comprise one or more methods to degum, bleach, filter, deodorize and/or polish the extracted oils.

In another embodiment, the one or more PUFAs contained in the extracted lipid composition can be concentrated by hydrolyzing the lipids and concentrating a PUFA fraction, preferably a PUFA fraction comprising SDA, by employing a method such as, for example, urea adduction, fractional distillation, column chromatography, and/or supercritical fluid fractionation.

Accordingly, in one embodiment, the step of obtaining the lipid composition from the biomass comprises: extracting the lipid composition from the biomass. In another embodiment, the step of extracting comprises contacting the biomass with a polar solvent.

For example, oil can be extracted from the microalgae biomass to provide the lipid composition using a solvent under an extraction condition sufficient to extract polyunsaturated fatty acids (PUFAs) and/or molecules comprising PUFAs but not compounds that are insoluble in the solvent. In one embodiment, the lipid composition is extracted from the microalgae biomass, wherein cellular debris and/or precipitated insoluble compounds are separated from a miscella comprising the PUFA and the solvent. In another embodiment, the method further comprises separating the cellular debris and precipitated compounds using a separation method such as filtration, centrifugation, and/or combinations thereof.

In some embodiments, the solvent is a polar solvent. Examples of polar solvent include, but are not limited to, ethanol, ethyl acetate, isopropyl alcohol, methanol, ethyl acetate, and mixtures thereof. In one embodiment, the polar solvent is ethanol.

Extraction of the lipid composition with a solvent can be carried out in a variety of ways. For example, the extraction can be a batch process, a continuous process, or a continuous counter-current process. In a continuous counter-current process, the solvent contact with the microalgae leaches the oil into the solvent, providing increasingly more concentrated miscellas (i.e., solvent-oil), while the solvent-solids is contacted with miscellas of decreasing concentration. Following extraction, the solvent can be removed from the miscella using methods known in the art. For example, distillation, rotary evaporation, or a rising film evaporator and steam stripper or any suitable desolventizer can be used for removing the solvent.

In one embodiment, the method further comprises subjecting the extracted lipid (i.e., the lipid composition) to an absorption process (e.g., bleaching) to remove one or more undesirable compounds such as, for example, color bodies and/or phosphatides that may be present. For example, the absorption process can be a bleaching process comprising contacting the lipid composition with a bleaching material (e.g, neutral earth (also termed natural clay or fuller's earth), acid-activated earth, activated carbon, activated clays, silicates, and or a combination thereof) and a filter aid.

In some embodiments, the total amount of bleaching material that is used is at least about 0.5 wt. %, illustratively, about 0.1 to about 3 wt. %; about 0.3 wt. % to about 2.5 wt. %; and about 0.5 to about 1.5 wt. %. In one embodiment, about 0.5% each (by weight) of bleaching clay, activated carbon, and filter aid is used as bleaching material.

In one embodiment, the method further comprises subjecting the extracted lipid to a degumming step. Degumming methods are known in the art including, for example, water degumming, acid degumming, enzymatic degumming, and membrane degumming.

In some embodiments, the lipid composition, preferably following the absorption process, is subjected to degumming, wherein the step of degumming comprises contacting the lipid composition with a mixture of aqueous acids that are in amounts effective to precipitate gums and/or chlorophyll-type compounds that may be present in the lipid composition.

In one embodiment, the mixture of aqueous acids comprises sulfuric acid and phosphoric acid. In another embodiment, equal amounts of aqueous acids are mixed with the lipid composition. Preferably, the acids are in a suitable ratio and, when blended with the oil, are in an amount sufficient to provide an acidic pH, illustratively, a pH of about 1.5 to about 5. A pH probe or other suitable method can be used to monitor and control pH.

Precipitates that form after acid mixing can be removed from the lipid composition, for example using centrifugation and/or filtration (e.g., membrane filtration).

In some embodiments, the degummed lipid composition can be subjected to drying for a time, a temperature, and/or a vacuum condition sufficient to reduce a moisture content of the composition. In some embodiments, the moisture content of the dried lipid composition is less than about 10 weight percent, illustratively, less than 10, 5, 1, 0.9, 0.8, 0.7, 0.6, 0.5, 0.4, 0.3, 0.2, 0.1, 0.05, ad 0.01 weight percent.

Lipid Composition

In other aspects, the present invention provides a lipid composition prepared from a microalgae biomass, wherein the lipid composition comprises one or more PUFAs produced by a microalgae of the biomass. In some embodiments, the lipid composition is prepared in accordance with the methods of the present invention.

In one embodiment, the microalgae is a *Rhodomonas*. In another embodiment, the microalgae is a *Rhodomonas salina* or a genetically modified derivative thereof. In some embodiments, the microalgae is a strain deposited under strain number CCMP757 or a genetically modified derivative thereof. In other embodiments, the microalgae is a strain deposited under ATCC strain number ATCC No. PTA-9989 or a genetically modified variant thereof.

In some embodiments, the lipid composition comprises SDA in a total SDA amount of at least about 5% of the total fatty acid content of the lipid composition, illustratively, about 5 to about 50%, about 10 to about 40%, and about 20 to about 30% of the total fatty acid content of the lipid composition, wherein the SDA is produced by the microalgae. In other embodiments, the total SDA amount of the lipid composition is about 15 to about 30% of the total fatty acid content of the lipid composition.

In other embodiments, the total amount each of GLA and AA contained in the lipid composition is less than about 10% of the total fatty acid content of the lipid composition, illustratively, less than about 10, 9, 8, 7, 6, 5, 4, 3, 2, 1, 0.5, and 0.1% of the total fatty acid content of the lipid composition, wherein the GLA and AA, if present, each is produced by the microalgae.

In one embodiment, the lipid composition further comprises ALA in a total ALA amount of at least about 5% of the total fatty acid content of the lipid composition, illustratively, about 5 to about 50%, about 10 to about 40%, and about 20 to about 30% of the total fatty acid content of the lipid composition, wherein the ALA is produced by the microalgae. In other embodiments, the total ALA amount of the lipid composition is about 15 to about 30% of the total fatty acid content of the lipid composition.

In some embodiments, the lipid composition further comprises EPA in a total EPA amount of at least about 1% of the total fatty acid content of the lipid composition, illustratively, about 1 to about 50%, about 10 to about 40%, and about 20 to about 30% of the total fatty acid content of the lipid composition, wherein the EPA is produced by the microalgae. In other embodiments, the total EPA amount of the lipid composition is about 5 to about 15% of the total fatty acid content of the lipid composition.

In one embodiment, the lipid composition further comprises DHA in a total DHA amount of at least about 1% of the total fatty acid content of the lipid composition, illustratively, about 1 to about 50%, about 10 to about 40%, and about 20 to about 30% of the total fatty acid content of the lipid composition, wherein the DHA is produced by the microalgae. In other embodiments, the total DHA amount of the lipid composition is about 5 to about 15% of the total fatty acid content of the lipid composition.

In other embodiments, the total SDA amount of the lipid composition is about 15 to about 30% of the total fatty acid content of the lipid composition.

In one embodiment, the lipid composition further comprises ALA, EPA, and DHA, wherein the total ALA amount of the lipid composition is about 15 to about 30% of the total fatty acid content of the lipid composition, wherein the total EPA amount of the lipid composition is about 5 to about 15% of the total fatty acid content of the lipid composition, wherein the total DHA amount of the lipid composition is about 5 to about 15% of the total fatty acid content of the lipid composition, wherein the total fatty acid amount each of GLA and AA contained in the lipid composition is less than about 10% of the total fatty acid content of the lipid composition.

Polyunsaturated Fatty Acid Compositions, Food Products and Animal Feed Additives In other aspects, a whole-cell microalgae biomass, fraction, and/or extract thereof can be used for consumption or as a food additive to enhance the PUFA content and nutritional value of a food.

For example, in some embodiments, when used as animal feed (e.g., cattle feed, dairy feed, aqua feed, poultry feed), the one or more PUFAs produced by the microalgae can be incorporated into the flesh or other products of animals including, but not limited to, livestock, poultry, cattle, and fish. The PUFAs also can be used for pharmaceutical or nutritional purposes and industrial applications.

The one or more PUFAs can be provided in any one of a variety of forms/compositions suitable for a particular application or use. Thus, for example, in some embodiments, a whole-cell microalgae biomass and/or a fraction and/or extract thereof, provides the one or more PUFAs. In another embodiment, the PUFAs are in a powdered form or as a free oil in a liquid form (e.g., lipid composition or a fraction or concentrate thereof).

In various embodiments, human and/or animal consumption/use of the one or more PUFAs is contemplated. Accordingly, in one embodiment, the PUFA produced by the microalgae is provided in a form and/or grade suitable for use in an end-product selected from the group consisting of: a feed, a dietary supplement, a food, a pharmaceutical formulation, a dairy product, and an infant formula.

For example, in one embodiment, the harvested microalgae biomass is dried (e.g., spray drying, tunnel drying, vacuum drying) and used as a feed or food supplement for any animal or aquaculture organism (e.g., fish, shrimp, crab, lobster, etc.) whose meat and/or products are consumed by humans or animals (e.g., pets, livestock).

In another embodiment, the harvested microalgae biomass is mixed with a dry moisture-reducing agent (e.g., ground grain such as ground corn).

In other embodiments, pharmaceutical compositions are contemplated.

The present invention further provides compositions made by the processes of the invention as described above. Accordingly, in some embodiments of the invention a polyunsaturated fatty acid composition is provided, the polyunsaturated fatty acid composition comprising at least 8% polyunsaturated fatty acids; the composition comprising at least one fatty acid extracted from a microalgae, wherein (a) GLA is in an amount of 0.1% to 10% of total fatty acids; (b) SDA is in an amount of 5% to 50% of total fatty acids; (c) EPA is in an amount of 2% to 30% of total fatty acids, and (d) DHA is in an amount of 2% to 30% of total fatty acids.

In some embodiments, the polyunsaturated fatty acid composition comprises polyunsaturated fatty acids at a concentration in a range from 5% to 35%. Thus, the polyunsaturated fatty acid composition can comprise polyunsaturated fatty acids at a concentration of 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, and the like. In other embodiments, the polyunsaturated fatty acid composition can comprise polyunsaturated fatty acids at a concentration in a range from 5% to 7%, 5% to 8%, 5% to 10%, 5% to 12%, 5% to 15%, 5% to 20%, 5% to 25%, 5% to 30%, 6% to 8%, 6% to 10%, 6% to 12%, 6% to 15%, 6% to 20%, 6% to 25%, 6% to 35%, 7% to 9%, 7% to 11%, 7% to 13%, 7% to 14%, 7% to 15%, 7% to 20%, 7% to 25%, 7% to 30%, 7% to 35%, 8% to 10%, 8% to 12%, 8% to 14%, 8% to 15%, 8% to 20%, 8% to 25%, 8% to 35%, 9% to 11%, 9% to 13%, 9% to 15%, 9% to 20%, 9% to 25%, 9% to 30%, 9% to 35%, 10% to 12%, 10% to 13%, 10% to 14%, 10% to 15%, 10% to 20%, 10% to 25%, 10% to 30%, 10% to 35%, 15% to 20%, 15% to 25%, 15% to 30%, 20% to 25%, 20% to 30%, 20% to 35%, 25% to 30%, 25% to 35%, 30% to 35%, and the like. In one embodiment, the polyunsaturated fatty acid composition comprises polyunsaturated fatty acids at a concentration of at least 8%.

According to the present invention, the amount of GLA that can be included in the composition is in a range from 1% to 10% of total fatty acids. Thus, the GLA can be included in the composition in an amount of total fatty acids of 0.1%, 0.2%, 0.3%, 0.4%, 0.5%, 0.6%, 0.7%, 0.8%, 0.9%, 1.0%, 2%, 3%, 4%, 5%, 6%, 7%, 8%, 9%, 10%, and the like. In other embodiments, the GLA can be included in the composition in an amount of total fatty acids in a range from 0.1% to 1%, 1% to 3%, 1% to 5%, 1% to 7%, 1% to 9%, 2% to 4%, 2% to 6%, 2% to 8%, 2% to 10%, 3% to 5%, 3% to 7%, 3% to 9%, 3% to 10%, 4% to 6%, 4% to 8%, 4% to 10%, 5% to 7%, 5% to 9%, 5% to 10%, 6% to 8%, 6% to 9%, 6% to 10%, 7% to 9%, 7% to 10%, 8% to 10%, 9% to 10%, and the like.

In some embodiments, the amount of SDA that is included in the composition of the present invention is in a range from 5% to 50% of total fatty acids. Thus, the SDA can be provided in the composition in an amount of total fatty acids of 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, and the like. In other embodiments, the SDA can be included in the composition in an amount of total fatty acids in a range from 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, 45% to 50%, and the like.

In other embodiments, the EPA can be included in the composition in a range from 2% to 30% of total fatty acids.

Thus, the EPA can be provided in the composition in an amount of total fatty acids of 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, and the like. In other embodiments, the EPA can be included in the composition in an amount of percent of total fatty acids in a range from 1% to 5%, 1% to 10%, 1% to 15%, 1% to 20%, 1% to 25%, 1% to 30%, 5% to 10%, 5% to 15%, 5% to 20%, 5% to 25%, 5% to 30%, 10% to 15%, 10% to 20%, 10% to 25%, 10% to 30%, 15% to 20%, 15% to 25%, 15% to 30%, 20% to 25%, 20% to 30%, 25% to 30%, and the like.

In some embodiments of the present invention, the DHA can be included in the composition in a range from 2% to 30% of total fatty acids. Thus, the DHA can be provided in the composition in an amount of total fatty acids of 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, and the like. In other embodiments, the DHA can be included in the composition in an amount of total fatty acids in a range from 1% to 5%, 1% to 10%, 1% to 15%, 1% to 20%, 1% to 25%, 1% to 30%, 5% to 10%, 5% to 15%, 5% to 20%, 5% to 25%, 5% to 30%, 10% to 15%, 10% to 20%, 10% to 25%, 10% to 30%, 15% to 20%, 15% to 25%, 15% to 30%, 20% to 25%, 20% to 30%, 25% to 30%, and the like.

The present invention further provides a composition comprising at least 5% SDA, the composition comprising either: (a) a microalgae oil extracted from a cultivated microalgae biomass or (b) a microalgae biomass from a cultivated microalgae, wherein water is removed from microalgae biomass to achieve a solids content from about 5 to 100% weight percent. In some embodiments, the SDA is not in a phospholipid form. In some embodiments, the SDA is present in the composition in an amount in a range from 2% to 10%. Thus, the SDA is present in the composition in an amount of 2%, 3%, 4%, 5%, 6%, 7%, 8%, 9%, 10%, and the like. In other embodiments, the SDA can be included in the composition in a range from 2% to 4%, 2% to 6%, 2% to 8%, 2% to 10%, 3% to 5%, 3% 25 to 7%, 3% to 9%, 3% to 10%, 4% to 6%, 4% to 8%, 4% to 10%, 5% to 7%, 5% to 8%, 5% to 9%, 5% to 10%, 6% to 8%, 6% to 9%, 6% to 10%, 7% to 9%, 7% to 10%, 8% to 10%, 9% to 10%, and the like. In some embodiments, the SDA is not in a phospholipid form.

In an additional embodiment, the present invention provides a food product comprising: (a) from 0.01-99.99 percent by weight of a composition comprising at least 8% polyunsaturated fatty acids, wherein the fatty acids are extracted from a microalgae, further wherein (i) GLA is in an amount of 0.1% to 10% of total fatty acids; (ii) SDA is in an amount of 5% to 50% of total fatty acids; (iii) EPA is in an amount of 2% to 30% of total fatty acids, and (iv) DHA is in an amount of 2% to 30% of total fatty acids; in combination with (b) from 99.99 to 0.01 percent by weight of at least one additional ingredient selected from the group consisting of proteins, carbohydrates and fiber, and combinations thereof.

In some embodiments, the food product of the invention can comprise polyunsaturated fatty acids at a concentration in a range from 5% to 35%. Thus, the food product can comprise polyunsaturated fatty acids at a concentration of 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, and the like. In other embodiments, the food product can comprise polyunsaturated fatty acids at a concentration in a range from 5% to 7%, 5% to 8%, 5% to 10%, 5% to 12%, 5% to 15%, 5% to 20%, 5% to 25%, 5% to 30%, 6% to 8%, 6% to 10%, 6% to 12%, 6% to 15%, 6% to 20%, 6% to 25%, 6% to 35%, 7% to 9%, 7% to 11%, 7% to 13%, 7% to 14%, 7% to 15%, 7% to 20%, 7% to 25%, 7% to 30%, 7% to 35%, 8% to 10%, 8% to 12%, 8% to 14%, 8% to 15%, 8% to 20%, 8% to 25%, 8% to 35%, 9% to 11%, 9% to 13%, 9% to 15%, 9% to 20%, 9% to 25%, 9% to 30%, 9% to 35%, 10% to 12%, 10% to 13%, 10% to 14%, 10% to 15%, 10% to 20%, 10% to 25%, 10% to 30%, 10% to 35%, 15% to 20%, 15% to 25%, 15% to 30%, 20% to 25%, 20% to 30%, 20% to 35%, 25% to 30%, 25% to 35%, 30% to 35%, and the like. In one embodiment, the food product comprises polyunsaturated fatty acids at a concentration of at least 8% by weight.

According to the present invention, the amount of GLA that can be included in the food product is in a range from 0.1% to 10% of total fatty acids. Thus, the GLA can be included in the food product in an amount of total fatty acids of 0.1%, 0.2%, 0.3%, 0.4%, 0.5%, 0.6%, 0.7%, 0.8%, 0.9%, 1.0%, 2%, 3%, 4%, 5%, 6%, 7%, 8%, 9%, 10%, and the like. In other embodiments, the GLA can be included in the food product in an amount of total fatty acids in a range from 0.1% to 1%, 1% to 3%, 1% to 5%, 1% to 7%, 1% to 9%, 2% to 4%, 2% to 6%, 2% to 8%, 2% to 10%, 3% to 5%, 3% to 7%, 3% to 9%, 3% to 10%, 4% to 6%, 4% to 8%, 4% to 10%, 5% to 7%, 5% to 8%, 5% to 9%, 5% to 10%, 6% to 8%, 6% to 9%, 6% to 10%, 7% to 9%, 7% to 10%, 8% to 10%, 9% to 10%, and the like.

In some embodiments, the amount of SDA that is included in the food product of the present invention is in a range from 5% to 50% of total fatty acids. Thus, the SDA can be provided in the food product in an amount of total fatty acids of 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, and the like. In other embodiments, the SDA can be included in the food product in an amount of total fatty acids in a range from 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, 45% to 50%, and the like.

In other embodiments, the EPA can be included in the food product in a range from 2% to 30% of total fatty acids. Thus, the EPA can be provided in the food product in an amount of total fatty acids of 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, and the like. In other embodiments, the EPA can be included in the food product in an amount of percent of total fatty acids in a range from 1% to 5%, 1% to 10%, 1% to 15%, 1% to 20%, 1% to 25%, 1% to 30%, 5% to 10%, 5% to 15%, 5% to 20%, 5% to 25%, 5% to 30%, 10% to 15%, 10% to 20%, 10% to 25%, 10% to 30%, 15% to 20%, 15% to 25%, 15% to 30%, 20% to 25%, 20% to 30%, 25% to 30%, and the like.

In some embodiments of the present invention, the DHA can be included in the food product in a range from 2% to 30% of total fatty acids. Thus, the DHA can be provided in the food product in an amount of total fatty acids of 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, and the like. In other embodiments, the DHA can be included in the food product in an amount of total fatty acids in a range from 1% to 5%, 1% to 10%, 1% to 15%, 1% to 20%, 1% to 25%, 1% to 30%, 5% to 10%, 5% to 15%, 5% to 20%, 5% to 25%, 5% to 30%, 10% to 15%, 10% to 20%, 10% to 25%, 10% to 30%, 15% to 20%, 15% to 25%, 15% to 30%, 20% to 25%, 20% to 30%, 25% to 30%, and the like.

Further embodiments of the invention provide a food product comprising: (a) from 0.01-99.99 percent by weight of a composition comprising at least 5% stearidonic acid (weight percent; w/w), the composition comprising either: (i) a microalgae oil extracted from a cultivated microalgae biomass or (ii) a microalgae biomass from a cultivated microalgae, wherein water is removed from microalgae biomass to achieve a solids content from about 5 to 100% weight percent; in combination with (b) from-99.99 to 0.01 percent by weight of at least one additional ingredient selected from the group consisting of proteins, carbohydrates and fiber, and combinations thereof. In some embodiments of the invention, the SDA is not in a phospholipid form.

In some embodiments, the SDA is present in the composition in an amount in a range from 2% to 10%. Thus, the SDA is present in the composition in an amount of 2%, 3%, 4%, 5%, 6%, 7%, 8%, 9%, 10%, and the like. In other embodiments, the SDA can be included in the composition in a range from 2% to 4%, 2% to 6%, 2% to 8%, 2% to 10%, 3% to 5%, 3% to 7%, 3% to 9%, 3% to 10%, 4% to 6%, 4% to 8%, 4% to 10%, 5% to 7%, 5% to 8%, 5% to 9%, 5% to 10%, 6% to 8%, 6% to 9%, 6% to 10%, 7% to 9%, 7% to 10%, 8% to 10%, 9% to 10%, and the like.

In the present invention, the amount of the fatty acid composition in any of the food products described herein can be between 0.01% and 99.99% by weight of the food product. Thus, the amount of fatty acid composition in the food product can be 0.1%, 0.2%, 0.3%, 0.4%, 0.5%, 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.7%, 99.8%, 99.9% and the like. In other embodiments, the amount of the fatty acid composition in the food product is in a range from 0.1% to 5%, 0.1% to 10%, 0.1% to 15%, 0.1% to 20%, 0.1% to 25%, 0.1% to 30%, 0.1% to 35%, 0.1% to 40%, 0.1% to 45%, 0.1% to 50%, 0.1% to 60%, 0.1% to 70%, 0.1% to 80%, 0.1% to 90%, 0.1% to 99%, 0.1% to 99.5%, 0.5% to 5%, 0.5% to 10%, 0.5% to 15%, 0.5% to 20%, 0.5% to 25%, 0.5 to 35%, 0.5% to 45%, 0.5% to 55%, 0.5% to 65%, 5% to 25%, 5% to 35%, 5% to 45%, 5% to 55%, 5% to 65%, 5% to 75%, 5% to 80%, 5% to 85%, 5% to 95%, 5% to 99%, 10% to 30%, 10% to 40% 10% to 50%, 10% to 60%, 10% to 70%, 10% to 75%, 10% to 80%, 10% to 85%, 10% to 95%, 10% to 99%, 10% to 99.9%, 15% to 35%, 15% to 45%, 15% to 55%, 15% to 65%, 15% to 75%, 15% to 85%, 15% to 95%, 15% to 99%, 15% to 99.9%, 20% to 40%, 20% to 50%, 20% to 60%, 20% to 70%, 20% to 75%, 20% to 80%, 20% to 85%, 20% to 95%, 20% to 99%, 25% to 40%, 25% to 50%, 25% to 60%, 25% to 70%, 25% to 75%, 25% to 80%, 25% to 85%, 25% to 95%, 25% to 99%, 30% to 50%, 30% to 55%, 30% to 60%, 30% to 65%, 30% to 70%, 30% to 75%, 30% to 80%, 30% to 85%, 30% to 90%, 30% to 95%, 30% to 99%, 35% to 50%, 35% to 55%, 35% to 60%, 35% to 65%, 35% to 70%, 35% to 75%, 35% to 80%, 35% to 85%, 35% to 90%, 35% to 95%, 35% to 99%, 40% to 50%, 40% to 55%, 40% to 60%, 40% to 65%, 40% to 70%, 40% to 75%, 40% to 80%, 40% to 85%, 40% to 90%, 40% to 95%, 40% to 99%, 45% to 60%, 45% to 65%, 45% to 70%, 45% to 75%, 45% to 80%, 45% to 85%, 45% to 90%, 45% to 95%, 45% to 99%, 50% to 60%, 50% to 65%, 50% to 70%, 50% to 75%, 50% to 80%, 50% to 85%, 50% to 90%, 50% to 95%, 50% to 99%, 55% to 65%, 55% to 70%, 55% to 75%, 55% to 80%, 55% to 85%, 55% to 90%, 55% to 95%, 55% to 99%, 60% to 70%, 60% to 75%, 60% to 80%, 60% to 85%, 60% to 90%, 60% to 95%, 60% to 99%, 65% to 80%, 65% to 85%, 65% to 90%, 65% to 95%, 65% to 99%, 70% to 80%, 70% to 85%, 70% to 90%, 70% to 95%, 70% to 99%, 75% to 85%, 75% to 90%, 75% to 95%, 75% to 99%, 80% to 90%, 80% to 95%, 80% to 99%, 85% to 90%, 85% to 95%, 85% to 99%, 90% to 95%, 90% to 99%, 95% to 99%, and the like.

The present invention further provides a liquid dietary supplement for diminishing symptoms of inflammatory disorders, said supplement consisting essentially of: 19 weight percent water; 25 weight percent sucrose; 35 weight percent oils, wherein the oils are GLA and SDA from a microalgae; 15 weight percent flavoring; and 5 weight percent glycerin.

In further embodiments, the water can be in a range from 10-30% weight percent. Thus, the water can be present in an amount of 10%, 11%, 12%, 13%, 14%, 15%, 16%, 17%, 18%, 19%, 20%, 21%, 22%, 23%, 24%, 25%, 26%, 27%, 28%, 29%, 30%, and the like. In additional embodiments, the sucrose is present in an amount in a range from 10% to 40%. Thus, the sucrose can be present in an amount of 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40% and the like.

In still further embodiments, the oils can be present in an amount in a range from 20% to 50% (weight percent; w/w). Thus, the oils can be present in an amount of 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, and the like. In some embodiments, the flavoring can be present in an amount in a range from 5%-25%. Thus, the flavoring can be present in an amount of 5%, 6%, 7%, 8%, 9%, 10%, 11%, 12%, 13%, 14%, 15%, 16%, 17%, 18%, 19%, 20%, 21%, 22%, 23%, 24%, 25%, and the like. In other embodiments, the glycerin can be present in a range from 1%-20%. Thus, the glycerin can be present in an amount of 1%, 2%, 3%, 4%, 5%, 6%, 7%, 8%, 9%, 10%, 11%, 12%, 13%, 14%, 15%, 16%, 17%, 18%, 19%, 20%, and the like.

The liquid dietary supplement can further comprise less than 1 weight percent minor ingredients selected from antioxidants, preservatives, colorants, stabilizers, emulsifiers or a combination thereof.

In some embodiments, the weight ratio of GLA to SDA in the liquid dietary supplement can be in a range from 6:1 to 1:6. Thus, the weight ratio of GLA to SDA can be 6.0:1.0, 5.0:1.0, 4.0:1.0, 3.0:1.0, 3.0:0.5, 2.5:1.5, 2.5:0.5, 2.0:1.0, 2.0:0.5, 1.0:1.0, 1.0:2.0, 1.0:3.0, 1.0:4.0, 1.0:5.0, 1.0:6.0, and the like.

The present invention further provides animal feed additives made by the processes of the invention described herein. Thus, in some embodiments of the invention an animal feed additive is provided wherein the animal feed additive comprises polyunsaturated fatty acids collected from microalgae either in the form of: a) a microalgae oil extracted from a cultivated microalgae biomass or (b) a microalgae biomass from a cultivated microalgae, wherein water is removed from microalgae biomass to achieve a solids content from about 5 to 100% weight percent.

In further embodiments, the fatty acids collected from the microalgae for the animal feed additive are short chain omega-3 fatty acids.

Additionally provided herein is an animal feed additive comprising at least 8% polyunsaturated fatty acids; the additive comprising fatty acids extracted from a microalgae, wherein: (a) GLA is in an amount of 0.1% to 10% of total fatty acids; (b) SDA is in an amount of 5% to 50% of total fatty acids; (c) EPA is in an amount of 2% to 30% of total fatty acids, and (d) DHA is in an amount of 2% to 30% of total fatty acids.

In some embodiments, the animal feed additive comprises polyunsaturated fatty acids at a concentration in a range of 5% to 15%. Thus, the animal feed additive can comprise polyunsaturated fatty acids at a concentration of 5%, 6%, 7%, 8%, 9%, 10%, 11%, 12%, 13%, 14%, 15%, and the like. In other embodiments, the animal feed additive can comprise polyunsaturated fatty acids at a concentration in a range from 5% to 7%, 5% to 8%, 5% to 10%, 5% to 12%, 5% to 15%, 6% to 8%, 6% to 10%, 6% to 12%, 6% to 15%, 7% to 9%, 7% to 11%, 7% to 13%, 7% to 14%, 7% to 15%, 8% to 10%, 8% to 12%, 8% to 14%, 8% to 15%, 9% to 11%, 9% to 13%, 9% to 15%, 10% to 12%, 10% to 13%, 10% to 14%, 10% to 15%, and the like. In one embodiment, the animal feed additive comprises polyunsaturated fatty acids at a concentration of at least 8%.

According to the present invention, the amount of GLA in the animal feed additive is in a range from 0.1% to 10% of total fatty acids. Thus, the GLA in the animal feed additive can be in an amount of total fatty acids of 0.1%, 0.2%, 0.3%, 0.4%, 0.5%, 0.6%, 0.7%, 0.8%, 0.9%, 1.0%, 2%, 3%, 4%, 5%, 6%, 7%, 8%, 9%, 10%, and the like. In other embodiments, the GLA in the animal feed additive can be in an amount of total fatty acids in a range from 0.1% to 1%, 1% to 3%, 1% to 5%, 1% to 7%, 1% to 9%, 2% to 4%, 2% to 6%, 2% to 8%, 2% to 10%, 3% to 5%, 3% to 7%, 3% to 9%, 3% to 10%, 4% to 6%, 4% to 8%, 4% to 10%, 5% to 7%, 5% to 8%, 5% to 9%, 5% to 10%, 6% to 8%, 6% to 9%, 6% to 10%, 7% to 9%, 7% to 10%, 8% to 10%, 9% to 10%, and the like.

In some embodiments, the amount of SDA in the animal feed additive of the present invention is in a range from 5% to 50% of total fatty acids. Thus, the animal feed additive can comprise SDA in an amount of total fatty acids of 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, and the like. In other embodiments, the SDA in the animal feed additive is in an amount of total fatty acids in a range from 5% to 10%, 5% to 15%, 5% to 20%, 5% to 25%, 5% to 30%, 5% to 35%, 5% to 40%, 5% to 45%, 5% to 50%, 10% to 15%, 10% to 20%, 10% to 25%, 10% to 30%, 10% to 35%, 10% to 40%, 10% to 45%, 10% to 50%, 20% to 25%, 20% to 30%, 20% to 35%, 20% to 40%, 20% to 45%, 20% to 50%, 25% to 30%, 25% to 35%, 25% to 40%, 25% to 45%, 25% to 50%, 30% to 35%, 30% to 40%, 30% to 45%, 30% to 50%, 35% to 40%, 35% to 45%, 35% to 50%, 40% to 45%, 40% to 50%, 45% to 50%, and the like. In other embodiments, the EPA in the animal feed additive can be in a range from 2% to 30% of total fatty acids. Thus, the EPA in the animal feed additive is in an amount of total fatty acids of 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, and the like.

In other embodiments, the EPA in the animal feed additive is in an amount of percent of total fatty acids in a range from 1% to 5%, 1% to 10%, 1% to 15%, 1% to 20%, 1% to 25%, 1% to 30%, 5% to 10%, 5% to 15%, 5% to 20%, 5% to 25%, 5% to 30%, 10% to 15%, 10% to 20%, 10% to 25%, 10% to 30%, 15% to 20%, 15% to 25%, 15% to 30%, 20% to 25%, 20% to 30%, 25% to 30%, and the like.

In some embodiments of the present invention, the DHA in the animal feed additive is in a range from 2% to 30% of total fatty acids. Thus, the DHA in the animal feed additive is in an amount of total fatty acids of 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, and the like. In other embodiments, the DHA is in the animal feed additive in an amount of total fatty acids in a range from 1% to 5%, 1% to 10%, 1% to 15%, 1% to 20%, 1% to 25%, 1% to 30%, 5% to 10%, 5% to 15%, 5% to 20%, 5% to 25%, 5% to 30%, 10% to 15%, 10% to 20%, 10% to 25%, 10% to 30%, 15% to 20%, 15% to 25%, 15% to 30%, 20% to 25%, 20% to 30%, 25% to 30%, and the like. In other embodiments of the present invention further comprise animal products produced by feeding to an animal the animal feed additives described herein. Therefore, one aspect of the invention includes an animal product produced by feeding to an animal an animal feed additive comprising polyunsaturated fatty acids collected from microalgae either in the faun of: (a) a microalgae oil extracted from a cultivated microalgae biomass or (b) a microalgae biomass from a cultivated microalgae, wherein water is removed from microalgae biomass to achieve a solids content from about 5 to 100% weight percent. Still other aspects of the invention provide an animal product produced by feeding to an animal an animal feed additive comprising at least 8% polyunsaturated fatty; the additive comprising fatty acids extracted from a microalgae, wherein the microalgae fatty acid extract comprises (a) GLA in an amount of 0.1% to 10% of total fatty acids; (b) SDA in an amount of 5% to 50% of total fatty acids; (c) EPA in an amount of 2% to 30% of total fatty acids; and (d) DHA in an amount of 2% to 30% of total fatty acids.

An animal product of the present invention includes, but is not limited to, eggs, milk, or meat.

The compositions of the present invention as described herein may be used as a complete food product, as a component of a food product, as a dietary supplement or as part of a dietary supplement, as a feed additive and may be either in liquid, semisolid or solid form. The compositions of the present invention as described herein additionally may be in the form of a pharmaceutical composition. The compositions, dietary supplements, food products, baby food products, feed additives, and/or pharmaceutical compositions of the present invention may advantageously be utilized in methods for promoting the health of an individual.

As indicated above, the compositions may be in liquid, semisolid or solid form. For example, the compositions may be administered as tablets, gel packs, capsules, gelatin capsules, flavored drinks, as a powder that can be reconstituted into such a drink, cooking oil, salad oil or dressing, sauce, syrup, mayonnaise, margarine or the like. Furthermore, the food product, dietary supplements, and the like, of the present invention can include, but are not limited to, dairy products, baby food, baby formula, beverages, bars, a powder, a food topping, a drink, a cereal, an ice cream, a candy, a snack mix, a baked food product and a fried food product. Beverages of the invention include but are not limited to energy drinks, nutraceutical drinks, smoothies, sports drinks, orange juice and other fruit drinks. A bar of the present invention includes, but is not limited to, a meal replacement, a nutritional bar, a snack bar and an energy bar, an extruded bar, and the like. Dairy products of the invention include, but are not limited to, including but not limited to yogurt, yogurt drinks, cheese and milk.

The food products or dietary supplements of the present invention may further comprise herbals, herbal extracts, fungal extracts, enzymes, fiber sources, minerals, and vitamins. The microalgae oils and microalgae biomass of the present invention may be used in the compositions of the invention for both therapeutic and non-therapeutic uses. Thus, the compositions, food products and animal feed additives of the present invention may be used for therapeutic or non-therapeutic purposes.

Compositions intended for oral administration may be prepared according to any known method for the manufacture of dietary supplements or pharmaceutical preparations, and such compositions may include at least one additive selected from the group consisting of taste improving substances, such as sweetening agents or flavoring agents, stabilizers, emulsifiers, coloring agents and preserving agents in order to provide a dietetically or pharmaceutically palatable preparation. Vitamins, minerals and trace element from any physiologically acceptable source may also be included in the composition of the invention.

A pharmaceutical composition of the present invention comprises the said compositions of the present invention in a therapeutically effective amount. The compositions may additionally comprise prescription medicines or non-prescription medicines. The combinations may advantageously produce one or more of the following effects: (1) additive and/or synergistic benefits; (2) reduction of the side effects and/or adverse effects associated with use of the prescription medicine in the absence of the said formulations; and/or (3) the ability to lower the dosage of the prescription medicine in comparison to the amount of prescription medicine needed in the absence of the said formulations.

The active agents of the present invention can be prepared in the form of their pharmaceutically acceptable salts. As understood by one of skill in the art, pharmaceutically acceptable salts are salts that retain the desired biological activity of the parent compound and do not impart undesired toxicological effects. Examples of such salts are (a) acid addition salts formed with inorganic acids, for example, hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p¬toluenesulfonic acid, naphthalenedisulfonic acid, polygalacturonic acid, and the like; (b) salts fowled from elemental anions such as chlorine, bromine, and iodine; and (c) salts derived from bases, such as ammonium salts, alkali metal salts such as those of sodium and potassium, alkaline earth metal salts such as those of calcium and magnesium, and salts with organic bases such asisopropylamine, trimethylamine, histidine, dicyclohexylamine and N¬methyl-D-glucamine.

In some embodiments, one or more PUFAs are in the triglyceride form. In another embodiment, one or more PUFAs are in the esterified form (e.g., ethyl ester form). In still further embodiments, the fatty acids are in the form of acid salts.

The active agents can be formulated for administration in accordance with known pharmacy techniques. See, e.g., Remington, *The Science And Practice of Pharmacy* (9th Ed. 1995). In the manufacture of a pharmaceutical composition according to the present invention, the active agents (including the physiologically acceptable salts thereof) is typically admixed with, inter alia, an acceptable carrier. The carrier must, of course, be acceptable in the sense of being compatible with any other ingredients in the formulation and must not be deleterious to the subject. The carrier can be a solid or a liquid, or both, and can be formulated with the active agent as a unit-dose formulation, for example, a tablet, which can contain from 0.01% or 0.5% to 95% or 99%, or any value between 0.01% and 99%, by weight of the active agent. One or more active agents can be incorporated in the compositions of the invention, which can be prepared by any of the well-known techniques of pharmacy, comprising admixing the components, optionally including one or more accessory ingredients. Moreover, the carrier can be preservative free, as described herein above.

In one embodiment, the pharmaceutically acceptable carrier is physiological saline, ringers, or phosphate-buffered saline.

In some embodiments, the active agents comprise a lower limit ranging from about 0.01, 0.02, 0.03, 0.04, 0.05, 0.06, 0.07, 0.08, 0.09, 1, 2, 3, 4, 5, 6, 7, 8, 9, and 10% to an upper limit ranging from about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100% by weight of the composition. In some embodiments, the active agent includes from about 0.05% to about greater than 99% by weight of the composition.

The pharmaceutical compositions according to embodiments of the present invention are generally formulated for oral and topical (i.e., skin, ocular and mucosal surfaces) administration, with the most suitable route in any given case depending on the nature and severity of the condition being treated and on the nature of the particular active agent which is being used.

However, the pharmaceutical compositions of the present invention also can be formulated for use through any other route where the active ingredients may be effectively administered, e.g. including, but not limited to, intravenously, subcutaneously, rectally, vaginally, etc.

Formulations suitable for oral administration can be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations can be prepared by any suitable method of pharmacy, which includes bringing into association the active compound and a suitable carrier (which can contain one or more accessory ingredients as noted above). In general, the formulations of the invention are prepared by uniformly and intimately admixing the active compound with a liquid or finely divided solid carrier, or both, and then, if necessary, shaping the resulting mixture.

For example, a tablet can be prepared by compressing or molding a powder or granules containing the active compound, optionally with one or more accessory ingredients. Compressed tablets can be prepared by compressing, in a suitable machine, the compound in a free-flowing form, such as a powder or granules optionally mixed with a binder, lubricant, inert diluent, and/or surface active/dispersing agent(s). Molded tablets can be made by molding, in a suitable machine, the powdered compound moistened with an inert liquid binder.

In another embodiment, a capsule comprising the one or more PUFAs is provided. For example, the capsule can be prepared by placing the PUFA-containing formulation inside a capsule shell. A capsule can be a dosage form administered in a container or enclosure comprising an active agent. In some embodiments, the one or more PUFAs are in liquid form (e.g., lipid composition) and are filled into hard or soft capsules. A capsule shell can be made of methylcellulose, hydroxypropylmethyl cellulose, polyvinyl alcohols, or denatured gelatins or starch or other material. Hard shell capsules are typically made of blends of relatively high gel strength bone and pork skin gelatins. In some embodiments, a unit dosage form is a gel capsule. In other embodiments the capsule shell is a glycerin capsule shell. In still further embodiments, the capsule is a bovine gelatin shell. Other suitable capsule shell materials include, but are not limited to, polyethylene, polypropylene, poly(methylmethacrylate), polyvinylchloride, polystyrene, polyurethanes, polytetrafluoroethylene, nylons, polyformaldehydes, polyesters, cellulose acetate, and nitrocellulose. Gelatin capsule shells also are provided and can be made of, e.g., tapioca, grass, vegetable derived or fish derived gelatin. Vegetarian based gelatin capsules can be made of, e.g., vegetable derived hydroxypropylmethyl cellulose. Capsules shells also are contemplated that contain, e.g., modified maize starch, glycerol, and/or carrageenan as a gelling agent.

In other embodiments, capsule shells can be made of a porous or a pH-sensitive polymer made by a thermal forming process. In one embodiment, the capsule shell is in the form of a membrane characterized as having a relatively thin skin on one surface; and most of whose thickness is constituted of a highly permeable porous material.

Thus, any of number of pharmaceutically acceptable oral dosage forms are contemplated including, but not limited to, pills, tablets, gel capsules, and the like. Also contemplated herein are pharmaceutical compositions, comprising pharmaceutical formulations in a unit dosage form. In such dosage forms, the formulation is subdivided into suitably sized unit doses containing appropriate quantities of the PUFAs, an effective amount to achieve the desired purpose.

Thus, the present invention also provides capsule, tablet, liquid, syrup, suspensions, sublingual, candy, and chewable dosage forms of the PUFA formulations.

In some embodiments, liquid form preparations include solutions, suspensions and emulsions. Examples of liquid pharmaceutical preparations include propylene glycol solutions and solutions containing sweeteners for oral solutions, suspensions, and emulsions. Injectable solutions also are contemplated. Further, formulations suitable for topical administration can be in the form of crèmes and liquids including, for example, syrups, suspensions or emulsions, inhalants, sprays, mousses, oils, lotions, ointments, gels, solids and the like.

Suitable pharmaceutically acceptable topical carriers include, but are not limited to, water, glycerol, alcohol, propylene glycol, fatty alcohols, triglycerides, fatty acid esters, and mineral oils. Suitable topical cosmetically acceptable carriers include, but are not limited to, water, petroleum jelly, petrolatum, mineral oil, vegetable oil, animal oil, organic and inorganic waxes, such as microcrystalline, paraffin and ozocerite wax, natural polymers, such as xanthanes, gelatin, cellulose, collagen, starch or gum arabic, synthetic polymers, alcohols, polyols, and the like. Preferably, because of its non-toxic topical properties, the pharmaceutically and/or cosmetically-acceptable carrier is substantially miscible in water. Such water miscible carrier compositions can also include sustained or delayed release carriers, such as liposomes, microsponges, microspheres or microcapsules, aqueous based ointments, water-in-oil or oil-in-water emulsions, gels and the like.

In other embodiments, a pharmaceutical composition of the present invention can further comprise an excipient. Examples of excipients include, but are not limited to, fillers, stabilizers, extenders, binders, humidifiers, surfactants, lubricants, and the like. An excipient can be inert or it can possess pharmaceutical benefits. Excipients can be selected with respect to the intended form of administration.

A pharmaceutical formulation also can further comprise an anti-inflammatory formulation, a chemotherapeutic agent, an active excipient, an osteoporosis drug, an anti-depressant, an anti-convulsant, an anti-*Helicobactor pylori* drug, a drug for treatment of neurodegenerative disease, a drug for treatment of degenerative liver disease, an antibiotic, and a cholesterol lowering formulation.

In one embodiment, the present invention provides a pharmaceutical composition comprising the whole-cell microalgae biomass and/or a fraction and/or an extract thereof. In another embodiment, the pharmaceutical composition comprises the lipid composition extracted from the microalgae biomass. In some embodiments, the whole-cell microalgae biomass and/or a fraction and/or an extract thereof is present in the pharmaceutical composition in a prophylactically or therapeutically effective amount. In other embodiments, the pharmaceutical composition further comprises a pharmaceutically acceptable carrier.

In one embodiment, the formulations of the present invention can further comprise a plasticizer. Examples of plasticizers include, but are not limited to, polyethylene glycols such as PEG 300, PEG 400, PEG 600, PEG 1450, PEG 3350, and PEG 800, stearic acid, propylene glycol, oleic acid, triethyl cellulose, and triacetin.

Also contemplated are coated compositions/formulations such as, for example, an enteric coating. Examples of coating materials included, but are not limited, polyvinyl acetate phthalate, hydroxypropylmethylcellulose acetate succinate, cellulose acetate phthalate, methacrylic acid copolymer, hydroxypropylmethylcellulose succinate, cellulose acetate succinate, cellulose acetate hexahydrophthalate, hydroxypropylmethylcellulose hexahydrophthalate, hydroxypropylmethylcellulose phthalate (HPMCP), cellulose propionate phthalate, cellulose acetate maleate, cellulose acetate trimellitate, cellulose acetate butyrate, cellulose acetate propionate, methacrylic acid/methacrylate polymer, methacrylic acid-methyl methacrylate copolymer, ethyl methacrylate-methylmethacrylate-chlorotrimethylammonium ethyl methacrylate copolymer, and combinations thereof. Other examples of coatings include natural resins (e.g., shellac, copal collophorium) and synthetic resins (e.g., resins bearing carboxyl groups).

In other embodiments, the compositions/formulations of the present invention also can further comprise a stabilizer and/or a preservative. In some embodiments the stabilizer is an antioxidant. Examples of preservatives include, but are not limited to, potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

The pharmaceutically acceptable compounds of the invention will normally be administered to a subject in a daily dosage regimen. For an adult subject this may be, for example, an oral dose of GLA between 0.1 gram and 15 grams. In further embodiments, an oral dose of GLA can be between 0.5 gram and 10 grams. In still further embodiments, an oral dose of GLA can be between 0.5 grams and 3 grams. In other embodiments, an oral dose of SDA can be between 0.1 g and 10 grams. In additional embodiments, an oral dose of SDA can be between 0.25 grams and 5 grams. In yet additional embodiments, an oral dose of SDA can be between 0.25 grams and 3 grams. In addition, some embodiments of the invention can optionally include an oral dose of EPA or DHA between about 0.1 g and about 15 g.

The pharmaceutical compositions may be administered 1 to 4 times per day. Thus in particular embodiments, compositions are contemplated comprising a 1:1 (w/w) ratio of GLA:EPA, wherein there may be 1, 2, 3, 4, 5, 6, 7, 8, 9, or 10 grams of GLA. In other embodiments there may be a 2:1 ratio of (w/w) ratio of GLA:EPA, wherein there may be 1, 2, 3, 4, 5, 6, 7, 8, 9, 10, 11, 12, 13 14 or 15 grams of GLA. Of course, the ratio of GLA:EPA administered may be varied from that disclosed herein above. For example, any amount of EPA including 0.1, 0.25, 0.5, 1, 2, 3, 4, 5, 6, 7, 8, 9 or 10 grams of EPA may be administered with any amount of GLA including 1, 2, 3, 4, 5, 6, 7, 8, 9, 10, 11, 12, 13, 14, or 15 grams of GLA. Such amounts of either supplement may be admixed in one composition or may be in distinct compositions.

Methods of Treatment

Accordingly, a further aspect of the present invention provides administering the PUFAs to a human for the therapeutic and/or prophylactic treatment of a disease or condition.

For example, the invention includes methods of preventing and treating of cardiovascular disease, autoimmune disorders, inflammatory disorders, central nervous system disorders, and chronic pain by providing the fatty acid compositions and/or formulation as described herein. The subject can be a human or a non-human. Non-human subjects include livestock animals, such as cattle, sheep, and horses and domestic companion animals, such as cats and dogs.

In one embodiment, the disease or condition is selected from the group consisting of: cardiovascular disease, chronic inflammation, acute inflammation, gastrointestinal disorder, cancer, cachexia, cardiac restenosis, neurodegenerative disorder, degenerative disorder of the liver, blood lipid disorder, osteoporosis, osteoarthritis, autoimmune disease, preeclampsia, preterm birth, age related maculopathy, pulmonary disorder, schizophrenia, depression, weight maintenance, and peroxisomal disorder.

Cardiovascular diseases and disorders that can be treated with the fatty acid formulations described herein include, but are not limited to, angina, atherosclerosis, hypercholesterolemia, hypertriglyceridemia, low HDL, high blood pressure, Raynaud's disease, and cardiac arrhythmias. Methods of treatment with the fatty acid formulations described herein include prophylaxis to prevent post-cardiotomy (including but not limited to coronary artery bypass graft surgery and valve surgery) complications (including but not limited to depression, neuro-cognitive decline, congestive heart failure and infarction, clotting events, and arrhythmias) as well as for the treatment for such complications. The invention includes a method of preventing or reducing the risk of a second myocardial infarction by providing the fatty acid-containing compositions and formulation as described herein at least one time per day for at least 60 days, 180 days, 360 days, or more to a patient following a first myocardial infarction.

Non-limiting examples of diseases and disorders that can be treated with the methods and compositions described herein also include alopecia, Alzheimer's dementia, anxiety disorders, asthma, attention deficit disorder, attention-deficit hyperactivity disorder, atopic dermatitis, autism, bipolar disorder, borderline personality disorder, cardiovascular disease, chronic fatigue syndrome, chronic pain, chronic polyarthritis, cognitive disorders, communication disorders, Crohn's disease, cystic fibrosis, dementia, depression, diabetes (of the non-insulin dependent or insulin dependent forms), diabetes-related sequelae, diabetic neuropathy, dry eyes and other inflammatory eye disorders, dry skin, dysmenorrhea, eating disorders (such as anorexia nervosa or bulimia nervosa and obesity), eczema, fibromyalgia, gout, lupus, male infertility, metabolic syndrome, melanoma, mild cognitive impairment, migraine, mood disorders, multiple sclerosis, obsessive-compulsive disorder, oppositional-defiant disorder, osteoarthritis, osteoporosis, pervasive developmental disorders, polyarteritis nodosa, psoriasis, psoriatic arthritis, rheumatoid arthritis, schizophrenia, scleroderma, self-injurious behavior, sickle cell anemia, tic disorders, ulcerative colitis, or vasculitic disorders (such as polyarteritis nodosa and temporal arteritis.

In one embodiment, the fatty acid compositions and formulations described herein can be used to prevent cell carcinomas. In some embodiments, the compositions and formulations described herein are given to patients in remission to reduce the risk of recurrence.

The fatty acid compositions and formulations described herein also can be used in humans and animals for cosmetic purposes. For example the formulations may be used to improve skin quality and clarity and hair or coat shine.

One of ordinary skill in the art knows that the specific dose level for any particular subject will depend upon a variety of factors including the age, body weight, general health, sex, diet, time of administration, and route of administration.

In one embodiment, the present invention provides a method for treating a disease or disorder in a subject, the method comprising: administering to the subject a therapeutically or prophylactically effective amount of a lipid composition of the present invention.

In some embodiments, the therapeutically or prophylactically effective amount is the lipid composition provided as at least about 0.1% of daily calories of the subject, illustratively, at least about 0.1 to about 30, about 0.5 to about 20, and about 1 to about 5% of daily calories.

In other embodiments, the therapeutically or prophylactically effective amount is at least about 0.1 gram per day, illustratively, about 0.1 to about 50 g/day, about 1 to about 30 g/day, about 5 to about 20 g/day, and about 10 to about 15 g/day.

In one embodiment, the subject is a hypertriglyceridemic subject. In another embodiment, the subject is an asthmatic.

In some embodiments, the present invention provides a method for lowering plasma triglycerides in a subject, the method comprising administering to the subject a lipid composition of the present invention. In one embodiment, the subject is a hypertriglyceridemic subject.

In other embodiments, the present invention provides a method for lowering IgE-induced leukotriene release from basophils in a subject, the method comprising administering to the subject a lipid composition of the present invention. In one embodiment, the subject is a hypertriglyceridemic subject. In one embodiment, the subject is an asthmatic subject.

Kits

In other aspects, a kit or a package comprising the compositions and formulations of the present invention is provided. For example, packaged pharmaceutical formulations can include one or more PUFA dosage forms in a container; and instructions for using the dosage form for prophylactic or therapeutic treatment of a subject. In some embodiments, the present invention provides a kit comprising a pharmaceutical composition of the present invention. The kit can contain one or more separate containers.

Although the instructional materials, when present, typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

When the components of the kit are provided in one or more liquid solutions, the liquid solution is preferably an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container. For example, wherein the components of the kit are in lyophilized form, the kit may optionally contain a sterile and physiologically acceptable reconstitution medium such as water, saline, buffered saline, and the like.

In some embodiments, the containers of the kit can include at least one vial, test tube, flask, bottle, syringe or other containers, into which the compositions/formulations of the present invention, and any other desired agent, may be placed and, preferably, suitably aliquoted. Where separate components are included, the kit will also generally contain at least a second container into which these are placed, enabling the administration of separated designed doses. The kits may also comprise additional containers for containing a sterile, pharmaceutically acceptable buffer or other diluent.

The kits may also contain devices by which to administer the compounds of the present invention, for example one or more needles or syringes, or even an eye dropper, pipette, or other such like apparatus. The kits of the present invention will also typically include structures for containing the vials, or such like, and other component, in close confinement for commercial sale, such as, e.g., injection or blow-molded plastic containers into which the desired vials and other apparatus are placed and retained.

The present invention will now be described with reference to the following example. It should be appreciated that this example is for the purpose of illustrating aspects of the present invention, and does not limit the scope of the invention as defined by the claims.

EXAMPLES

Example 1

Culture Conditions

*Rhodomonas salina* cells were maintained in 125-ml flasks containing 50 ml of growth media (see below) at room temperature with continuous irradiance of 50 µmol m$^{-2}$ s$^{-1}$. Culture flasks were under constant shaking at 100 rpm, using a shaking table.

For all experiments, illumination was provided with white fluorescent bulbs (40 watt), various light intensities were achieved by changing the numbers of light bulbs or by adjusting the distance between the culture flasks and the light bulbs. For temperature experiments, culture flasks were incubated in a water bath at temperatures between 14° C. to 34° C. The temperature in the water bath was controlled by an electrical heating rod (Aquatic Ecosystem, Apopka, Fla.) at 22° C., 28° C., or 34° C., respectively. Compressed air enriched with 1-2% $CO_2$ was used to mix the cultures, as well as to facilitate gas ($O_2$ and $CO_2$) exchange and liquid mass transfer.

The growth medium used was the following f/2 Medium composition (Table 1):

TABLE 1

| Growth medium f/2 | | |
|---|---|---|
| | Component | Molar Concentration in Final Medium |
| Macro-nutrients | $NaNO_3$ | $8.83 \times 10^{-1}$M |
| | $NaH_2PO_4 H_2O$ | $3.63 \times 10^{-5}$M |
| | $Na_2SiO_3 9H_2O*$ | $1.07 \times 10^{-4}$M* |

TABLE 1-continued

| Growth medium f/2 | | |
|---|---|---|
| | Component | Molar Concentration in Final Medium |
| Micro-nutrients | $FeCl_3 6H_2O$ | $1 \times 10^{-5}$M |
| | $Na_2EDTA 2H_2O$ | $1 \times 10^{-5}$M |
| | $CuSO_4 SJ_2O$ | $4 \times 10^{-5}$M |
| | $Na_2MoO_4 2H_2O$ | $3 \times 10^{-8}$M |
| | $ZnSO_4 7H_2O$ | $8 \times 10^{-8}$M |
| | $CuCl_2 6H_2O$ | $5 \times 10^{-8}$M |
| | $MnCl_2 4H_2O$ | $9 \times 10^{-7}$M |
| Vitamin Mix | Vitamin $B_{12}$ (cyanocobalamin) | $1 \times 10^{-10}$M |
| | Biotin | $2 \times 10^{-9}$M |
| | Thiamine HC1 | $3 \times 10^{-7}$M |

All nutrient components were finally dissolved either in 1 liter filtered natural seawater or artificial seawater made up of 3.4% sea salt. The seawater was collected from Institute of Marine Sciences at UNC—Chapel Hill, Morehead City, N.C. The sea salt was purchased from Aquatic Ecosystem Inc. (Apopka, Fla.). The stock solutions for macro-nutrients, micro-nutrients, or vitamin mix were prepared separately and mix together before use. For axenic media preparation, the mixed media were autoclaved.

Example 2

Growth Measurement

The specific growth rate was measured by cell count, optical density of 550 nm (O.D. 550), chlorophyll concentration, or dry weight.

Cell counts: A one ml of culture suspension was withdrawn daily. Microalgae cells were fixed with Lugol's solution and counted with a haemocytometer. Cell concentration is expressed as total number of cells per milliliter of culture volume.

Dry weight analysis: A one to ten ml culture sample was filtered through a pre-dried, weighed Whatman GF/C filter paper. Cells on the filter paper were washed three times with 3.4% ammonia bicarbonate to remove the salt. The filter paper containing algal cells was dried overnight in an oven at 100° C. The ammonia bicarbonate evaporated during this process. The difference between the final weight and the weight before filtration was the dry weight of the sample (Lu et al., *J. Phycol.* 30: 829-833 (1994)).

O.D. 550: A one ml culture suspension was withdrawn daily to monitor the optical density at 550 nm using a Genesys 10Vis spectrophotometer (Thermo Electron Corp.).

Chlorophyll & carotenoids: One-half ml to five ml culture sample was harvested by filtration on Whatman GF/C filter paper. One ml of 100% methanol was used to extract pigments overnight at 4° C. The supernatant was collected after centrifugation and pigments determined by absorption spectroscopy. The following equations were used to calculate chlorophyll and carotenoid content: Chl-α (µgmL$^{-1}$)=13.9 $A_{665}$; Total carotenoids (µgmL$^{-1}$)=4$A_{480}$ (Montero et al., *Botanica Marina* 45: 305-315 (2002)).

The specific growth rate was calculated using the following formula: $\mu(d^{-1})=(LnN_2-LnN_1)/(t_2-t_1)$, where $t_1$ and $t_2$ represent different time points, and $N_1$ and $N_2$ represent chlorophyll concentration, O.D. 550, dry weight or cell concentration at time $t_1$ and time $t_2$, respectively.

Example 3

Fatty Acids Extraction and Measurement

Cells were harvested by filtration on Whatman GF/C filter paper. Total lipids were extracted according to the method of Bligh and Dyer (Bligh, E. and W. Dyer, *Can. J. Biochem. Physiol.* 37: 911-917 (1959)).

Fatty acids methyl ester analysis was performed using an Agilent 6890 GC equipped with a split/splittless injector at 230° C., a flame ionization detector at 260° C., an autosampler (Agilent Technologies, Waldbronn, Germany) and a CP SIL 88 column (100 m, 0.25 mm, 0.2.25 m film thickness, Varian, Datuistadt, Germany). Hydrogen was used as carrier gas at constant flow rate of 1 ml/min. The temperature of the GC oven was set to 70° C. for 3 min, increased at 8° C./min to 180° C., held for 2 min, increased at 4° C./min to 210° C., held for 4 min, increased at 2° C./min to a final temperature of 240° C. and held for 25 min. HP Chemstation software (Rev. A.08.03) was used for data analysis. The sample was injected using a split ratio of 1:10.

Example 4

Cytotoxicity Assay

The method for determining cytotoxicity was modified according to Meyer et al. (*Planta Med.* 45, 31-34 (1982)). Briefly, algal cells were tested at a concentration of 5×106 cells/ml in triplicates using a 96-well microplate. Brine shrimp eggs (*Artemia salina* Leach) were purchased in a local pet store and hatched in artificial seawater (solution of 3.4% sea salt) at room temperature. After 24 hours, the larvae (nauplii) were collected. A suspension of 8-12 nauplii (100 µl) was added to each well containing algal cells and the microplate was covered and incubated for 24-72 hours at room temperature. During this period, the number of dead nauplii in each well was counted using a binocular microscope (10×). The survival rate of the nauplii was used as the indicator for the toxicity of the algal species tested.

Example 5

Fatty Acid Profiles of *Rhodomonas sauna* and *Amphidinium carterae*

The microalgae were cultivated in 125 ml flasks with f/2 medium under a light intensity of 50 µmol $m^{-2}$ $s^{-1}$ at room temperature. After one week, cells were harvested by filtration and fatty acid compositions were analyzed by gas chromatography.

*Rhodomonas salina* and *Amphidinium carterae* were determined to contain significant amount of SDA (~34% and 17%, respectively) (FIG. 1). In addition, both species were found to produce EPA and DHA, which are the main components of fish oil. Alpha-linolenic acid (ALA), the immediate precursor of SDA, was quite high in *R. salina*, but not in *A. carterae*, indicating a low level of activity for A-6 desaturase, which converts ALA to SDA.

Example 6

Growth Characterization

Light intensity and temperature are two most important environmental factors that affect the growth of microalgae. To determine the optimal growth conditions for *R. salina* and *A. carterae*, their requirements for light intensity and temperature were defined.

A. Growth Characteristics of *Rhodomonas salina*

1. Effects of light intensity on the growth of *R. salina*

Cells of *R. salina* were subjected to different light intensities, ranging from 20 to 200 µmol $m^{-2}$ $s^{-1}$ at room temperature. Samples were withdrawn daily and the growth of *R. salina* was measured as Chl-a and cell number.

Figure 2A:
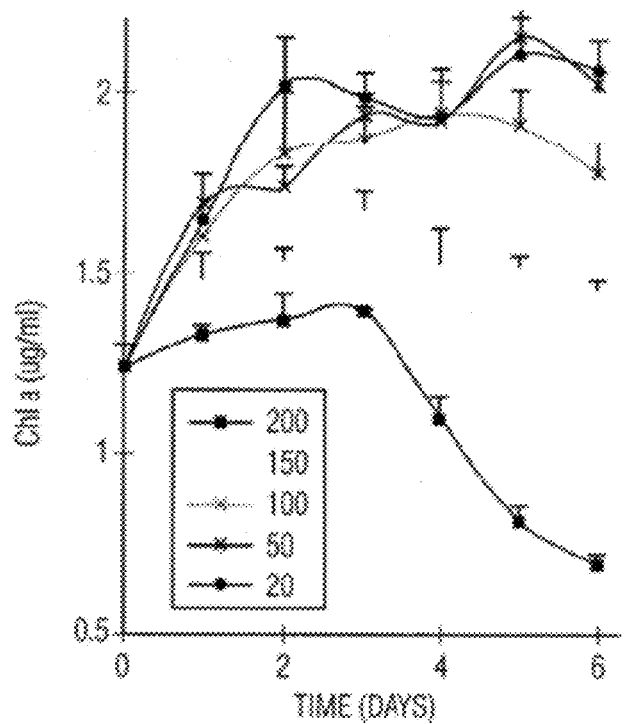
FIG. 2 shows the effect of light intensity on chlorophyll-a concentration (A) and cell number (B) in *Rhodomonas salina*.
Figure 2B:
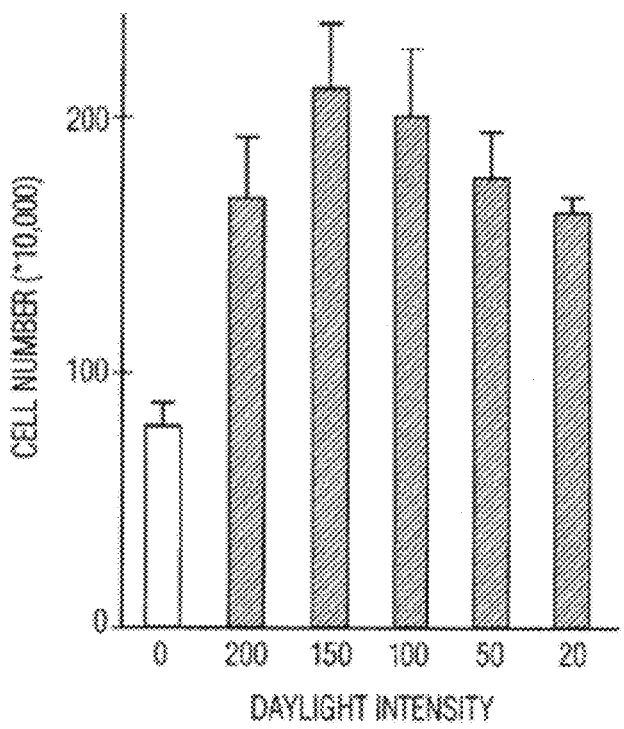

The optimal light intensity was below 100 µmol $m^{-2}$ $s^{-1}$ when growth was measured as an increase in Chl-a (FIG. 2A). A light intensity of 200 µmol $m^{-2}$ $s^{-1}$ caused a sharp decline after a moderate increase in the first three days. This result indicated that low light intensity was more favorable for *R. salina*, and high light intensity may cause photoinhibition leading to slower growth of *R. salina*. The same is true when cell number was used to assess the growth of *R. salina*. Thus, after one week, the highest cell concentration was obtained from the culture under a light intensity of 100 to 150 µmol $m^{-2}$ $s^{-1}$ (FIG. 2B). It should be noted that under these growth conditions, the final cell concentration reached over $2 \times 10^6$ cells/ml, which is ten times higher than results obtained in our preliminary studies. This improvement may be due to the change of culture medium from ES-enriched seawater medium to f/2 medium.

2. Effects of Temperature on the Growth of *R. salina*

Cells of *R. salina* were subjected to different temperatures which were controlled in a water bath at 14° C., 22° C., 28° C., and 34° C. under a light intensity of 50 µmol $m^{-2}$ $s^{-1}$. Samples were withdrawn daily and the growth of the *R. salina* was measured as Chl-a and cell number.

Figure 3A:
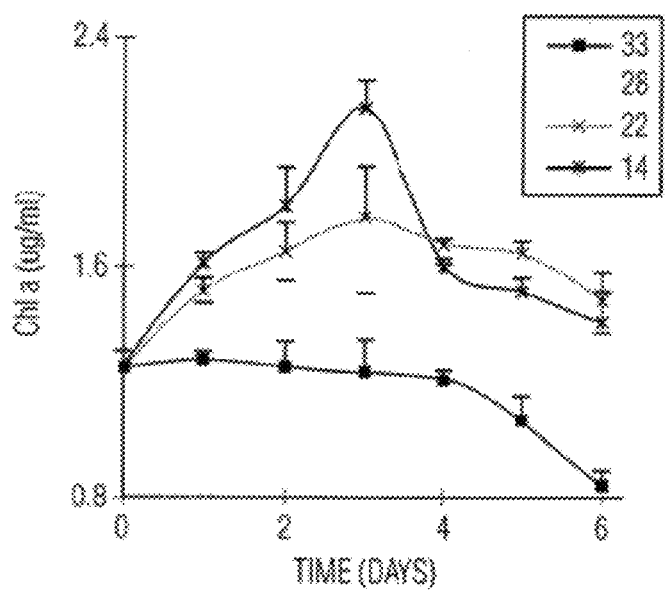
FIG. 3 shows the effect of temperature on chlorophyll-a concentration (A) and cell number (B) in *Rhodomonas salina*.
Figure 3B:
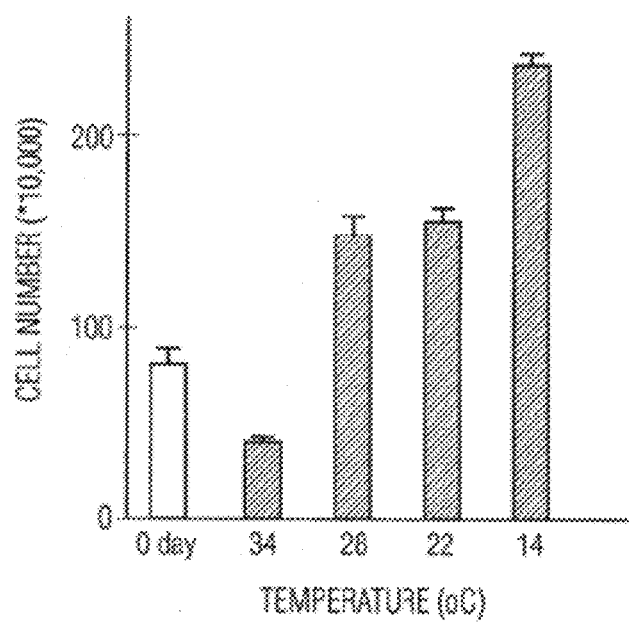

The optimal temperature for *R. salina* was found to be 14° C. when growth was measured as either an increase in Chl-a (FIG. 3A) or cell number (FIG. 3B). Growth was lower at 22° C. and 28° C. when compared to that at 14° C. No growth was detectable at 34° C., and declines in both Chl-a and cell number were observed after three days at this temperature. As a marine species, *R. salina* cannot tolerate the high temperature of 34° C., even 28° C. caused a significant slow down in growth.

Effects of Light Intensity and Temperature on Total Pigments Profiles

Figure 4A:
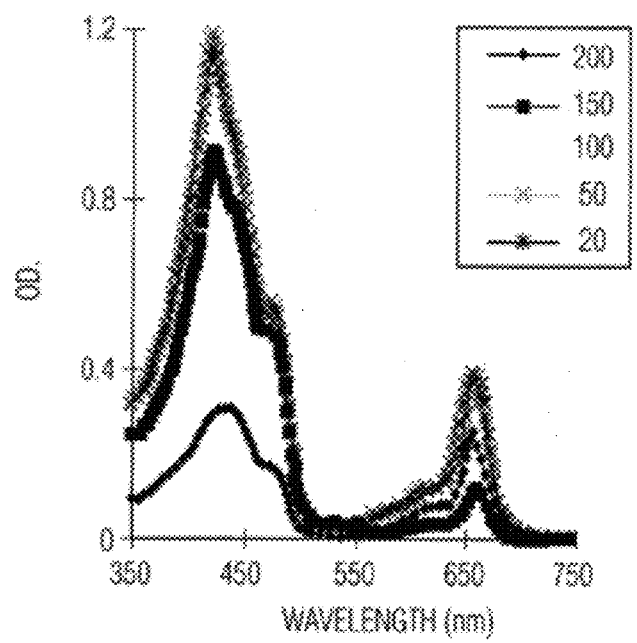
FIG. 4 shows the effect of light intensity (A) and temperature (B) on total pigment profile in *Rhodomonas salina*.
Figure 4B:
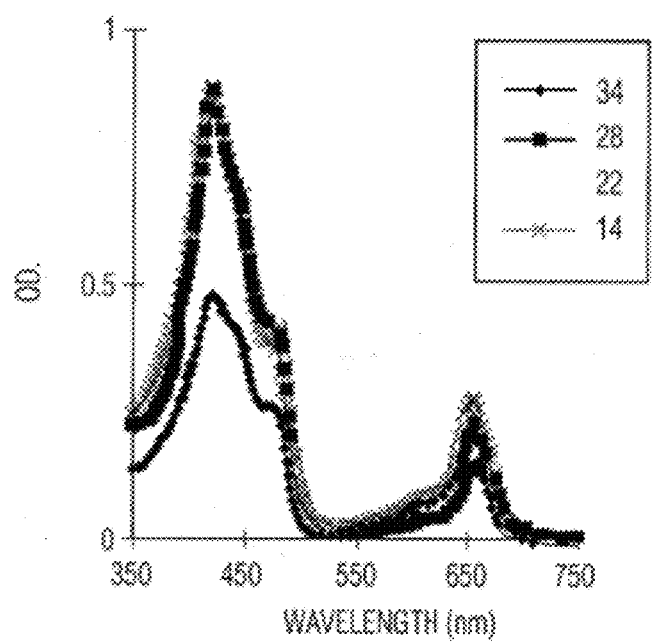

To further analyze the effects of light intensity and temperature on *R. salina*, cells grown under different light intensities and temperatures were harvested by filtration and total pigments were extracted with methanol. The pigment profiles are shown in FIG. 4. Two standard peaks of chlorophylls were observed at around 666 nm and 440 nm with a carotenoids shoulder at around 480 nm. Although the different light intensities and temperatures showed a clear impact on the absolute amounts of total pigments, the patterns of pigment profiles were not significantly different from each other, indicating that the light intensities and temperatures tested do not significantly affect the pigment profile.

B. Growth Characteristics of *Amphidinium carterae*

1. Effects of Light Intensity on *A. carterae*

Figure 5A:
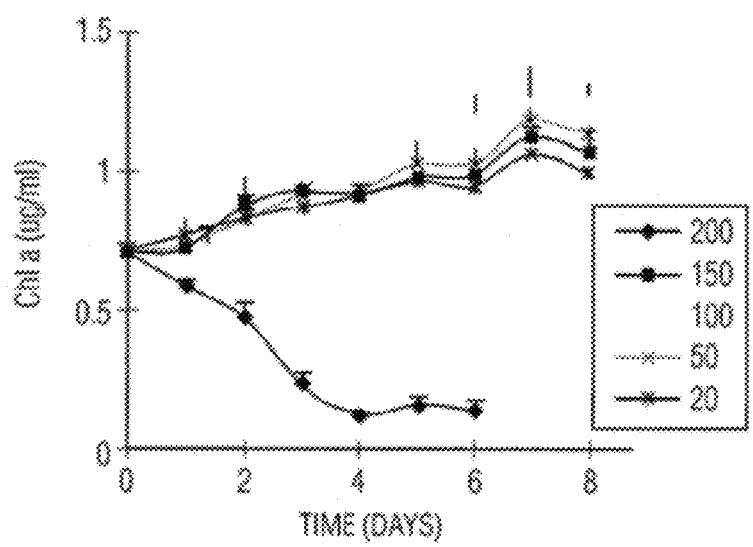
FIG. 5 shows the effect of light intensity on chlorophyll-a concentration (A) and cell number (B) in *Amphidinium carterae*.
Figure 5B:
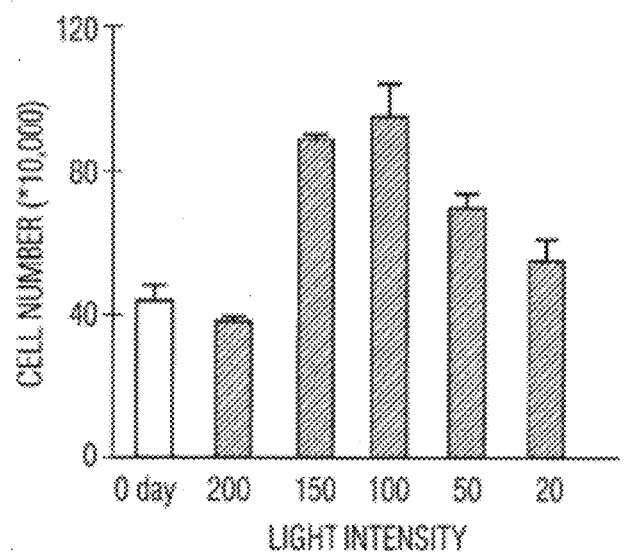

Cells of *A. carterae* were subjected to different light intensities, ranging from 20 to 200 µmol $m^{-2}$ $s^{-1}$ at room temperature. Samples were withdrawn daily from the culture flasks and the growth of the *A. carterae* was measured as Chl-a and cell number. When growth was measured as an increase in Chl-a, the light intensities from 20 to 150 µmol $m^2$ $s^{-1}$ had no significant effect on growth (FIG. 5A). In contrast, a light intensity of 200 µmol $m^{-2}$ $s^{-1}$ caused a rapid decline in Chl-a and eventually the bleaching of the culture. When the growth was measured as increase in cell number, the optimal light intensity was in the range of 100 to 150 µmol $m^{-2}$ $s^{-1}$. No growth was observed at a light intensity of 200 µmol m$^{-2}$ s$^{-1}$ (FIG. 5B). These results indicate that the microalgae *A. carterae* is very sensitive to high light intensity and can adapt to low light intensity for a reasonable growth rate.

2. Effects of Temperature on *A. carterae*

Figure 6A:
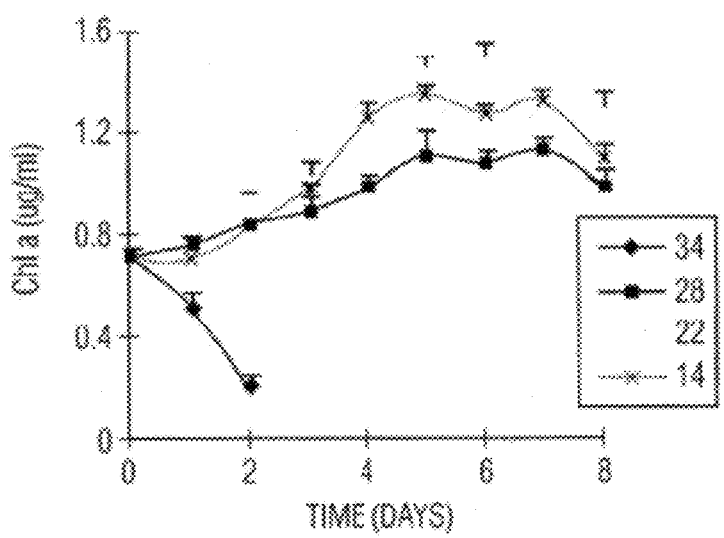
FIG. 6 shows the effect of temperature on chlorophyll-a concentration (A) and cell number (B) in *Amphidinium carterae*.
Figure 6B:
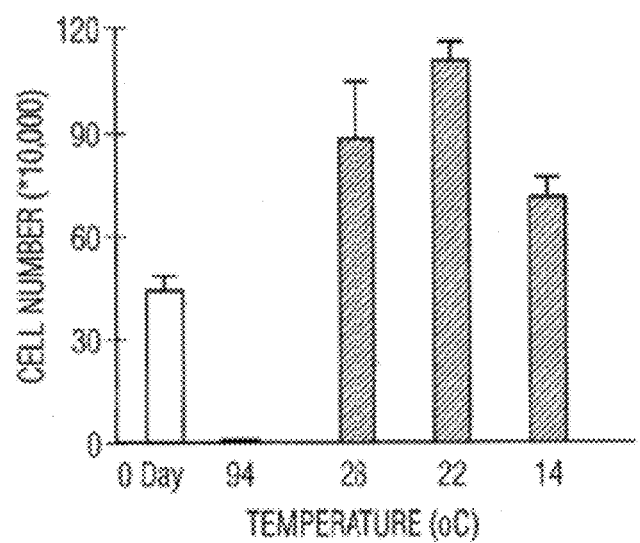

Cells of *A. carterae* were subjected to different temperatures controlled by a water bath at 14° C., 22° C., 28° C., 34° C. and under a light intensity of 50 µmol m$^{-2}$ s$^{-1}$. Samples from the cultures were withdrawn daily and the growth of the *A. carterae* was measured as Chl-a and cell number. The optimal temperature for *A. carterae* was found to be a temperature of 22° C. when growth was measured as an increase in Chl-a (FIG. 6A) and in cell number (FIG. 6B). At 14° C., the growth rate was similar to that at 22° C., but the final cell concentration was lower. No growth detected at 34° C.; instead a decline in both Chl-a and cell number was observed.

C. Effects of Light Intensity and Temperature on Total Pigments Profiles

Figure 7A:
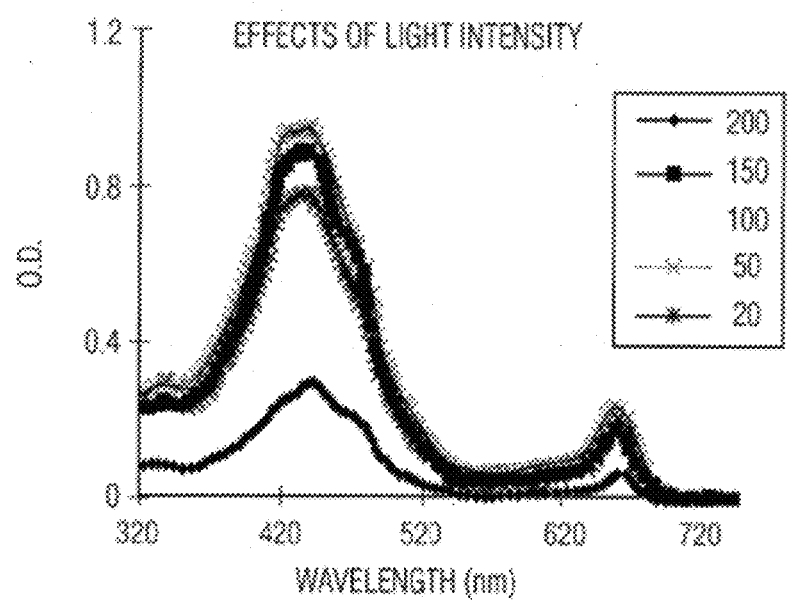
FIG. 7 shows the effects of light intensity (A) and temperature (B) on total pigment profile in *Amphidinium carterae*.
Figure 7B:
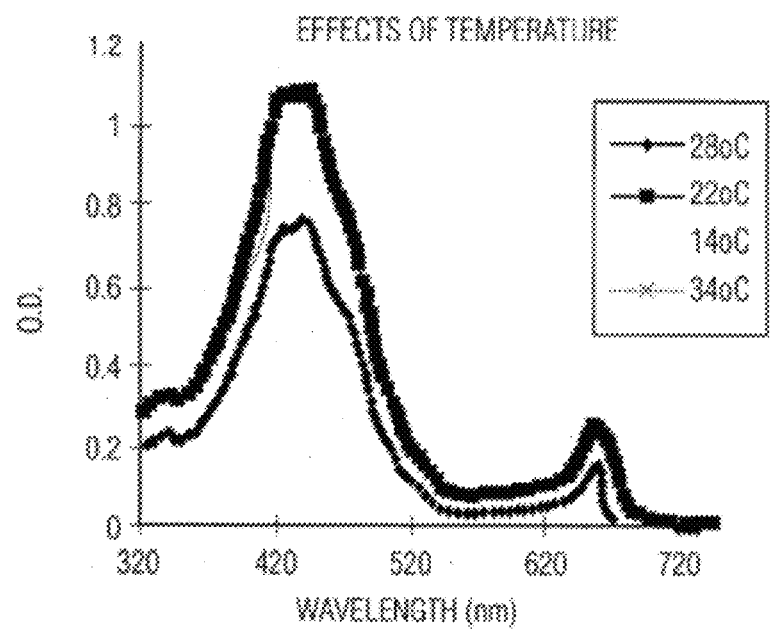

The pigment profiles of *A. carterae* are shown in FIG. 7. Similar to *R. salina*, the pigment profile pattern was not significantly different between the different treatments (light intensity and temperature); however, the absolute amount of total pigments was different under the different test conditions.

D. Cytotoxicity Tests for *R. salina* and *A. carterae*

Cytotoxicity of marine algae is a concern, especially when the algae are used for aquaculture feed or human nutrition. Therefore, *R. salina* and A. Carterae were tested to determine whether they were toxic or not. A brine shrimp cytotoxicity assay was employed for the test and another marine microalga, Navicular-like diatom (NLD), was used as negative control. Microalgae cells at various concentrations were distributed in wells of 96-well plates, newly hatched brime shrimp larvae (nauplii) were introduced to each well at a density around 10 nauplii per well. Wells containing medium only without microalgae served as a background control. The numbers of live nauplii were counted daily to monitor the survival rate.

Figure 8:
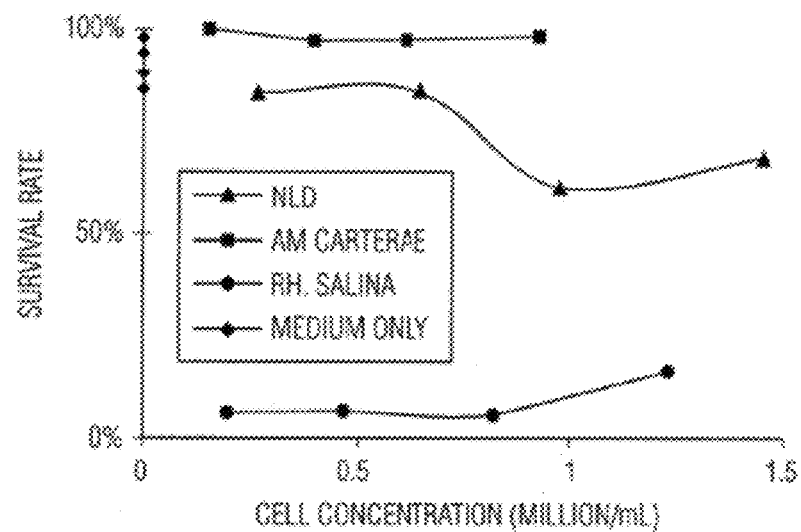
FIG. 8 presents the results of the cytotoxicity tests of *Rhodomonas salina* and *Amphidinium carterae*.

As shown in FIG. 8, *R. salina* did not show any adverse effect on the nauplii, which continued to grow for several days until cells of *R. salina* were depleted. The NDL showed a survival rate of 70%~90%, which was similar as the rate obtained from background (medium only no microalgae). For *A. carterae*, the results were quite surprising: after 24 hours more than 50% nauplii were dead; after 48 hours less than 10% survived. It is clear that *A. carterae* is toxic to brime shrimp nauplii. The mechanism of the toxicity was not determined. These results demonstrate that *R. salina* is not cytotoxic to brime shrimp, while *A. carterae* showed a clear toxicity.

Example 7

Determining the Conditions for Fatty Acids Accumulation

Based on results obtained from cytotoxicity tests, *R. salina* was chosen for further characterization on fatty acids accumulation and scale-up production. The following experiments were designed to test for methods that can increase the accumulation of fatty acids in *R. salina*.

1. Effect of Culture Stage of *R. salina*

A typical batch culture of microalgae includes three stages: (1) a lag phase—the beginning of the culture, an adaptation period with low growth rate; (2) an exponential phase, the fastest growing period with rapid cell division; and (3) a stationary phase—due to nutrient depletion, the growth slows down accompanied by accumulation of secondary metabolites.

The following experiments were carried out in order to determine the growth stage during which *R. salina* accumulates large amounts of fatty acids. *R. salina* cells were inoculated into f/2 growth medium under the previously determined optimal light intensity and temperature (22° C. and 100 µmol m$^{-2}$ s$^{-1}$). Cells were harvested at exponential phase and stationary phase, respectively, for fatty acids analysis.

Figure 9:
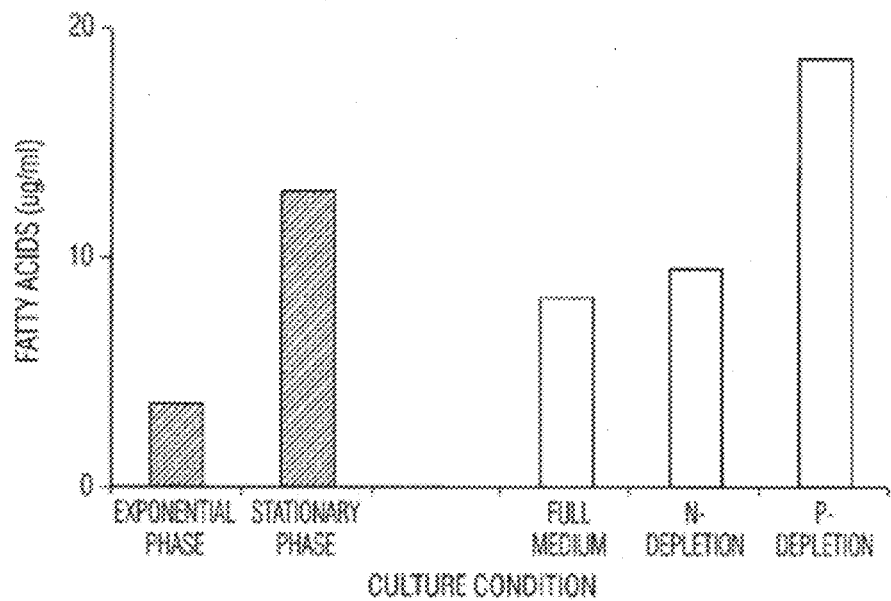
FIG. 9 shows the effects of culture stage and nutrition on fatty acid accumulation in *Rhodomonas salina* grown at 28° C.

*R. salina* cells at stationary phase were determined to contain three times higher fatty acids levels than cells at exponential phase (FIG. 9; blue bars). This result is of interest for designing a production strategy for fatty acids from *R. salina*. For example, cells can be first cultivated under optimal conditions to obtain maximum biomass, which can be maintained in stationary phase to accumulate the desirable fatty acids prior to harvesting.

2. Effect of Nutrition Depletion

An effective method of inducing fatty acids accumulation in microalgae is to subject the cells to nutritional depletion, most commonly nitrogen or phosphorus starvation (Cohen, Z. and C. Ratledge, *Single Cell Oils*, American Oil Chemists' Society, Champaign, Ill., USA (2005)). To test the feasibility of this method, *R. salina* cells were washed three times with nitrogen-free or phosphorus-free f/2 medium, and then grown in the same medium for six days. Cells were harvested at the end of six days and fatty acid levels were measured (FIG. 9, right side, yellow bars).

As compared to the control, nitrogen starvation did not induce a significant accumulation of fatty acids. In contrast, phosphorus-free medium induced a significant increase in fatty acid content. This result suggests that for the mass production of SDA, phosphorus starvation can be employed to induce the accumulation of fatty acids.

3. Effect of Temperature

Temperature is one the factors that can affect fatty acid accumulation in microalgae. Thus, in the following example, the effects of temperature on the accumulation of SDA in *R. salina* and *A. carterae* were studied.

Figure 10:
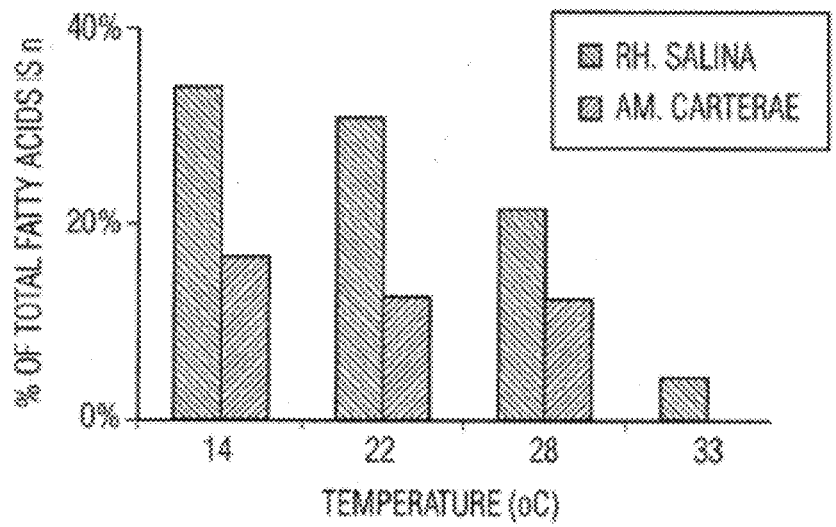
FIG. 10 shows the effect of temperature on SDA content *Rhodomonas salina* and *Amphidinium carterae*.
Figure 11:
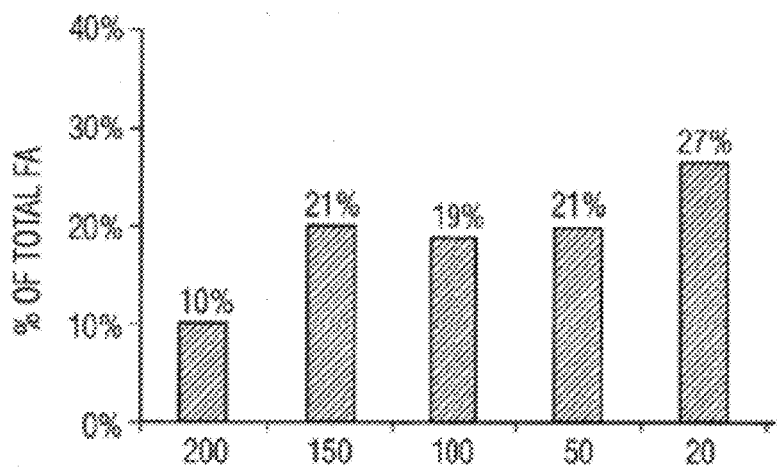
FIG. 11 shows the effects of light intensity on SDA content in *Rhodomonas salina*.

*R. salina* and *A. carterae* cells were inoculated in the full f/2 growth media under a low light intensity of 50 µmol m$^{-2}$ s$^{-1}$ and subjected to a temperature of 14° C., 22° C., 28° C., or 33° C. After one week of growth, cells were harvested by filtration and lipids were extracted and analyzed for fatty acid content. As shown in, FIG. 10, the SDA content of *R. salina* was determined to be significantly higher at the lower temperatures of 14° C. and 22° C. than at the higher temperature of 33° C. (FIG. 10). A similar trend was observed for *A. carterae*, which has less overall SDA content compared to *R. salina*. The effects of light intensity on SDA content in *Rhodomonas salina* is shown in FIG. 11.

Example 8

Lipid Profiles of Cultured Microalgae of the Genus *Rhodomonas*

To further characterize and determine PUFA profiles, various cultures of microalgae belonging to the genus *Rhodomonas* were grown under different culture conditions and their fatty acid content determined qualitatively and quantitatively.

Strains: *Rhodomonas* strains were obtained from CCMP (Table 2).

TABLE 2

*Rhodomonas* strains and corresponding culture medium

| | Name | CCMP strain number | Culture Medium |
|---|---|---|---|
| *Rh. salina* | 1Rsal | 272 | L1 |
| | 2Rsal | 273 | L1 |
| | 3Rsal | 322 | L1 |
| | 4Rsal | 323 | L1 |
| | 5Rsal | 1170 | L1 |
| | 6Rsal | 1171 | L1 |
| | 7Rsal | 1319 | L1 |
| | 8Rsal | 1419 | L1 |
| | 9Rsal | 1420 | L1 |
| *Rh.* sp. | 10Rsp | 740 | Prov50 |
| | 11Rsp | 755 | Prov |
| | 12Rsp | 757 | h/2 |
| | 13Rsp | 762 | K |
| | 14Rsp | 766 | L1 |
| | 15Rsp | 768 | f/2 |
| | 16Rsp | 1533 | Prov50 |
| | 17Rsp | 2005 | L1 |
| | 18Rsp | 2045 | Prov50 |

Antibiotic treatment (Isolation step): Algal strains 4Rsal, 5Rsal, 9Rsal, 12Rsp, and 16-Rsp were subjected to antibiotic treatment. A dilute culture of strain 12Rsp was incubated overnight (ambient room temperature, 13/11 light/dark) with a 1/1000 dilution of sterile tryptic soy broth (to promote bacterial growth, thereby increasing susceptibility to antibiotics). The next day, a combination of gentamicin (80 µg/ml), vancomycin (50 µg/ml) and clindamycin (20 µg/ml) was added and the culture was treated for 48 hs. The treated culture was diluted (1/10 and 1/100) in to antibiotic-free medium. Samples of these dilutions were streaked on trypticase soy agar (prepared in seawater-based medium) fortified with tryptone, yeast extract and glucose to evaluate bacterial growth (ambient room temperature, 13/11 light/dark). The diluted culture was also streaked on sheep blood agar and grown at 37° C. No bacteria grow on either of these enriched solid media.

With respect to strains 4Rsal, 5Rsal, 9Rsal, and 16-Rsp, these strains were (1) treated 48 hr with antibiotics in the presence of a 1/1000 dilution of tryptic soy broth (to promote bacterial growth, thereby increasing susceptibility to antibiotics); (2) diluted in antibiotic-free medium; and then (3) evaluated for bacterial grown on trypticase soy agar at least twice. Strains 9Rsal and 16Rsp were treated with a combination of gentamicin (80 µg/ml), vancomycin (504 ml) and clindamycin (20 µg/ml). Strain 4Rsal was treated with the aforementioned antibiotic cocktail, then treated with ceftazidime (100 µg/ml). Strain 5Rsal was subjected to the gentamicin/vancomycin/clindamycin protocol, then further treatment with ciprofloxacin (100 µg/ml), meropenem (100 µg/ml), and rifampin (50 µg/ml).

Algal Cultivation: Cells were grown in suspension in a seawater-based media at room temperature (23-25° C.) with a 13 hr/11 hr light/dark cycle. The light sources were equipped with SoftWhite fluorescent bulbs, which provided about 600 to 1000 lux (1×) at all points in the incubator. As shown by Tables 3 and 4, the media was prepared in filtered seawater and contained (per liter): 0.075 g $NaNO_3$, 0.005 g $NaH_2PO_4 \cdot H_2O$, medium-specific trace mineral mixes, vitamin mixes, and about 0.027 to 0.0027 g $NH_4Cl$ (depending on the strain).

TABLE 3

Algal Media

| Component | [Stock] | L1 [Final] | h/2 [Final] | f/2 [Final] | Prov50 [Final] | Prov [Final] | K [Final] |
|---|---|---|---|---|---|---|---|
| Filtered seawater | | 1x | 1x | 1x | 1x | 1x | 1x |
| $NaNO_3$ | 75 g/L (883 mM) | 883 µM | 883 µM | 883 µM | 883 µM | 883 µM | 883 µM |
| $NaH_2PO_4 \cdot H_2O$ | 5 g/L (36.3 mM) | 36.3 µM | 36.3 µM | 36.3 µM | 36.3 µM | 36.3 µM | — |
| $Na_2$ β-glycero-phosphate•$6H_2O$ | 2.16 g/L (10 mM) | — | — | — | — | — | 10 µM |
| Tris, pH 7.2 | 121. g/L (1M) | — | — | — | — | — | 1 mM |
| $H_2SeO_3$ | 1.29 mg/L (10 µM) | — | — | — | — | — | 0.01 µM |
| L1 Trace mineral mix[a] | 1000x | 1x | — | — | — | — | — |
| f/2 Trace mineral mix[a] | 1000x | — | 1x | 1x | 1x | 1x | — |
| K Trace mineral mix[a] | 1000x | — | — | — | — | — | 1x |
| Soil Extract[b] | | — | — | — | 1x | 15 ml/L | — |
| Autoclave on liquid cycle (20 min, 121° C., 2 atm) | | | | | | | |
| f/2 vitamin soln[a,c] | 2000x | 1x | 1x | 1x | 1x | 1x | 1x |
| $NH_4Cl$[c] | 26.8 g/L (500 mM) | — | 500 µM | — | 50 µM | 50 µM | 50 µM |

[a]See Table 3 for composition.
[b]Obtained from CCMP.
[c]Added after autoclaving and cooled; Allowed autoclaved medium to stand overnight at room temperature to allow re-equilibration with $CO_2$.

TABLE 4

Stock Trace Mineral And Vitamin Mixes

| Component | Stock soln | Stock Trace Mineral Mixes ||| Stock Vitamin |
| | | L1 trace mineral mix[a,b] | f/2 trace mineral mix[a,b] | K trace mineral mix[a,b] | Soln f/2 vitamin mix[a,c] |
|---|---|---|---|---|---|
| Vitamin $B_{12}$ | 1 g/L | — | — | — | 1 ml |
| Thiamine | 0.1 g/L | — | — | — | 10 ml |
| Biotin | — | — | — | — | 200 mg |
| $Na_2 EDTA \cdot 2H_2O$ | — | 4.36 g | 4.36 g | 41.6 g | — |
| $FeCl_3 \cdot 6H_2O$ | — | 3.15 g | 3.15 g | 3.15 g | — |
| $NaMoO_4 \cdot 2H_2O$ | 6.3 g/L | — | 1 ml | 1 ml | — |
| $NaMoO_4 \cdot 2H_2O$ | 19.9 g/L | 3 ml | — | — | — |
| $ZnSO4 \cdot 7H_2O$ | 22 g/L | 1 ml | 1 ml | 1 ml | — |
| $CoCl_2 \cdot 6H_2O$ | 10 g/L | 1 ml | 1 ml | 1 ml | — |
| $MnCl_2 \cdot 4H_2O$ | 180 g/L | 1 ml | 1 ml | 1 ml | — |
| $CuSO_4 \cdot 5H_2O$ | 9.8 g/l | — | 1 ml | 1 ml | — |
| $CuSO_4 \cdot 5H_2O$ | 2.45 g/L | 0.25 ml | — | — | — |
| $H_2SeO_3$ | 1.29 mg/L | 1 ml | — | — | — |
| $NiSO4 \cdot 6H_2O$ | 2.7 g/L | 1 ml | — | — | — |
| $Na_3VO_4$ | 1.84 g/L | 1 ml | — | — | — |
| $K_2CrO_4$ | 1.94 g/L | 1 ml | — | — | — |

[a]g/L deionized water
[b]Added or dissolved componet in final of 1 L deionized water
[c]Added component to final volume of 1 L deionized water and sterilized by filtration Vitamins and $NH_4Cl$ were added from sterile stocks after autoclaving. Cells were grown in autoclaved glass tubes (20× 125 mm) or foil-capped glass flasks (125-500 ml) in static suspension with intermittent gentle mixing (by swirling) every 2-4 days. Cells were subcultured using standard aseptic techniques. All cultures and spent media were autoclaved prior to disposal.

Enumeration and Assessment of Growth Rate: Cell growth was monitored by visual inspection for increased color of the suspension (red or brown depending on the strain) of these pigmented organisms. Cells were enumerated by counting a suitable dilution (25-30 cells per 10 squares) with a hemocytometer at 2-3 day intervals. Since these are flagellated organisms, an estimate of cell viability was monitored microscopically in suspensions diluted in seawater. More precise enumeration was performed in samples diluted in phosphate buffered saline (PBS), which rendered cells of most strains immobile. Growth rates were expressed as doubling time (DT) estimated from the slope of a semi-log plot of cell counts as a function of days in culture using the equation of a line (y=ax+b), when y=log 2 (doubling of cell density) then b=0, so log 2=slope×DT. Solving for DT, then DT=0.301/slope, where log 2=0.301.

Assessment of Fatty Acid Content: Total lipids were extracted from about 5-10 million cells per sample by the method of Bligh and Dyer, Can. J. Biochem. Physiol., 37:911-7 (1959). Cells in suspension were collected by centrifugation (1000×g; 20 min; 25° C.) in 16×125 mm glass screw capped (Teflon liner) tubes; and the cell-free medium was aspirated and discarded. The cell pellet was suspended in 0.8 ml deionized $H_2O$, lysed with the addition of 2 ml methanol and extracted with the addition of 1 ml chloroform. Methanol was added drop wise, if necessary to achieve a monophase. The phases were split by the addition of 1 ml dilute $H_2SO_4$ (0.25 ml concentrated $H_2SO_4$/500 ml deionized $H_2O$) and 1 ml chloroform followed by through mixing and centrifugation (400×g, 10 min, 4° C.). Total lipids were recovered in the bottom chloroform phase and transferred to a clean 16×125 mm glass screw capped tube containing 10 μg of internal standard (triheptadecanoin). The chloroform extract was dried under a stream of nitrogen gas. Total fatty acids were saponified by the addition of 1 ml ethanol and 0.1 ml 50% KOH (w/v). Capped tubes were heated at 60° C. in a heating block for 10 min, before vortexing followed by an additional 20 min at 60° C. After the tubes had cooled, neutral lipids and cholesterol were extracted by the addition of 2 ml hexane and 1 ml deionized $H_2O$. After vigorous mixing, the phases were split by centrifugation (400×g, 10 min, 4° C.) and the upper (hexane) phase was aspirated and discarded. The free fatty acids were extracted from the lower aqueous with the addition of 2 ml hexane and 0.1 ml glacial acetic acid followed by vigorous mixing and centrifugation (400×g 10 min, 4° C.). The fatty acid-containing upper phase (hexane) was transferred to a clean 13×100 mm glass screw capped (Teflon liner) tube. The hexane extract was dried under a stream of nitrogen gas. Fatty acids were prepared for derivatization by the addition of 1 ml 0.5M NaOH (in methanol) to the dried extract and heating for 5 min at 100° C. Fatty acids were derivatized in the presence of boron trifluoride (1 ml 14% $BF_3$ in methanol per tube) and heating for 5 min at 100° C. The fatty acids methyl ester (FAME) derivatives were extracted by the addition of 2 ml hexane and 2 ml saturated NaCl (36 g/100 ml deionized $H_2O$) followed by through mixing and centrifugation (400×g, 10 min, 4° C.). The upper phase (hexane) was transferred to clean 13×100 mm tube. The hexane extract was dried under a stream of nitrogen gas, redissolved in isooctane (0.25-0.5 ml) and transferred to a clean 1 ml crimp top vial and sealed.

The fatty acid methyl esters were separated and quantified by gas liquid chromatography (GLC) on a CP-Select CB for FAME capillary column, 100 m×0.25 mm id, (Varian) installed in a temperature programmed Agilent 6890N gas chromatograph equipped with an on-column capillary inlet, flame ionization detector (FID), and Agilent 7683B autosampler/injector. The chromatographic conditions were: $H_2$ carrier gas, 20 psi head pressure; nitrogen make-up gas, 25 ml/min; inlet temperature at 3° C. above the oven temperature; and FID at 230° C. The oven temperature was programmed to begin at 90° C. and hold for 0.5 min, increase at 10° C. per min to 150° C., increase at 2.5° C. per min to 200°

C., increase at 1.5° C. per min to the final temperature, 220° C., and hold at 220° C. for 20 min. Total run time is 60 min plus a 5-min equilibration period between runs.

Chromatographic data collection and analysis was via a USB serial adapter to a 2.8 GHz Intel Pentium 4 personal computer running Chrom Perfect™ Spirit Chromatography Data System, Version 5.5 (Justice Laboratory Software) in Microsoft Windows XP. Each chromatogram was examined for correct identification of constituent fatty acids and quality control. Data was reported out in Microsoft Excel as the amount of each identified fatty acid per sample. Calibrations for the major fatty acids were constructed by the chromatography software and updated by periodic injections of standard FAME solutions of known composition Nutrient Assays: Medium phosphate was measured using a routine colorimetric assay. Dedicated tubes (16×125 mm glass screw capped (Teflon liner) tubes) and caps were used for this assay that had not been washed in phosphate-containing detergent. A 1 mM stock solution of sodium phosphate (dibasic) was used to construct a standard curve (0, 2, 5, 10, 20, 40, 60 nmole/tube in a 60 µl volume) in 904 µl seawater in duplicate. Deionized $H_2O$ (60 µl) was added to duplicate sample tubes followed by 900 µl cell-free medium. Three additions were made to each standard and sample tube followed by vortex mixing. These additions were: 150 µl perchloric acid (60%), 167 µl 2.5% ammonium molybdate and 167 µl 10% ascorbic acid (w/v; freshly prepared). Tubes were capped and incubated at 50° C. for 15 min. After tubes had cooled, the absorbance at 820 nm was measured against deionized $H_2O$, Sample phosphate concentration was estimated from the standard curve.

Nitrate was estimated using an ultraviolet spectrophotometric method. A 1 mM stock solution of sodium nitrate was used to construct a standard curve (0, 5, 10, 20, 30, 40, 50, 60 µM in 5 ml deionized $H_2O$ in duplicate). Cell-free medium and seawater (blank) were diluted 1 to 40 in 2 ml deionized $H_2O$ (in triplicate or quadruplicate). The absorbance of standards and diluted samples at 220 nm was measured against deionized $H_2O$. After subtraction of the seawater blank, the sample nitrate concentration was estimated from the standard curve.

Figure 12:
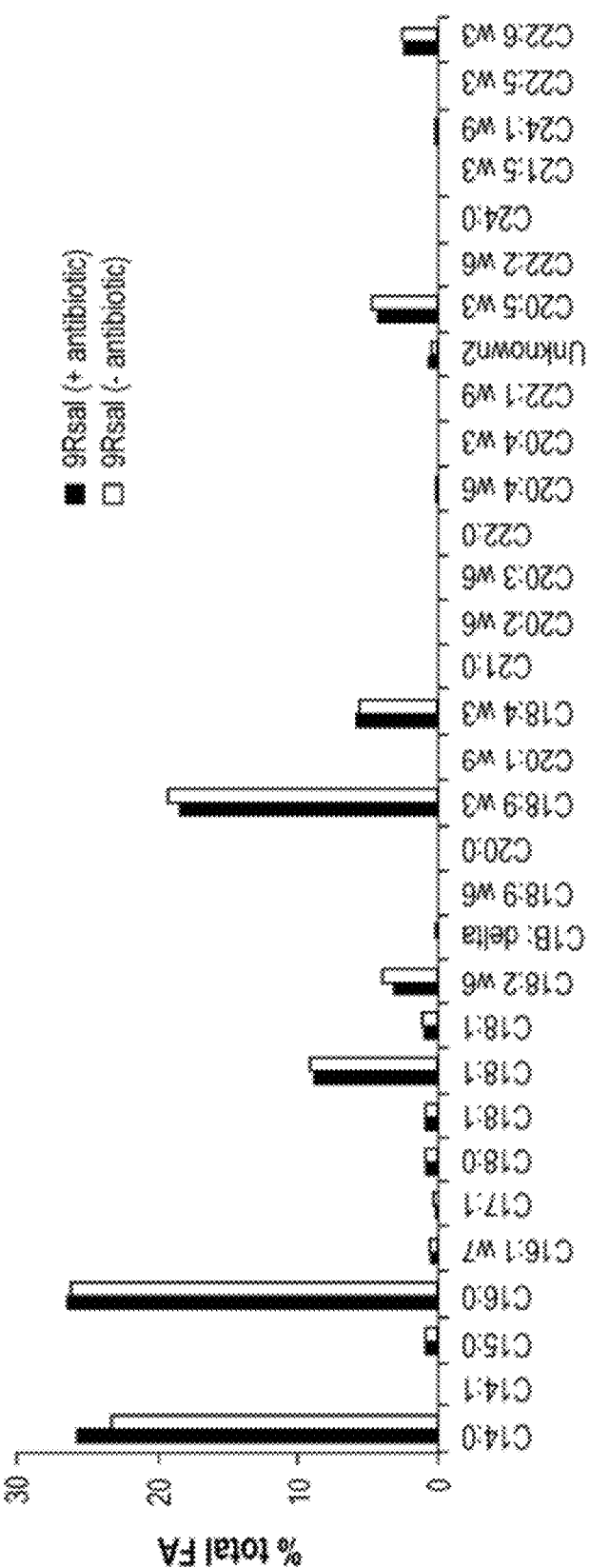
FIG. 12 shows fatty acid ("FA") profile of strain 9Rsal cultured before (□) and after (■) antibiotic treatment.

As shown in FIG. 12, antibiotic treatment did not change fatty acid profile as determined for 9Rsal, for example.

Figure 13A:
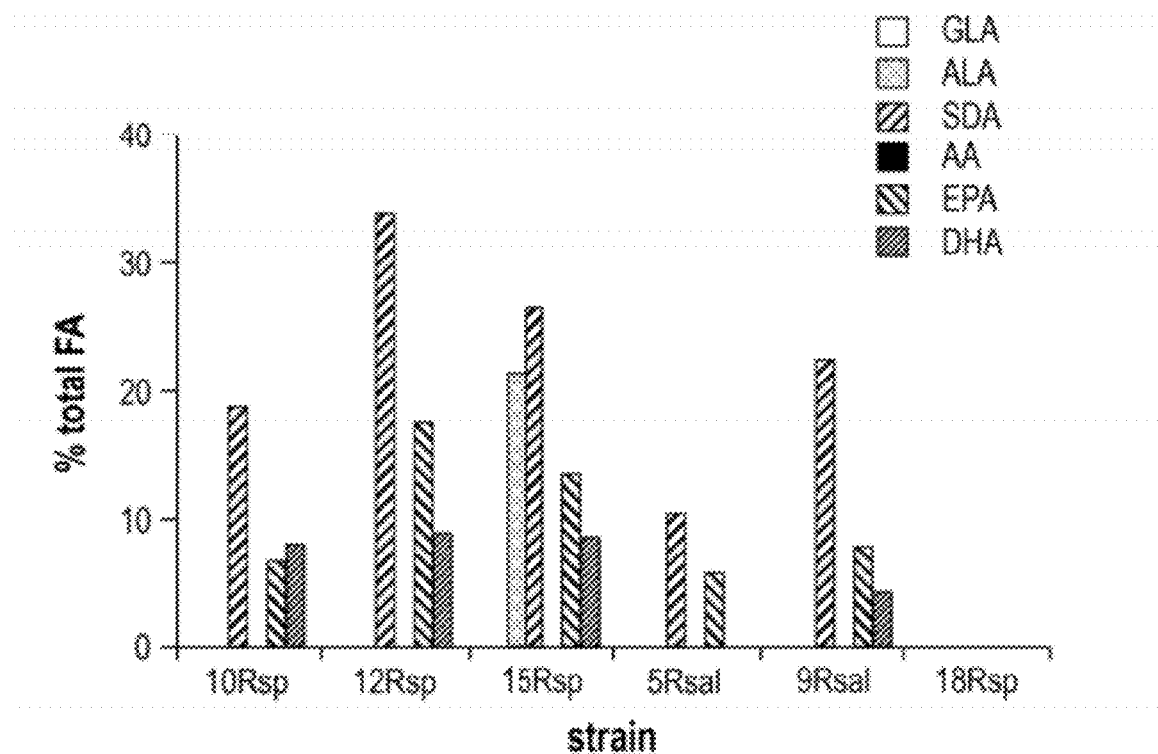
FIG. 13 shows FA profile of various *Rhodomonas* strains determined at a stationary phase: (A) Specific polyunsaturated FAs; and (B) Sum of unsaturated and monounsaturated FAs. Data is not normalized to number of cells.
Figure 13B:
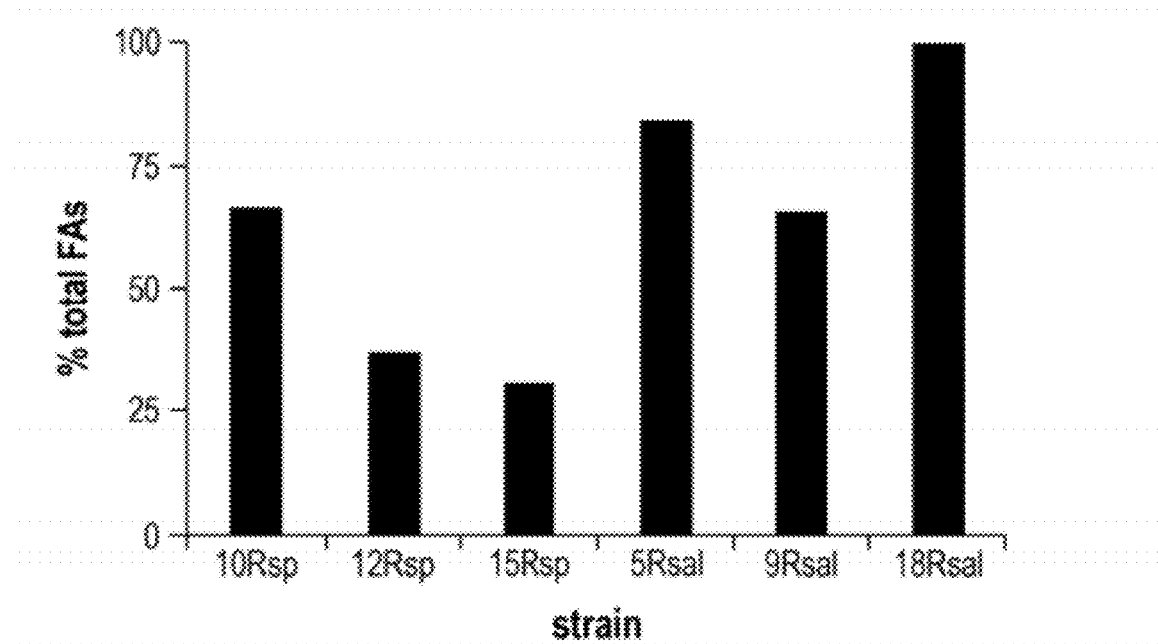
Figure 14A:
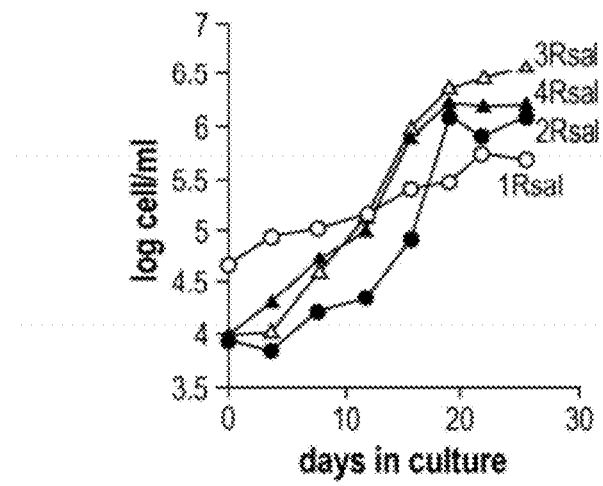
FIG. 14 shows growth characteristic of strains of *Rhodomonas*.
Figure 14B:
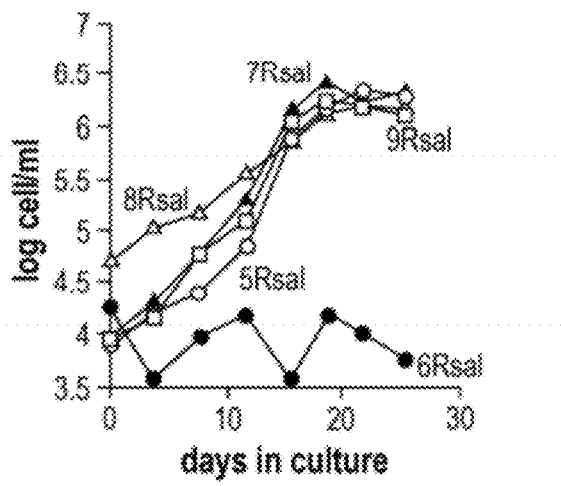
Figure 14C:
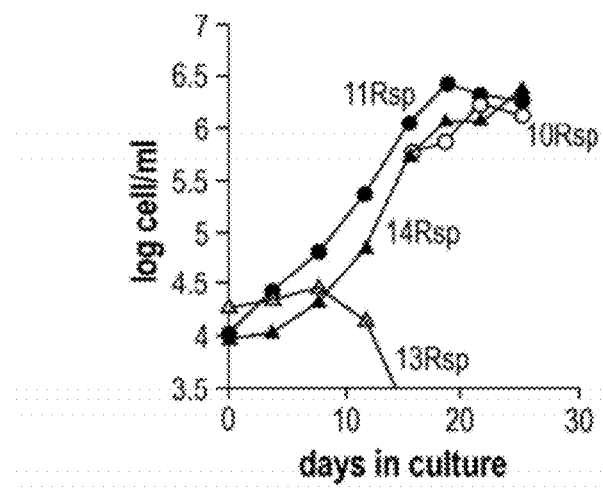
Figure 14D:
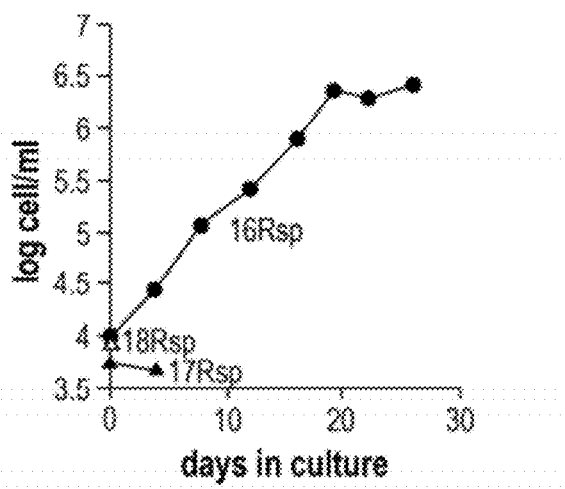
Figure 14E:
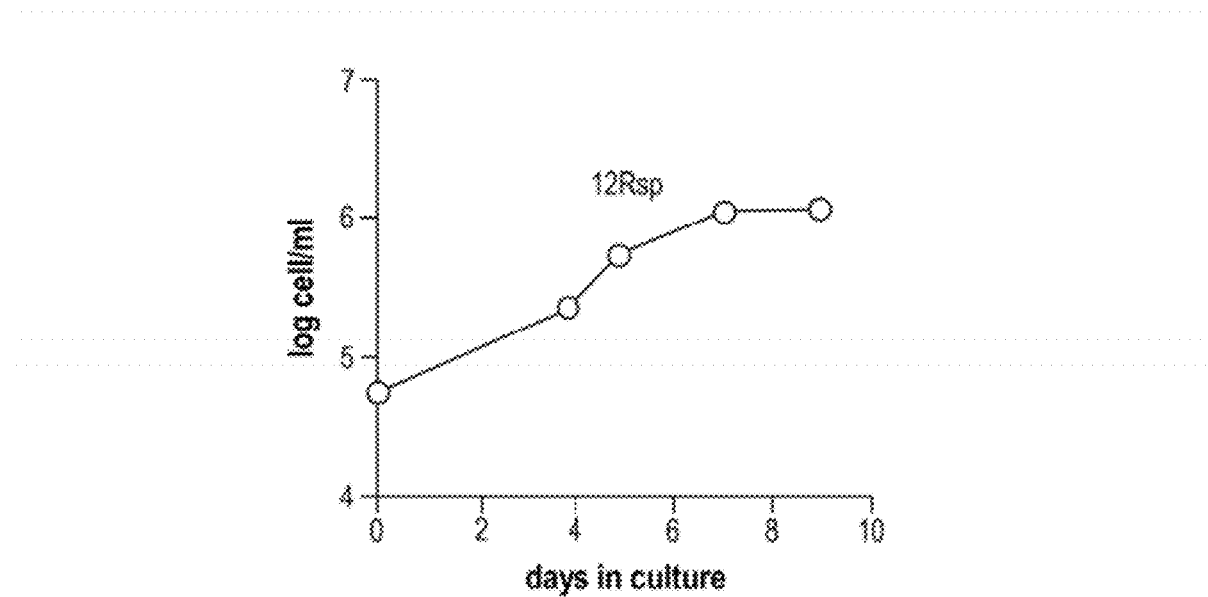

FIG. 13 shows a fatty acid (FA) analysis for strain of Rhodomonas as determined at a stationary phase (data not normalized to the number of cells). The results show a relatively high content (33.8%; FIG. 13A) of SDA and a relatively low content (36.7%; FIG. 13B) of unsaturated and mono-saturated FAs for strain 12Rsp.

Example 9

Growth Characteristics and Lipid Profiles of Cultured Microalgae of the Genus Rhodomonas All strains, except for strains 1Rsal, 6Rsal, 8Rsal, 13Rsp, and 17Rsap, were inoculated, in triplicate glass culture tubes, in 5 ml of the appropriate CCMP recommended medium at a density of ~$10^4$ cells/ml. For strains 1Rsal, 6Rsal, 8Rsal, 13Rsp, and 17Rsap, 4 ml of the original CCMP suspensions was aliquoted in triplicate to glass culture tubes. All tubes were place in incubator, grown at room temp (23-24° C.), and illuminated with a 23 W compact fluorescent bulb on a 13 hr light (7 am-8 pm)/11 hr dark cycle. One of the triplicate tubes of each strain was counted at 3-4 day intervals. A day or so after the receipt of strains, a second pair of tubes was inoculated for each of the more dense strains as a back source of cells. These cultures were later used for FA analysis. The results are shown in Table 5.

TABLE 5

Microalgae cell doubling time.

| | Name | CCMP strain number | Doubling Time (days) |
|---|---|---|---|
| Rh. salina | 1Rsal | 272 | 6.8 |
| | 2Rsal | 273 | 2.4 |
| | 3Rsal | 322 | 1.9 |
| | 4Rsal | 323 | 2.5 |
| | 5Rsal | 1170 | 2.5 |
| | 6Rsal | 1171 | nd |
| | 7Rsal | 1319 | 2.2 |
| | 8Rsal | 1419 | 4.1 |
| | 9Rsal | 1420 | 2.3 |
| Rh. sp. | 10Rsp | 740 | 2.3 |
| | 11Rsp | 755 | 2.3 |
| | 12Rsp | 757 | 1.9 |
| | 13Rsp | 762 | nd |
| | 14Rsp | 766 | 2.1 |
| | 15Rsp | 768 | nd |
| | 16Rsp | 1533 | 2.5 |
| | 17Rsp | 2005 | nd |
| | 18Rsp | 2045 | nd |

As shown in Table 5, doubling times (DTs) ranged from 1.9 to 6.8 days with most strains doubling about every 2.3 days. At the culture volumes (5-10 ml) utilized in this set of experiments, most viable strains did not exhibit a pronounced lag time in growth when first inoculated into medium (FIG. 14).

For FA content analysis, samples (5-10 million cells/sample) of each strain at harvest densities from ~0.3 to 3.5 million cells/ml, low to high, respectively, were extracted, processed, and analyzed for FA content. The harvest densities of the strains is shown in Table 6.

TABLE 6

Cell density at harvest.

| | Name | CCMP strain number | [a]Number of cells/ml (Low) | [a]Number of cells/ml (High) |
|---|---|---|---|---|
| Rh. salina | 2Rsal | 273 | $0.9 \times 10^6$ | nd |
| | 3Rsal | 322 | $1.2 \times 10^6$ | $3.5 \times 10^6$ |
| | 4Rsal | 323 | $1.06 \times 10^6$ | $1.41 \times 10^6$ |
| | 5Rsal | 1170 | $0.86 \times 10^6$ | $2 \times 10^6$ |
| | 7Rsal | 1319 | $1.16 \times 10^6$ | $2.0 \times 10^6$ |
| | 8Rsal | 1419 | $1.0 \times 10^6$ | $1.5 \times 10^6$ |
| | 9Rsal | 1420 | $1.2 \times 10^6$ | $1.25 \times 10^6$ |
| Rh. sp. | 10Rsp | 740 | $1.18 \times 10^6$ | $1.45 \times 10^6$ |
| | 11Rsp | 755 | $1.7 \times 10^6$ | $1.7 \times 10^6$ |
| | 12Rsp | 757 | $0.34 \times 10^6$ | $2.05 \times 10^6$ |
| | 14Rsp | 766 | $1.2 \times 10^6$ | $2.1 \times 10^6$ |
| | 16Rsp | 1533 | $1.08 \times 10^6$ | $2.52 \times 10^6$ |

[a]At time of harvest.

Figure 15:
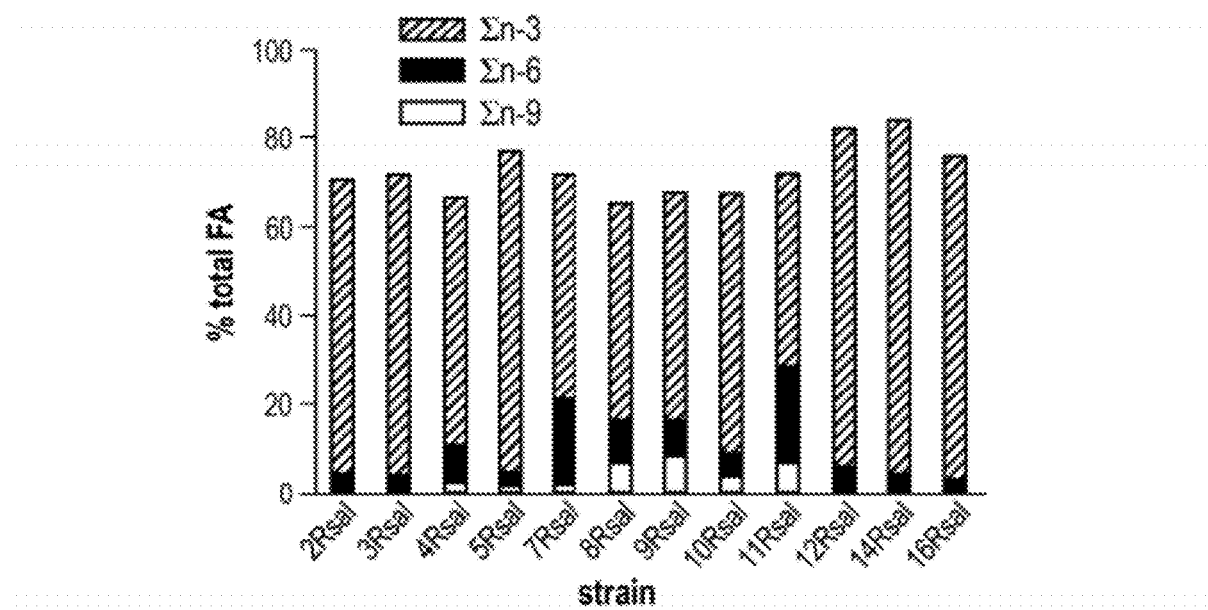
FIG. 15 shows content of unsaturated FAs (omega-3 (Σn-3), omega-6 (Σn-6), omega-9 (Σn-9)) of strains of *Rhodomonas*.
Figure 16A:
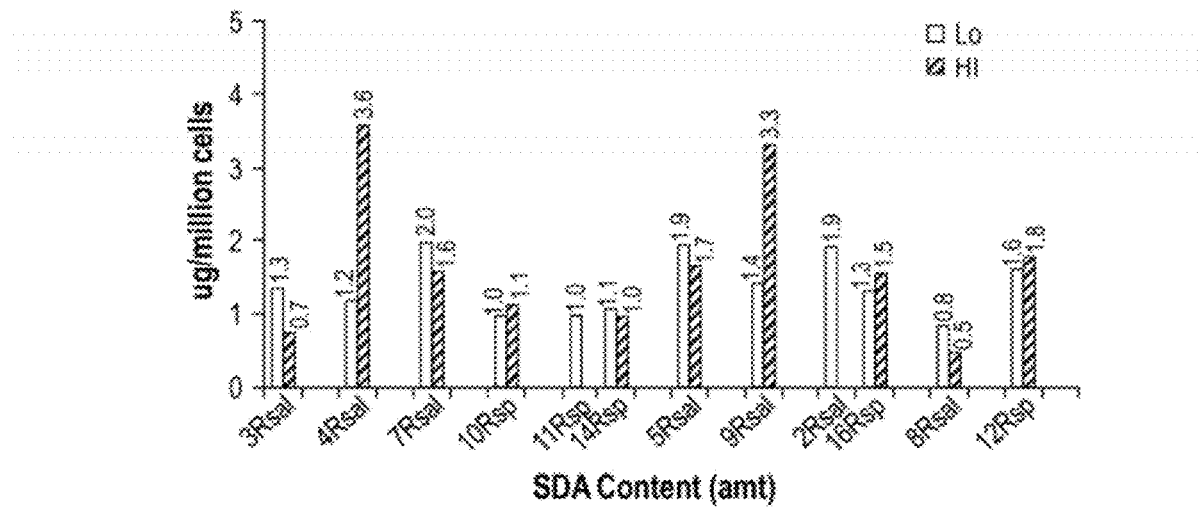
FIG. 16 shows SDA content of *Rhodomonas* strains at low (□) and high (■) density.
Figure 16B:
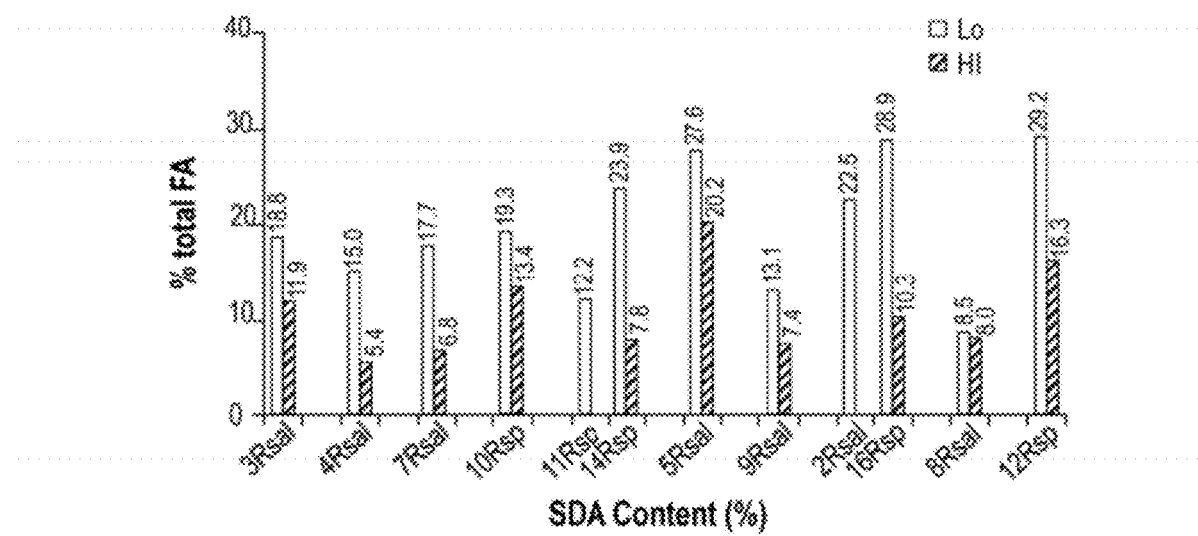
Figure 17:
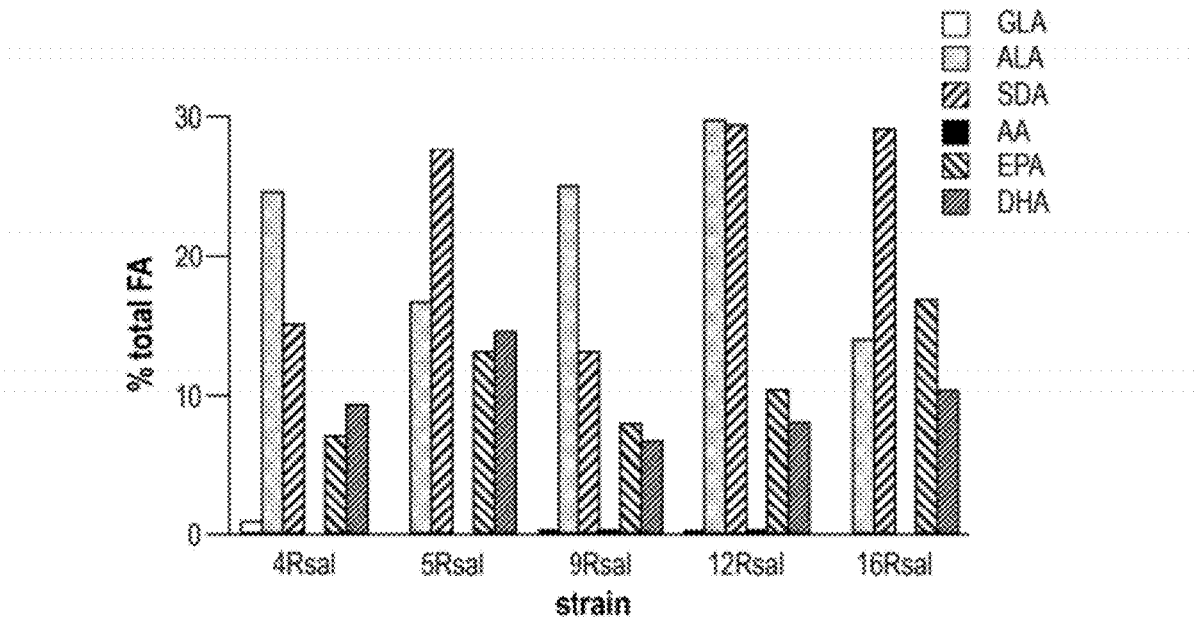
FIG. 17 shows unsaturated FA content of selected *Rhodomonas* strains. γ-linolenic acid (GLA) and arachidonic acid (AA) are omega-6 (n-6; a/k/a Σn-6 or ω-6) FAs; α-linolenic acid (ALA), stearidonic acid (SDA), eicosapentaenoic acid (EPA) and docosahexaenoic acid (DHA) are omega-3 (n-3; a/k/a Σn-3 or ω-3) FAs.

A summary of the distribution of the PUFAs of the strains shown in Table 5 (at the low density harvest) is shown in FIG. 15. The results show that the PUFA content of these strains constitutes about 75-80% of the total FAs with the balance being unsaturated or monosaturated species. Moreover, as shown in FIG. 16, the SDA content of cells varied with the density of cell harvest. In terms of µg amount (per million cells), the stationary phase cells tended to contain more SDA. However, that SDA was a smaller percentage of the total FA content at the latter stage of the growth curve. The PUFA content of strains 4Rsal, 5Rsal, 9Sal, 12Rsp, and 16Rsal is shown in FIG. 17.

Example 10

Cell Density and Nutrient Levels Effect FA Profiles

To determine the effects of cell density and/or nutrient levels on FA content, the growth curve, FA profile, and nutrient utilization of various microalgae strains were examined in parallel.

Each of strains 4Rsal, 5Rsal, 16Rsp, and 12Rsp was grown in its CCMP-recommended medium at two different concentrations of medium phosphate: normal (i.e. ~36 µM; CCMP-recommended); and low (i.e., ~18 µM).

Cells were collected by centrifugation (1000×g, RT, 10 min) and washed once with their appropriate base medium (without phosphate). Washed cells were suspended in 20 ml of their appropriate medium (appropriate base with either normal or low phosphate). These suspensions were added to 380 ml of the same medium in sterile 500 ml glass flasks as shown in Table 7.

TABLE 7

Microalgae cultures.

| Flask | Strain | Base medium (−P) | N:P ratio | Final P (µM) | Final volume |
|---|---|---|---|---|---|
| A | 4Rsal | L1 | 24 | 36.2 | 400 ml |
| B | 4Rsal | L1 | 50 | 17.7 | 400 ml |
| C | 5Rsal | L1 | 24 | 36.2 | 400 ml |
| D | 5Rsal | L1 | 50 | 17.7 | 400 ml |
| E | 16Rsp | Prov50 | 25.8 | 36.2 | 400 ml |
| F | 16Rsp | Prov50 | 52.7 | 17.7 | 400 ml |
| G | 12Rsp | h/2 | 38 | 36.2 | 400 ml |
| H | 12Rsp | h/2 | 78 | 17.7 | 400 ml |

Cultures were grown under static conditions at ~24° C., with a 13/11 hr photoperiod illuminated at about 700 lux. Cell counts were performed at 3-4 day intervals. Periodic samples were collected for medium nutrient levels, cellular FA content and cellular lipid phosphorus content. For these samples, a volume of cell suspension (duplicates when possible) was removed from the flask and cells were collected by centrifugation (1000×g, RT, 10 min). The cell-free supernatant was removed to labeled clean tube and stored at −20° C. for medium nitrate and phosphate measurement. The cell pellet was extracted according to Bligh and Dyer, Can. J. Biochem Physiol., 37:911-7 (1959) and the total lipid extract was stored at −20° C. for FA analysis and lipid phosphorus content. The latter was measured using the assay as described for medium phosphate except that total lipid extract from 5 million cells was dried under a stream of nitrogen gas before the addition of 60 µl water and 150 µl 60% perchloric acid. This mixture was digested at 170-180° C. in a dry heat block until the solution was colorless (2-8 hrs) before the assay was continued as described above.

Figure 18:
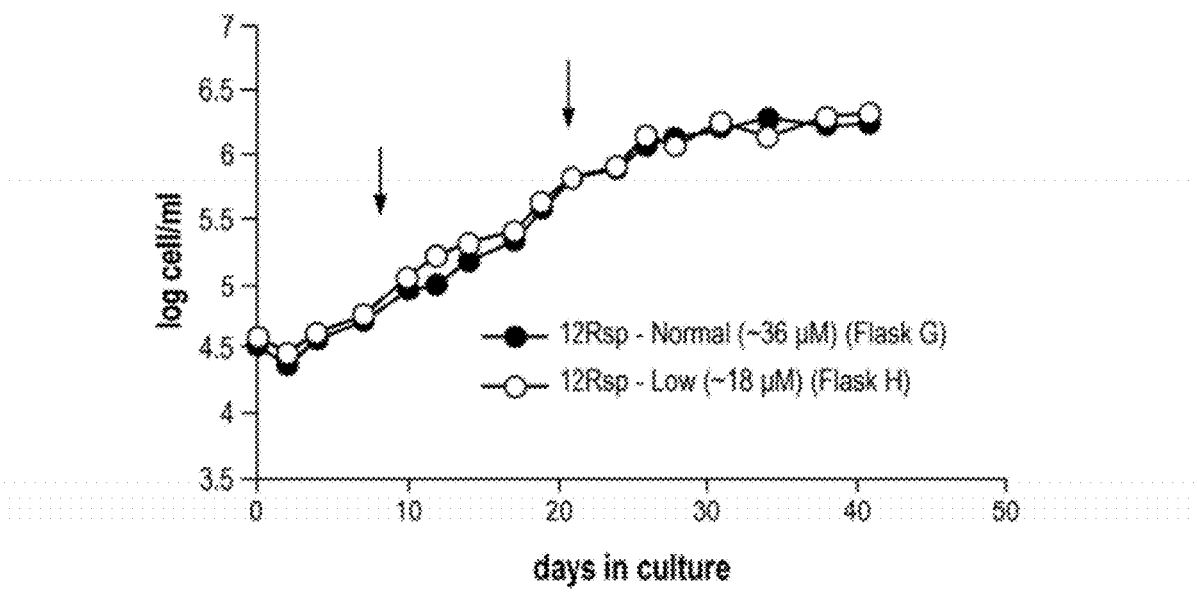
FIG. 18 shows growth characteristic of antibiotic treated strain 12Rsp grown in 500 ml flasks in h/2 medium in the presence of normal (N; ~36 μM) or low (L; ~18 μM) phosphate. The arrows indicate maneuvers to increase light intensity from the initial 700 lux (1×) to ~1000 lux (1×).

FIG. 18 shows the growth curve of strain 12Rsp when grown under normal (N) or low (L) medium phosphate conditions. The exponential or stationary growth phases were not greatly affected by the medium phosphate level for this strain. A similar observation was made for strains 4Rsal, 5Rsal, and 16Rsp.

Figure 19A:
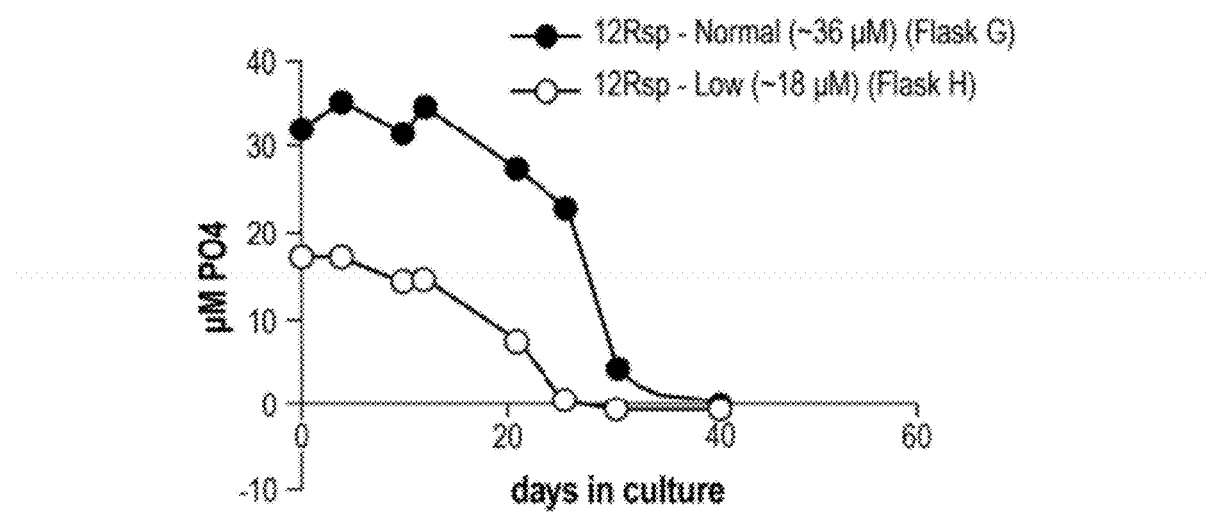
FIG. 19 shows culture medium concentrations of phosphate and nitrate in cultures of antibiotic treated strain 12Rsp grown in the presence of normal (N; ~36 μM) or low (L; 18 μM) phosphate.
Figure 19B:
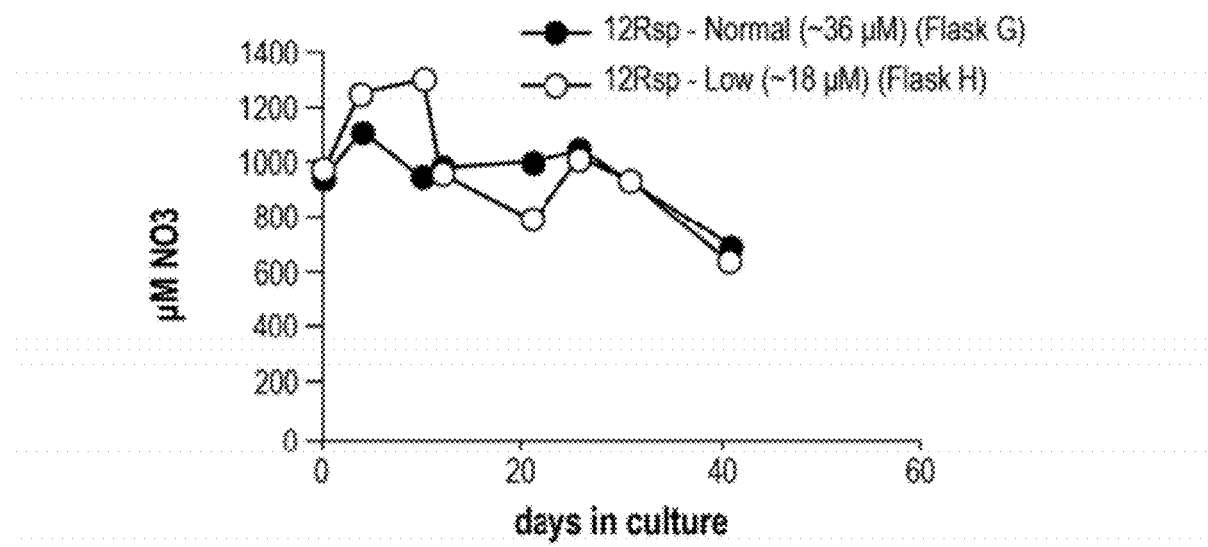
Figure 21A:
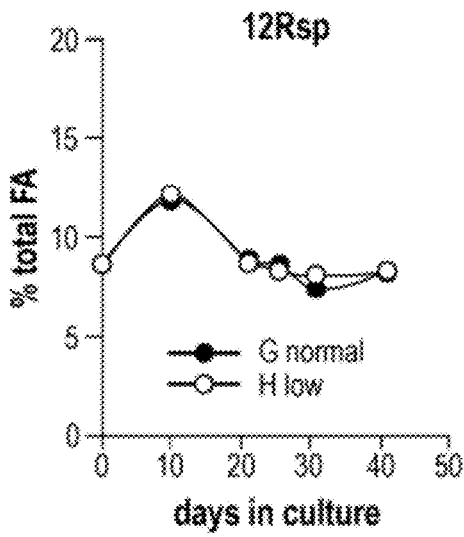
FIG. 21 shows EPA content of *Rhodomonas* strains as function of time in culture grown in the presence of normal (N; ~36 μM) or low (L; ~18 μM) phosphate.
Figure 21B:
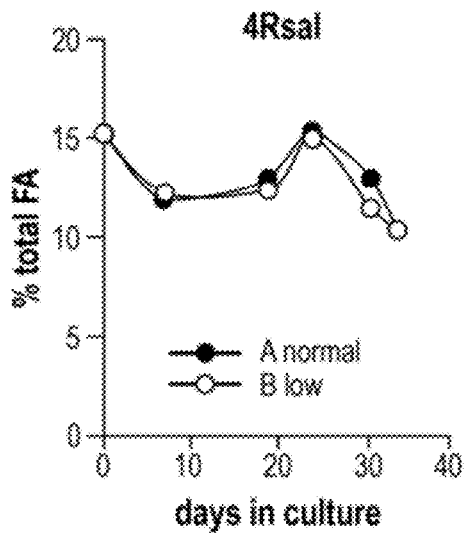
Figure 21C:
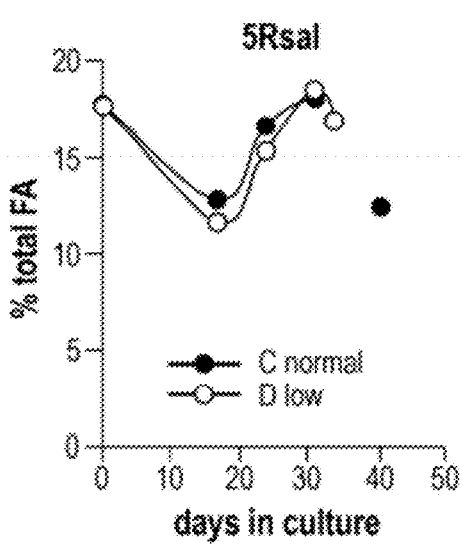
Figure 21D:
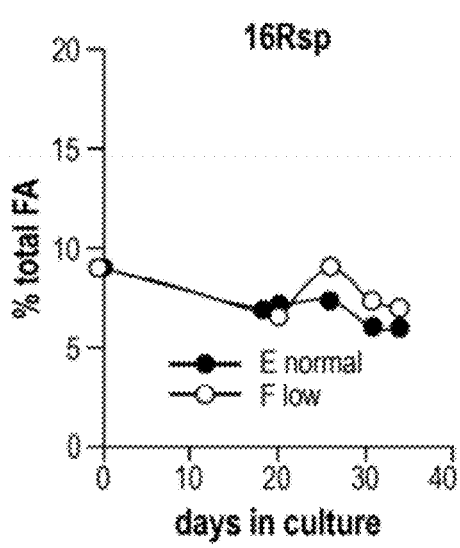

The medium concentrations of the major algal nutrients (nitrate and phosphate) were monitored during the course of algae growth. FIG. 19 shows the nutrient levels in the medium in which 12Rsp was grown. The initial phosphate concentration (FIG. 19, A) in the low condition was about 18 µM and decreased at nearly a constant rate until it was consumed by about day 30. The phosphate utilization in the normal phosphate condition (~35 mM) was slow for the first fifteen days then decreased at nearly a constant rate until it was consumed by about day 40. Nitrate utilization was similar at both phosphate conditions (FIG. 19, B) and was not completely consumed. The h/2 medium in which the 12Rsp cells are cultivated has a second source of nitrogen in the form of ammonium, which was not measured in this experiment and which likely accounts for the relatively slow consumption of nitrate.

The FA content was assessed at several time points across the growth curve for each strain in each medium phosphate condition. As shown in FIG. 20, the SDA content of cells varies somewhat with time in culture for all strains. The maximum content of SDA in the strains was about 30%, 25%, 35%, and 40% total FAs for strains 12Rsp, 4Rsal, 5Rsal, and 6Rsp, respectively. The SDA content tended to peak in each strain and then decrease beyond 20-25 days, at which time most cultures were entering late exponential phase or stationary phase. The content of a long chain FA, DHA, showed some changes during the growth curve but generally remained lower (7-20% of total FA) than SDA (see FIG. 21).

Figures 22A, 22B:
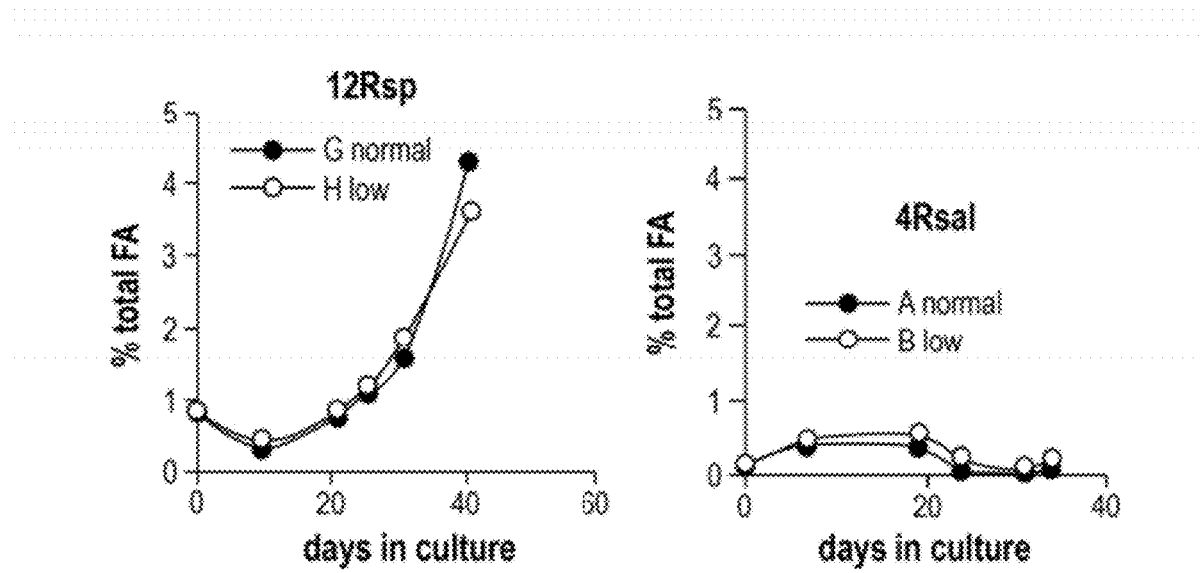
FIG. 22 shows GLA content of *Rhodomonas* strains as function of time in culture grown in the presence of normal (N; ~36 μM) or low (L; ~18 μM) phosphate.
Figures 22C, 22D:
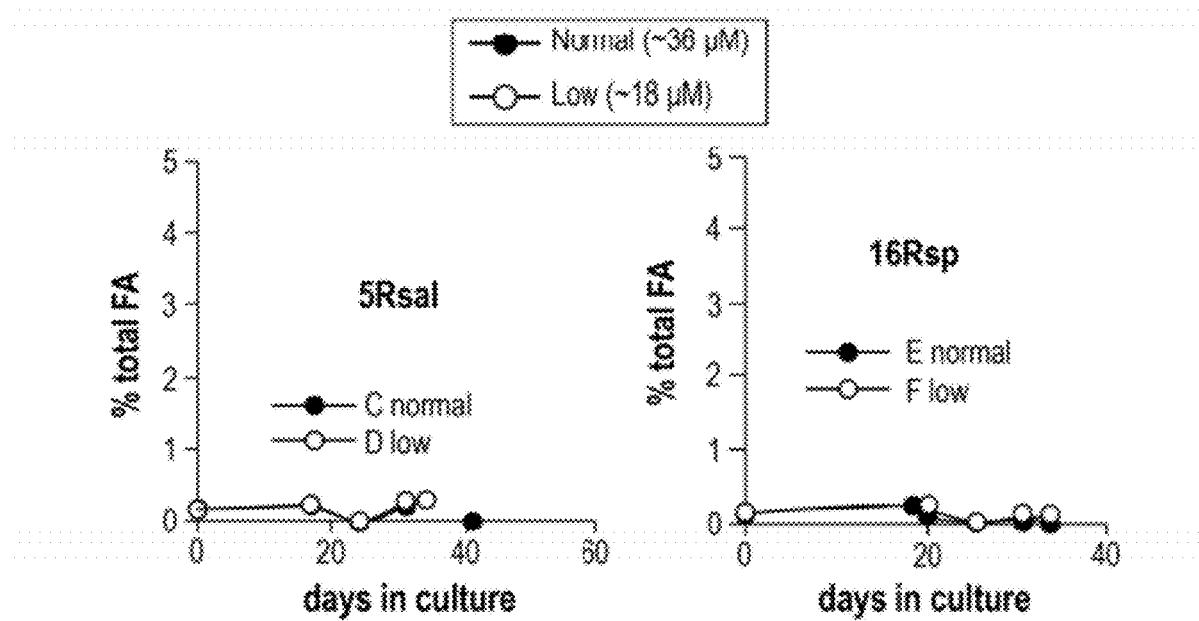

Moreover, as shown in FIG. 22, strain 12Rsp had a GLA content of about 5% of total FA. The initial medium phosphate level did not appear to have any effect on the GLA content of cells per say.

Further, FIG. 23 shows that the level of SDA in 12Rsp peaks as medium phosphate begins to decline as cells enter mid log phase, a period of rapid growth. SDA content then declines as more phosphate is consumed. In contrast, GLA content is low in log phase but begins to increase as cells increasingly consume more medium phosphate and enter late log-stationary phase. DHA levels appear to be relatively immune from the changes in the nutrient levels in the medium. The normal growth of 12Rsp in medium that is not further supplemented with nutrients (depleted by consumption) during the latter stages of the growth curve appears to drive a shift from synthesis of SDA to that of GLA. The results for strains 4Rsal, 5Rsal, and 16Rsp are shown in FIGS. 24, 25, and 26, respectively. Moreover, summaries of FA analysis as a function of growth curves for strains 12Rsp, 4Rsal, 5Rsal, and 16Rsp are shown in FIGS. 27, 28, 29, and 30, respectively.

Figures 31A, 31B:
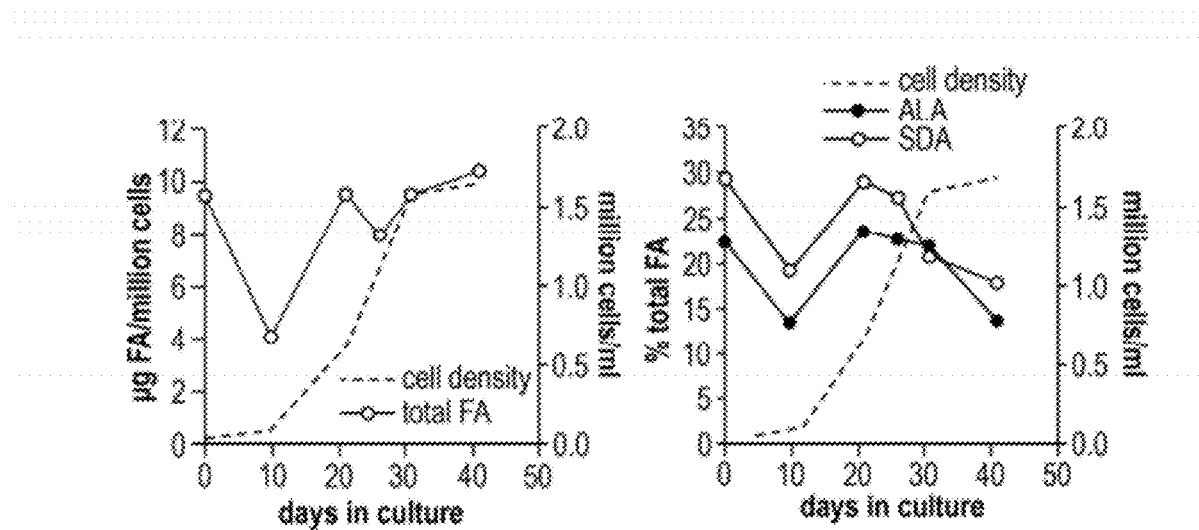
FIG. 31 shows the FA profile of strain 12Rsp through its growth curve. The cell density (dashed curve) is shown in each panel. FAs were assessed during cultivation of cells in flasks: (A) Total; (B) SDA and ALA; (C) GLA and LA; and (D) EPA and DHA. Measurements are the average of duplicate samples.
Figures 31C, 31D:
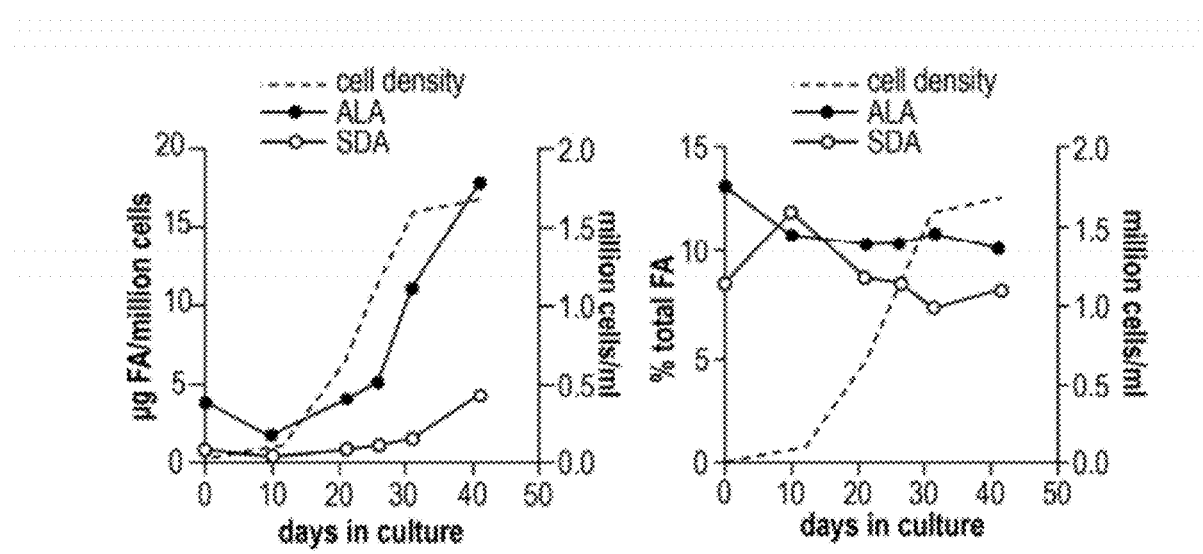
Figure 32A:
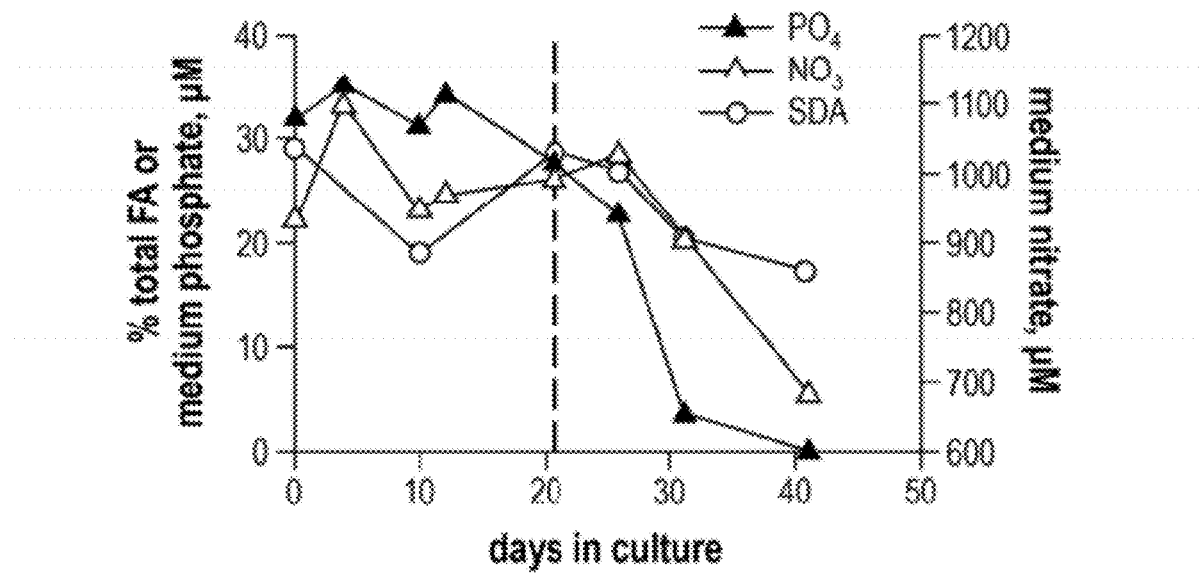
FIG. 32 shows SDA content with nutrient (phosphate and nitrate) status of culture medium and cells in cultures of strain (A) 12Rsp and (B) 5Rsal.
Figure 32B:
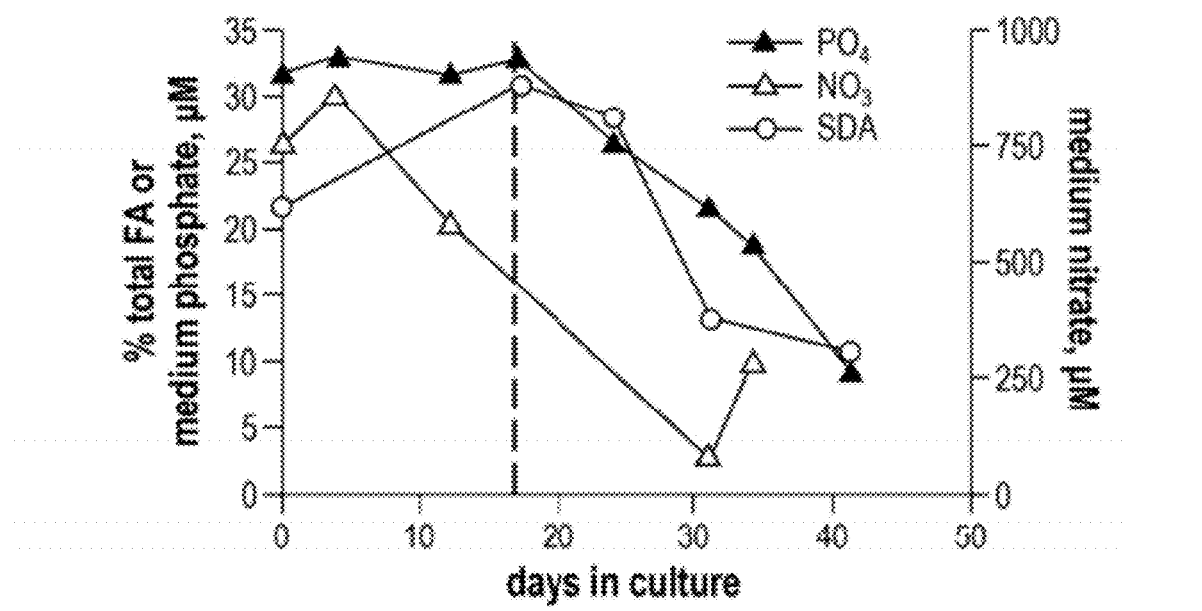

In strain 12Rsp, the total fatty acid content of the cell increased slightly with increasing cell density (FIG. 31). α-linolenic acid [ALA, C18:3(n-3)], SDA, EPA, and DHA all showed a small decrease as a percent of total FAs as the culture transitioned stationary growth phase (FIG. 31). Surprisingly, there was an unexpected concomitant increase in omega-6 18 carbon FAs, LA and GLA in 12Rsp as the cell density increased (FIG. 31C). In contrast, this shift was not seen in any of the other strains (4Rsal, 5Rsal, 9Rsal, 16Rsp) that were examined (data not shown). These results suggest that Δ15 desaturase step (which converts n-6 fatty acids to n-3 fatty acids) can be inhibited to some degree in strain 12Rsp as the cells are stressed in stationary phase. Indeed, the SDA content of 12Rsp peaked (29% total FA; FIG. 32A, dotted line) when medium phosphate was reduced by only 30% and medium nitrate concentration was unchanged. In contrast, the peak SDA content (31% of total FA; FIG. 32B, dotted line) of strain 5Rsal occurred when medium nitrate was reduced by 70% and medium phosphate concentration was unchanged. Thus, PUFA synthesis in members of the same genus appears to be differentially regulated. Moreover, these findings suggest that the FA content of *Rhodomonas* can be manipulated to achieve a desired FA composition. Further, initial experiments suggest that about 25-35% of algal biomass (by dry weight) is composed of FA-based lipids.

The surprising concomitant increase in omega-6 18 carbon FAs, LA and GLA in 12Rsp as the cell density increased provides a critical tool to produce algae that not only contain SDA and ALA, but also GLA. Seed oils that contain SDA/GLA combinations have been shown to be the most efficacious for blocking human biomarkers of chronic diseases in patient populations.

Example 11

Effect of Carbon Source on FA Profile

Figure 33:
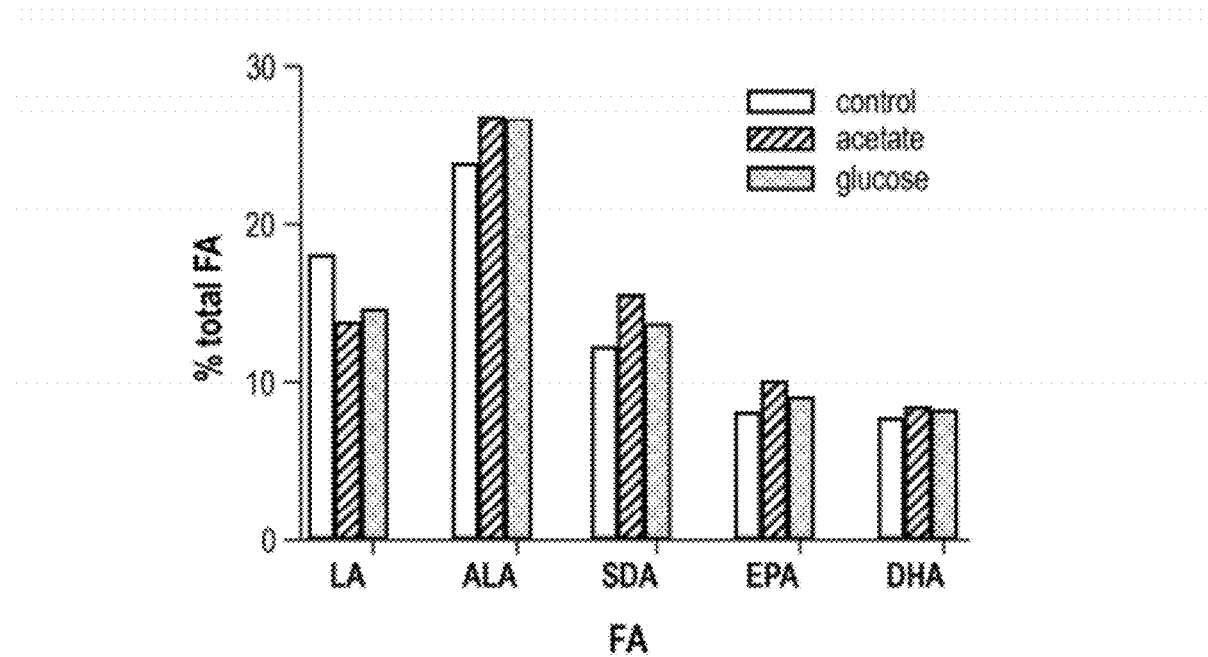
FIG. 33 shows FA profile of strain 12Rsp grown in the absence (control) or the presence of 55 mM glucose or 2 mM acetate for 9 days. Duplicate samples were harvested for FA analysis.

To determine an alternative method of manipulating algal FA content, growth and FA content of strain Rsp12 was determined in the presence of a single dose of glucose (55 mM) or acetate (2 mM). As shown in FIG. 33, a small decrease in the omega-6 series precursor linoleic acid (LA) and small increases in several omega-3 FAs (ALA, SDA, EPA, DHA) were observed. These findings suggest that the selected strains of Rhodomonas are able to utilize organic carbon sources and that their supplementation can alter the FA profile. The growth of the most light-sensitive strain (16Rsp) was examined in the presence of glycerol (0.1M and 0.4M). These doses were previously used in studies with a diatom and a green algae. The results showed that strain 16Rsp failed to thrive but did not die (data not shown). The exposure to glycerol did however induce a loss of chlorophyll from cells.

Example 12

Growth and FA Profiles of Reactor-Cultivated Rhodomonas

Figure 34:
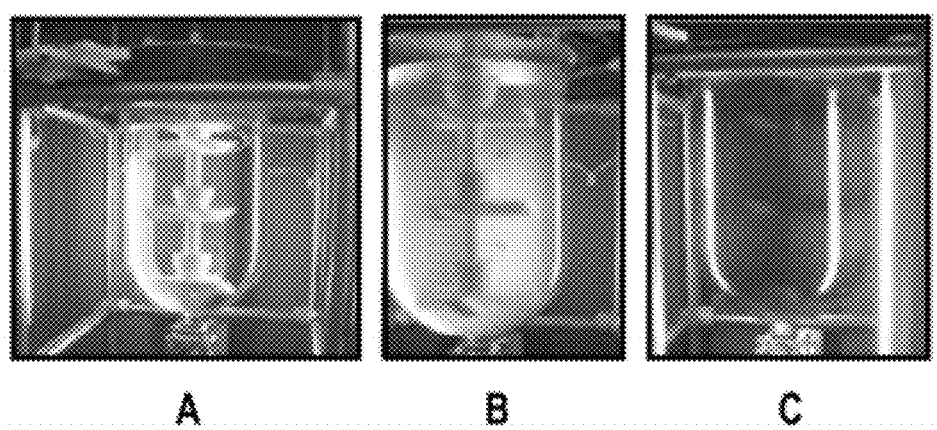
FIG. 34 shows a 30 L glass photobioreactor (PBR) (34 cm diam×50 cm; Chem-Flowtronics, NJ) resting in an aluminum frame. A top-mounted air motor (not visible) powers the Teflon paddles. Lights are located outside the frame. (A) Un-inoculated PBR; (B) Freshly inoculated PBR (~4.5×10$^4$ cell/ml); and (C) PBR at near maximal cell density (~0.8×10$^6$ cell/ml).

To determine whether Rhodomonas strains can thrive under reactor conditions, strain 12Rsp was grown in a 30 L glass reactor (FIG. 34).

The glass walled 30 L reactor (ChemFlowtronics) was cleaned with 10% bleach (overnight) and rinsed at least six times with tap water and then at least 3 times with deionized water (FIG. 34A). The reactor was allowed to air dry. The Teflon lid was similarly washed, rinsed with 70% isopropanol and wrapped in autoclave paper until assembly. The reactor was rinsed thoroughly with 70% isopropanol, the lid was installed while the reactor was wet and the assembled reactor was air dried. Before addition of medium, the dried reactor was rinsed with filtered seawater. About 28 L of filtered seawater was added to the reactor through a lid port using an autoclave funnel. Appropriate volumes of 1000× nutrients for a CCMP medium kit (f/2) for a 30 L final volume were added to the reactor. Ammonium chloride was added to the medium to make the required h/2 medium for 12Rsp. The paddle (three-tier Teflon) stir mechanism was started at ~60-100 rpm, powered by a filtered air motor on a house air line.

The reactor was inoculated with ~2 L of 12Rsp, yielding an initial cell density of ~4.5×10$^4$ cell/ml (FIG. 34B). The culture was stirred continuously and illuminated (13/11 hr light/dark cycle) with three 14 W fluorescent lamps. Cell density, pH (dipstick, then by pH meter), nutrient (phosphate, nitrate) levels and CO2 content (phenolphthalein titration with NaOH; not quantitative yet, only relative values at the moment) were monitored at regular intervals. The medium was supplemented with nutrients as they were consumed in order to obtain a maximal cell density.

As the culture reached maximum density (~0.8 million cells/ml; FIG. 34C), increased adherence of cells to reactor surfaces was observed, particularly near surfaces receiving incident light. Nevertheless, despite nutrient fluctuations, the potential stress induced by continuous stirring and self-shadowing at high density, strain 12Rsp thrived in the reactor. Thus, it is feasible that scaled up cultivation of can be achieved.

Moreover, the maximal cell density achieved in this photobioreactor (PBR) underestimates the total biomass due to the cell adherence to the reactor surfaces. The reactor culture was harvested on day 41 at a cell density of 5.4×10$^5$ cells/ml. This is lower than the peak cell density of 7.6×10$^5$ cells/ml on day 19. It is likely that the culture was in stationary phase even though cell density had decreased. Increased adherence to the vessel walls and paddles was observed during the last the part of the time in culture. It is very likely that the cells were experiencing nutrient stressors despite the addition of nutrients.

The FA content of the cells at harvest was assessed as was an estimate of the dry weight of the cells. Total lipid extracts were prepared from duplicate samples of about 10 million cells and analyzed as described above. The dry weight was estimated by filtering 10 million cells onto a pre-dried, pre-weighed glass fiber filter (4.25 cm) and washing 3 times with 3.4% ammonium bicarbonate. The washed filter was dried over night (100° C.), reweighed and the dry weight was calculated by difference. The harvested cells were 98.9 mg/million cells. The total number of cells recovered from the reactor was 1.6×10$^{10}$ cells (based on density of cells in suspension; likely an underestimate because due to adherent cells, which were also harvested). Therefore the total dry weight of the reactor harvest is expected to be 1.58 g of algal biomass dry weight.

Approximately 30 L of suspension was filtered through two 1 micron pore pre-weighed polyester felt filter socks (McMaster-Carr, Atlanta), approximately half of the volume through each sock. Despite the pore size (smaller than the organism) the filtrate was visibly rust-colored, indicating the presence of 12Rsp algae in the filtrate. This was confirmed by microscopic inspection of the filtrate. Therefore the filtrate was centrifuged (1000×g, RT, 20 min) to recover the cells. The supernatant was decanted and the residual cells pooled and added back to the filter sock. All cell-free medium was autoclaved prior to disposal. The filter socks were placed on multiple changes of paper towel to wick out as much liquid as possible. The sock opening was covered with a double layer of clear plastic wrap and secured by a rubber band. Each sock was placed in a small individual plastic bag and labeled. Both bags were placed in a larger bag and stored at −20° C. until further processing.

Figure 35A:
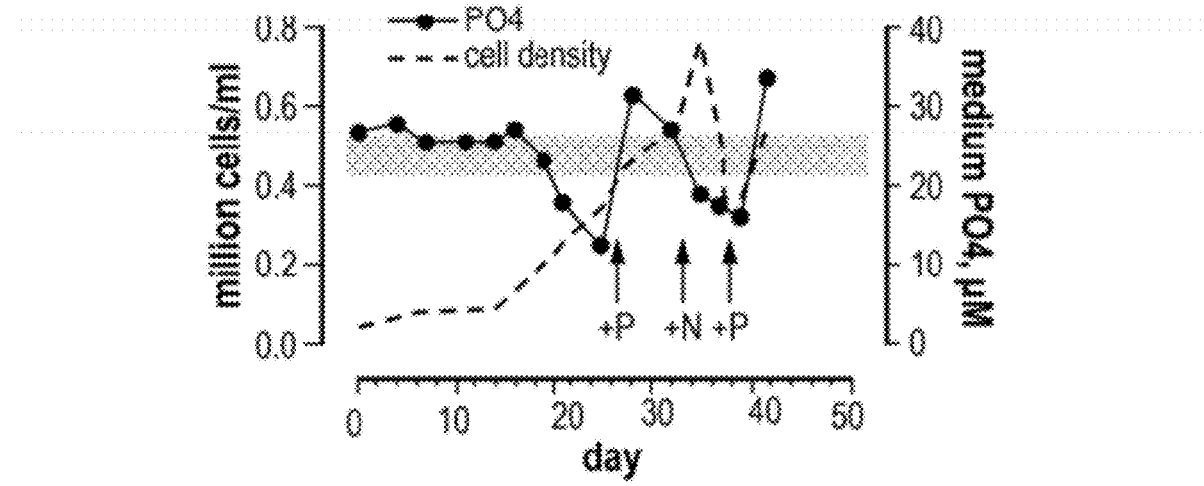
FIG. 35 shows growth characteristic of strain 12Rsp in culture. Reactor levels of phosphate (A) and nitrate (B) were monitored and added as indicated by the arrows (P, solid; N, dashed). The target nutrient range (optimal less 20%) is indicated by the shaded boxed range.
Figure 35B:
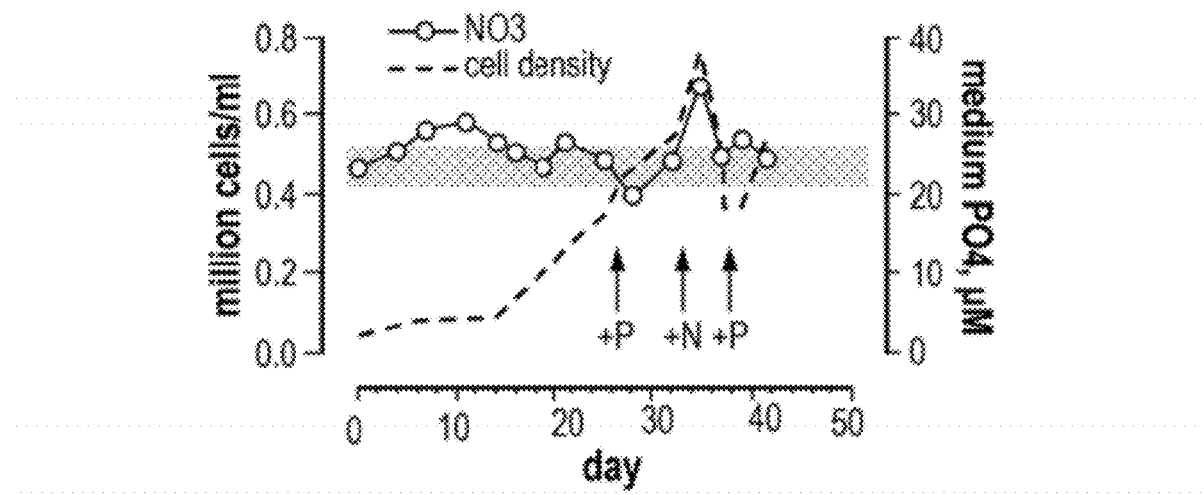
Figure 36B:
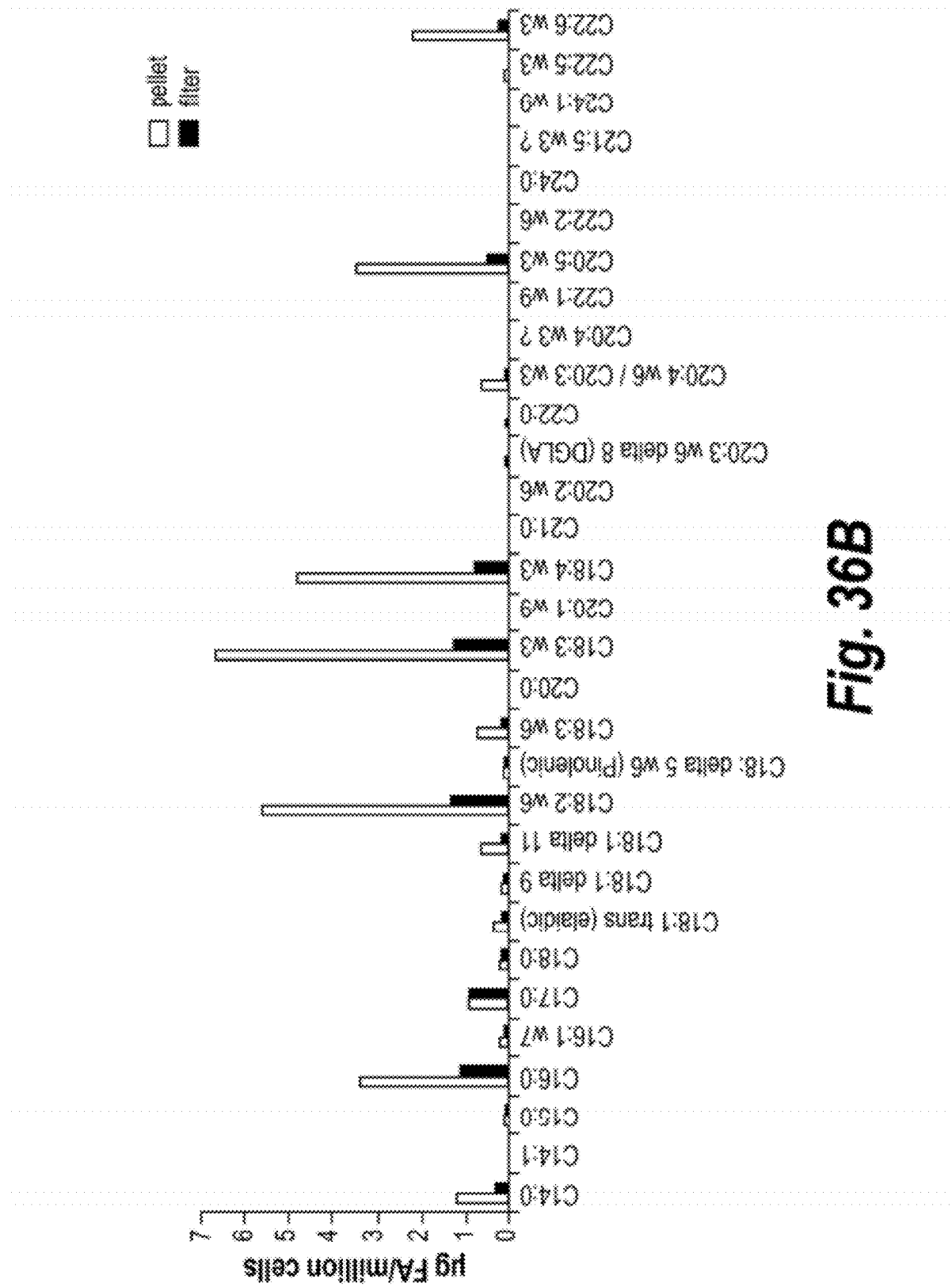
FIG. 36 shows FA profile of strain 12Rsp grown in a PBR: (A) shows the FA profile (as % total FA) of strain 12Rsp when lipids were extracted from intact cells by the method of Bligh and dyer (B) shows a comparison the FA profile of strain 12Rsp when lipids were extracted by two methods (pellet=10 million intact cells extracted immediately by the method of Bligh and Dyer; and filter=10 million cells captured on a glass fiber filter and dried overnight before extracted by the method of Bligh and Dyer); (C) shows the same data as that in B expressed as % of total FAs; and (D) shows the recovery of total FAs from the two extraction methods used.
Figure 36C:
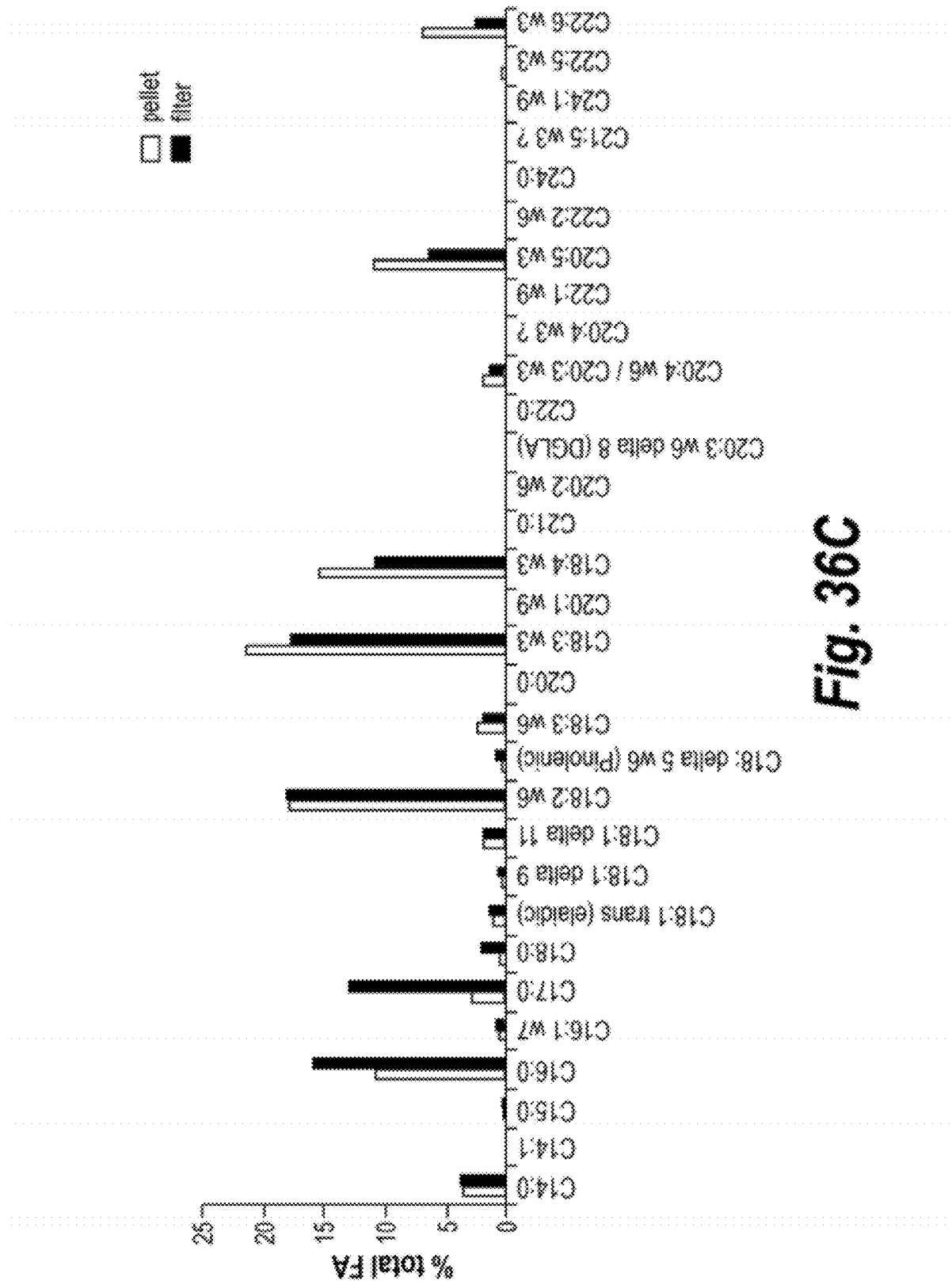
Figure 36D:
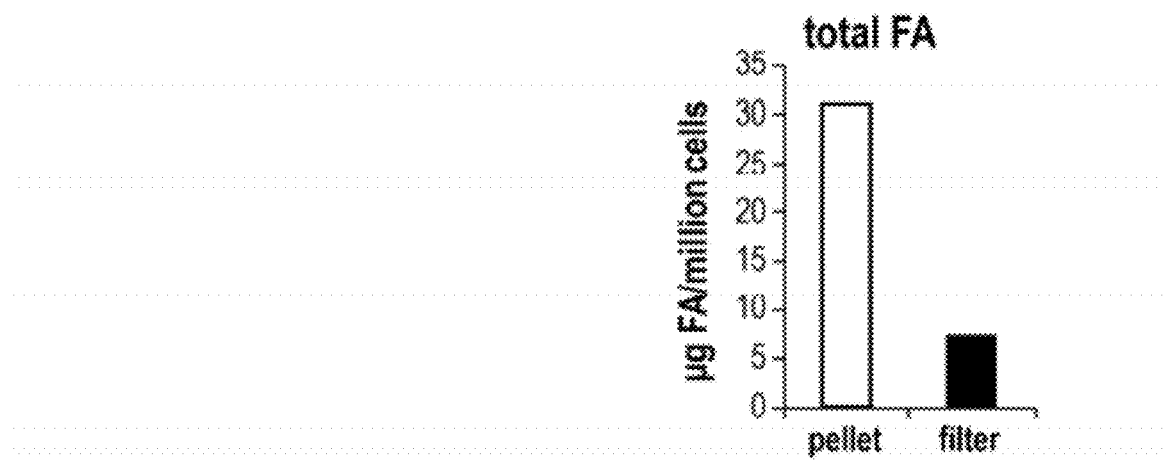

As shown in FIG. 35, the growth rate of 12Rsp was responsive to nutrient additions. Phosphate (FIG. 35A) was consumed at about twice the rate of nitrate (FIG. 35B). However, the addition of nitrate (+N, dashed arrow; day 32) appeared to restore the growth rate more robustly than did the additions of phosphate (+P, solid arrows; days 25 & 39). We hypothesize that maintenance of the medium phosphate and nitrate concentrations within 20% of their optimal levels (red boxed range) will minimize the impact of nutrient limitations on growth rate. The results suggest that maintenance of the medium phosphate and nitrate concentrations within about 20% of their optimal levels (FIG. 35, shaded range) can minimize the impact of nutrient limitations on growth rate. The elevated GLA (C18:3n-6; ~2.4%) content of these cells suggests that they were beginning to experience nutritional stress (FIG. 36A; FIG. 36C).

Example 13

Growth of Microalgae in Various Culture Vessels

Figure 37A:
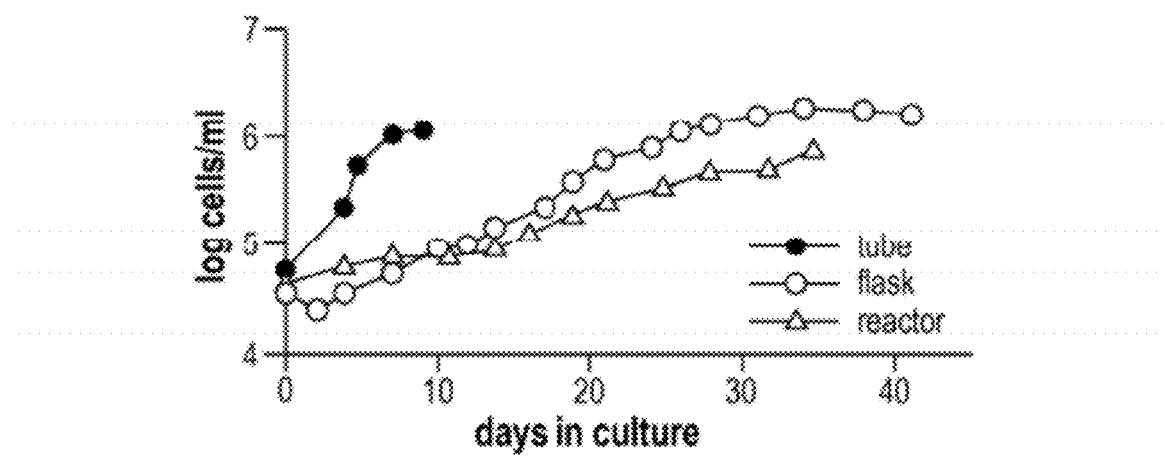
FIG. 37 shows growth characteristic of strain 12Rsp grown under similar nutrient and incident light conditions in tube (●), flask (○), and reactor (▲). Cell density expressed as either (A) log cell/ml or (B) million cells/ml.
Figure 37B:
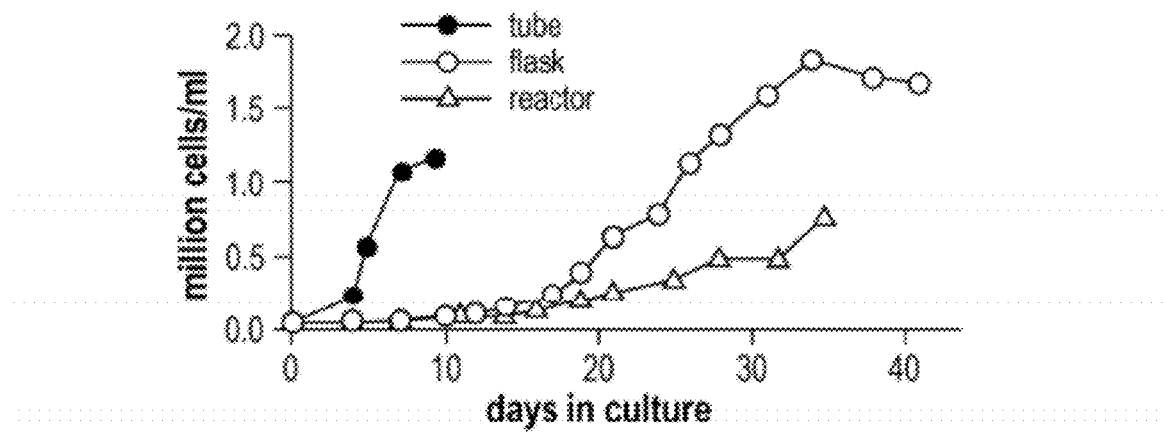
Figure 38:
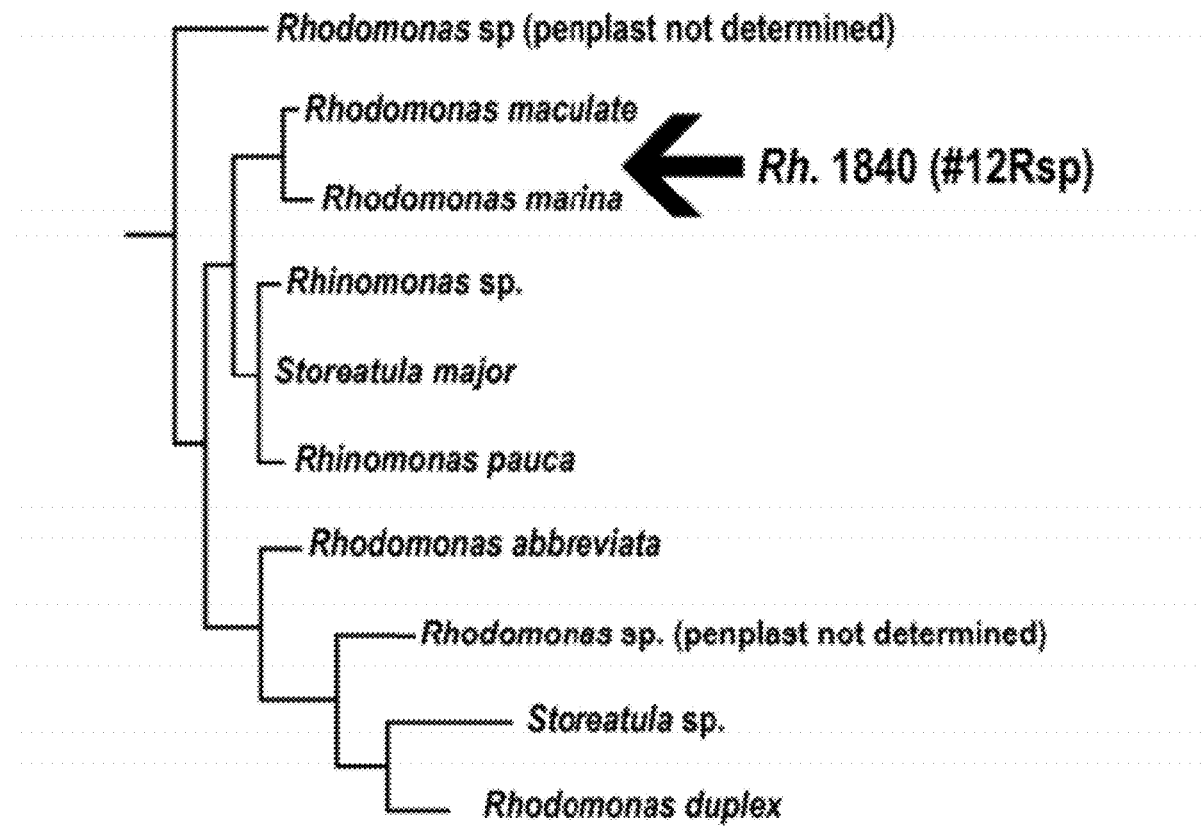
FIG. 38 shows assignment of strain 12Rsp with a Rhodomonal cluster within the cryptomonad phylogenic tree.

FIG. 26 shows a comparison of strain Rsp12 growth curves in various culture vessels tested to date. The growth rate decreased (FIG. 37A) as the size of the vessel increased resulting in increased doubling times (DT; see also Table 8).

TABLE 8

Doubling times

| Name | Tube | Flask | Reactor |
|---|---|---|---|
| 4Rsal | 2.5 | 7.7 | nd |
| 12Rsp | 1.9 | 4.3 | 7.3 |
| 5Rsal | 2.5 | 4.3 | nd |
| 9Rsal | 2.3 | nd | nd |
| 16Rsp | 2.5 | 4.3 | nd |
| Vessel diameter (cm) | 2 | 9 | 34 |
| Square root of vessel diameter | 1.41 | 3 | 5.83 |
| Diameter-adjusted doubling time (days) | 1.3 | 1.4 | 1.3 |

Also, the initial lag time increased (FIG. 26B) with vessel size (tube, 2 days; flask, 18 days; reactor, 20 days). When the diameter of the vessels is taken into account (DT/√diameter), the adjusted doubling time (Table 8; Diameter-adjusted doubling time) for the microalgae in the three vessels is comparable.

The increased light path of the larger vessels appears likely to be responsible for the apparent slow growth. It is noteworthy that the doubling times of the other selected strains (Table 8) appear to follow the same trend as that observed for 12Rsp. Thus, it appears that growth rates for all stains can be defined by vessel size and geometry and to a lesser extent by intrinsic properties of the algal strains.

Example 14

Phylogenetic Determination of Microalgae Strain 12Rsp

To further determine strain 12Rsp (ATCC No. PTA-9989), its nucleus- and nucleomorph-encoded 18S ribosomal RNA genes were sequenced and analyzed.

Cell culture and nucleic acid extraction: 12Rsp was grown at 22° C. in f/2-Si medium with a 14-10 h diurnal cycle. Dense 100-200 mL cultures were harvested by centrifugation and subjected to nucleic acid extraction. Cell pellets were re-suspended in a Tris-HCl extraction buffer (200 mM Tris-HCl (pH 7.5, 250 mM NaCl, 25 mM EDTA, 0.5% SDS) and incubated for 10 mM at 50° C. Samples were centrifuged (15,000×g) for 5 mM and the aqueous phase was extracted twice using phenol and chloroform. DNA was ethanol precipitated from the aqueous phase and pelleted by centrifugation at maximum speed. Pellets were washed with ethanol, dried, re-suspended in 200 ml of TE buffer and stored at −20° C.

PCR amplification, cloning and sequencing: Small subunit ribosomal RNA (SSU rRNA) genes were PCR amplified on an Eppendorf Mastercycler using Platinum High Fidelity Taq polymerase (Invitrogen) and the following primers: Cr.NM.SSU.F1: 5'-CAG TAG TCA TAT GCT TGT CTT AAG-3' (SEQ ID NO:3); G07: 5'-AGC TTG ATC CTT CTG CAG GTT CAC CTA-3' (SEQ ID NO:4). PCR conditions included an initial 5 min denaturation step at 94° C., 45 cycles of 94° C. for 30 sec, 50° C. for 1 min and 68° C. for 4 min, and a final 5 min extension at 68° C. PCR products were subjected to electrophoresis on 0.8% agarose crystal violet gels. Amplicons of the expected size (~1.8 kilobase pairs) were excised and purified using the MinElute Gel Extraction Kit (Catalog number 28604, Qiagen, Valencia, Calif.). Purified products were cloned using the TOPO XL Cloning Kit (Invitrogen, Carlsbad, Calif.). Sixteen clones were PCR screened for the presence of inserts using M13 forward and reverse primers (94° C., 3 min, 45 cycles of 94° C. for 30 sec, 45° C. for 30 sec, 72° C. 3 min) Eight insert-containing clones were sequenced using the CEQ Dye Terminator Cycle Sequencing kit (Beckman Coulter, Inc., Fullerton, Calif.) and run on a Beckman CEQ8000 capillary DNA sequencer. Inserts were completely sequenced on both strands using a combination of universal (M13) primers and internal gene-specific primers.

18S rRNA gene sequence analysis and strain determination: The SSU rRNA gene sequences determined above were compared to those present in the GenBank public database using the BLASTn algorithm and the BLAST tree widget with the Neighbor Joining setting (http://www.ncbi.nlm.nih.gov/blast/). These analyses revealed that two distinct gene fragments were amplified from 12Rsp, corresponding to both nucleus- and nucleomorph-encoded loci—these gene fragments were 1705 (SEQ ID NO:1) and 1822 (SEQ ID NO:2) nucleotides in size, respectively. The nucleomorph gene fragment was found to share 99% identity (1808 of 1822 residues) with the nucleomorph SSU rDNA gene of *Rhodomonas mariana* (GenBank Accession #X81374). The nuclear gene fragment was identical to the SSU rRNA genes of *Rhodomonas maculata* (Accession #AF508274) and *Rhodomonas salina* (Accession #EU926158), with the exception of two ambiguous positions in the CCMP757 consensus sequence.

Based on BLAST and phylogenetic analyses, it is clear that strain 12Rsp is very close but not identical to a cluster of *Rhodomonas* strains including *Rhodomonas baltica* RCC350, *R. salina* CCMP1319, and *Rhodomonas mariana*. As shown in FIG. 39, the tentative location of strain 12Rsp in a section of the phylogenetic tree that contains the extended cryptomonad family.

Example 15

Lipid Composition Extracted from Microalgae

Two (2) filter socks containing ~1.58 grams (dry weight) of microalgae biomass were each washed five (5) separate times using 100 ml of 3A virgin ethanol per wash so as to remove algae and residual oils from them.

This resulted in approximately 1,000 ml of total solution which was then heated under nitrogen blanket to 50° C. using a hot plate stirrer coupled with thermo probe. Solution was agitated gently via stirrer bar in this condition for 30 minutes. Solution was then evaporated to 250 ml (via Rotovapor R110 fitted to a Brinkman 169 Vacuum Aspirator) so as to remove the majority of the alcohol. Bath temperature varied from 46-48° C. with full allowable vacuum. During transfers between each vessel, a small quantity (less than 20 ml) of ethanol was used to wash the former vessel free of materials. The resulting solution was dark green and comprised mainly of alcohol and dissolved chlorophyll and oils. There was a small quantity of white precipitate, determined to be most-likely residual salts and some sterols from the algae.

The 250 ml (approximate) solution was then transferred to a 500 ml beaker into which 0.5% each (by weight) of the following was added: bleaching clay, activated carbon, and filter aid. This mixture was returned to the hotplate and agitated under nitrogen at 60° C. for 30 minutes, then filtered through ashless paper using vacuum assistance. The resultant product (now noticeably lighter in colour) was returned to a 250 ml beaker and reduced further via 60° C. hotplate/stirrer and assisted by nitrogen aspiration. When the volume reached 30 ml, the materials were transferred yet again to a 100 ml beaker with an equal amount of acid water (pH 1.5 via equal proportions of sulfuric and phosphoric acids). This was heated/stirred at 60° C. under nitrogen blanket for 50 minutes, resulting in a reduction to approximately 40 ml total volume. This solution appeared to be mainly colored water with a dark precipitate and a dark green oil slick. The water with chlorophyll precipitate was removed. The oil slick was placed in a 25 ml beaker and the 250 ml vessel rinsed with 10 ml ethanol to ensure total transfer. Alcohol was evaporated at 60° C. via hotplate/stirrer (plate digital set point and no thermo probe) with nitrogen aspiration. When the alcohol was nearly gone, material was transferred in phases to a 4 ml vial and placed in heat block set 60° C. and aspirated with nitrogen until the oil was fully dried. Result was approximately 3 ml of oil.

Example 16

Food Comprising a Lipid Composition Prepared from Microalgae

A lipid composition prepared according to Example 15 is added to yogurt to a level of about 1.8 g/serving or 1.0% of prepared yogurt base. The formulas and calculated approximate composition of the yogurt comprising the oil (batch 1) and a control yogurt without the oil (batch 2) are listed in Tables 9 and 10.

TABLE 9

Yogurt ingredients.

|  | Batch 1 (g) | Batch 2 (g) |
|---|---|---|
| Skim Milk | 139.75 | 142.75 |
| Whole Milk | 121.62 | 121.62 |
| Non Fat Dry Milk | 10.13 | 10.13 |
| Sucrose | 7.00 | 7.00 |
| Stabilizer Blend* | 4.50 | 4.50 |
| *Rhodomonas* Oil | 3.00 | — |
| Total Grams | 300.00 | 300.00 |

TABLE 10

Yogurt composition.

|  | Batch 1 (%) | Batch 2 (%) |
|---|---|---|
| Milk Solids not Fat | 11.03 | 11.03 |
| Fat (including *Rhodomonas*) | 2.50 | 1.50 |
| Total Sugar | 14.74 | 14.74 |
| Protein | 4.10 | 4.10 |

300 g batches of yogurt base are made according to a typical lab scale process for the manufacture of set yogurt.

1. Skim milk and part (81.62 g) of the whole milk are blended together.

2. The dry ingredients are blended together and added to the skim/whole milk blend with sufficient agitation to disperse the powders but not to create excessive foaming.

3. *Rhodomonas* oil is added to the remaining 40 g of whole milk and homogenized by passing the mixture through a double hub, 20 gauge homogenizing needle 20 times to insure complete emulsification of the oil. (For the control batch 40 g of whole milk without oil is homogenized in the same manner.)

4. The homogenized oil/whole milk blend is then added to the remaining milk solution from step 2.

5. The total milk blend (yogurt base) is pasteurized at 80° C. for 1 minute.

6. The yogurt base is cooled to 42° C. and inoculated with a blend of *Streptococcus thermophilus* and *Lactobacillus delbrueckii* subsp. *bulgaricus* at rates prescribed by the manufacturer.

7. The yogurt base is incubated at 42° C. for approximately 7 hours until the pH reached 4.6 and the product develops as a soft gel.

8. The yogurt is cooled to 4° C. and held for analysis.

After two days, yogurts were evaluated for syneresis of whey, separation of oils and texture. Texture analysis is measured by determining yield strength using a Brookfield, DY-III Ultra Viscometer with a vane spindle (spindle #74, 0.08 rpm) attachment.

Yogurt with oil has a slightly lower yield which is not unexpected in yogurts containing fat with lower melting points. Yields in the range of 300-500 pa are acceptable and common in sweetened, commercial yogurts made with 10-11% milk solids not fat, especially those with fairly mild heat treatments. While the yogurt with oil shows a slight amount of creaming, the inability to completely homogenize the yogurt after pasteurization (as typically done in standard yogurt manufacture) probably contributes to such a result. In addition, the control yogurt (batch 2) only contains 1.5% fat, a level that one would not expect to result in creaming in set yogurt. Also, the amount of creaming in batch 1 is less than typically seen in many commercial full fat yogurts containing 3.2% fat. The results for measurements of syneresis, oil separation and texture after storage at 4° C. for two days are shown in Table 11.

TABLE 11

Syneresis, oil separation and texture of yogurts.

|  | Batch 1 | Batch 2 |
|---|---|---|
| Syneresis (% w/w) | 1.85 | 1.67 |
| Separation of Oil (visual) | Slight | none |
| Yield (pa) | 312 | 350 |

We claim:

1. An isolated microalgae of the *Rhodomonas* strain ATCC No. PTA-9989.

2. A process of making a polyunsaturated fatty acid (PUFA) composition comprising at least 8% polyunsaturated fatty acids in weight, the process comprising: extracting the polyunsaturated fatty acids from the microalgae of claim 1, wherein,
   (a) SDA is in an amount of about 5% to about 50% of total fatty acids;
   (b) EPA is in an amount of about 2% to about 40% of total fatty acids;
   (c) DHA is in an amount of about 2% to about 40% of total fatty acids; and optionally
   (d) GLA is in an amount of about 0.1% to about 10% of total fatty acids; wherein the composition comprises at least 8% polyunsaturated fatty acids in weight.

3. The process of claim 2, wherein the microalgae is a microalgae having a cell wall of reduced thickness as compared to the wild-type microalgae, wherein said cell wall of reduced thickness improves extractability and/or bioavailability of the microalgae lipid fraction.

4. A process of making a composition comprising at least 5% stearidonic acid, the process comprising:
   (a) cultivating the microalgae of claim 1 to produce a microalgae biomass; and either
   (b) extracting said microalgae oil from said cultivated microalgae; or
   (c) removing water from said microalgae biomass to achieve a solids content from 5 to 100% weight percent; wherein the composition comprises at least 5% stearidonic acid.

5. A method for preparing a microalgae biomass composition comprising one or more PUFAs, the method comprising: culturing a microalgae of claim 1 under a culture condition sufficient to provide a microalgae biomass comprising the one or more PUFAs, wherein the microalgae biomass is harvested after at least one logarithmic growth phase of the microalgae, wherein the omega-3 fatty acid is stearidonic acid (SDA), wherein the omega-6 fatty acid is γ-linolenic acid (GLA), wherein the SDA at harvest is at least about 5% of the total fatty acid, wherein the GLA at harvest is less than about 1% of total fatty acid.

6. The method of claim 5, wherein the culture medium comprises a first phosphorus concentration at a lag phase and a second phosphorus concentration at the logarithmic growth phase at harvest, wherein the second phosphorus concentration is at or within about 20% of the first phosphorus concentration.

7. A biologically pure culture of the isolated *Rhodomonas* of claim 1.

8. A method for preparing a microalgae biomass composition comprising one or more PUFAs, the method comprising: culturing a microalgae of claim 7 under a culture condition sufficient to provide a microalgae biomass comprising the one or more PUFAs, wherein the microalgae biomass is harvested after at least one logarithmic growth phase of the microalgae, wherein the omega-3 fatty acid is stearidonic acid (SDA), wherein the omega-6 fatty acid is optionally present and is γ-linolenic acid (GLA), wherein the SDA at harvest is at least about 5% of the total fatty acid, wherein the GLA if present at harvest is less than about 1% of total fatty acid.

9. A method for preparing a microalgae biomass composition comprising at least 8% polyunsaturated fatty acids in weight, the method comprising: culturing a microalgae of claim 7 the process comprising: extracting the polyunsaturated fatty acids from the microalgae, wherein,
   (a) SDA is in an amount of about 5% to about 50% of total fatty acids;
   (b) EPA is in an amount of about 2% to about 40% of total fatty acids;
   (c) DHA is in an amount of about 2% to about 40% of total fatty acids; and optionally
   (d) GLA is in an amount of about 0.1% to about 10% of total fatty acids; wherein the composition comprises at least 8% polyunsaturated fatty acids in weight.

* * * * *

SEQUENCE LISTING

```
<160> NUMBER OF SEQ ID NOS: 4

<210> SEQ ID NO 1
<211> LENGTH: 1705
<212> TYPE: DNA
<213> ORGANISM: Rhodomonas

<400> SEQUENCE: 1
cggaaacctt gttacgactt ctccttcctc taaatgataa ggttcaatca acttctcgca       60
accaaagcac gtgaatgcaa aggtcagcaa tccgaagatt tcaccggacc attcaatcgg      120
```

```
taggagcgac gggcggtgtg tacaaagggc agggacgtaa tcaacgcgag ctgatgactc      180
gcgcttacta ggaattcctc gttgaagatt aataattgca ataatctayc cccatcacga      240
tgaattttca caagtttacc crattctttc gaataaggga ggagctcgtt gcattcatca      300
gtgtagcgcg cgtgcggccc agaacatcta agggcatcac agacctgtta ttgcctcaaa      360
cttccattca ttaaacacaa atagtccctc taagaagtgg gccacatatc aaagatatgc      420
gtcactagtt agcaggctga ggtctcgttc gttaacggaa ttaaccagac aaatcactcc      480
accaactaag aacggccatg caccaccacc catagaatca agaaagagct ttcaatctgt      540
caatccttac tatgtctgga cctggtaagt ttccccgtgt tgagtcaaat taagccgcag      600
gctccactcc tggtggtgcc cttcgtcaa ttcctttaag tttcagcctt gcgaccatac       660
tcccccggga acccaaaaac tttgattcct cacaaggtgc caatggagtc gcaaattgac      720
atccactgat ccctagtcgg catagtttat ggttaagact acgacggtat ctgatcgtct      780
tcgatcccct aactttcgtt cttgatcaat gaaaacatcc ttgccgaatg ctttcgcaga      840
agtttatctt tcgtaaatcc aagaatttca cctctgacaa cgaaatataa acggccccaa      900
ctgtccctgt taatcattac ttcggtccca taaaccaaca aataagacca aagtcctatt      960
ccattattcc atgctaatgt attcaagcgt aggcctgctt tgaacactct aatttttca      1020 aagtaaacgg cctgcgtccc actaccctac agttaagtag aataggatcc ccaggcagaa     1080
aggcccggac atgccgtccg accaaggcc gacagcctcc ccgagcccga catccgacta      1140
cgagcttttt aactgcaaca actttaatat acgctattag agctggaatt accgcggctg     1200
ctggcaccag acttgccctc taattgatcc tcgtaaaggg attaaattg ttctcattcc      1260 aataacaaga ctgtaagccc tgtattgtta tttattgtca ctacctcccc gagtcgggat     1320
tgggtaattt gcgcgcctgc tgccttcctt ggatgtggta gccgtctctc aggctccctc     1380
tccggaatcg aaccctaatt ctccgtcacc cgttaaaacc atggtaggcc tctatcctac     1440
catcgaaagt tgatagggca gaaatttgaa tgaatcacca ccaccgcgag ggctgtggtt     1500
cgagaagtta ttatgaatca ccagaaatgt ggcttggaat ctaataaata cagtccttcg     1560
taagtcggac ctttgtgcat gtattagctc tagaattact acgttatcc atgtagtaag     1620 ggaccatcaa ataaacgata actgatttaa tgagccattc gcagtttcat aacgttattt      1680
acactaagac atgcatggct taatc                                           1705

<210> SEQ ID NO 2
<211> LENGTH: 1822
<212> TYPE: DNA
<213> ORGANISM: Rhodomonas

<400> SEQUENCE: 2
cggaaacctt gttacgactt ctccttcctc tagatgataa ggctcagtga acttcttgaa       60
aattcctaac gcgaacgcgc tgggttttc aatccgatca tttcaccgga ccatccaatc       120
ggtaggagcg acgggcggtg tgtacaaagg gcagggacgt attcagcgcg agttaatgac      180
tcacgcttac aaggcattcc tcgttcaaga tgaataattg caatcatcta tccctagcac      240
gatgcagctt cgaagattcc ccagaccttt cggtcaagga gcagcactcg ttggttgcat      300
cattgtagcg cgcgtgcggc ccagaacatc taagggcatc acagacctgt tattgcctca      360
tccttccatc cgctagccgc ggatcgtccc tctaagaagc ctactctcag cgctgccgcc      420
aagacggcta tttagcaggt taaggtctcg ttcgttaacg gaattaacca gacaaatcac      480
```

```
tccaccaact aagaacggcc atgcaccacc acccatagaa tcaagaaaga gctctcaatc      540
tgtcaatcct tcctatgtcc ggacctggta aggtttcccg tgttgagtca aattaagccg      600
caggctccac gcctggtggt gcccttccgt caattccttt aagtttcagc cttgcgacca      660 tactccccc agaacccata gactttgatt tctcataggg tgctgataga gtcgttttg       720 gtacatctac caatccccag tcggcatagt ttatggttaa gactacgacg gtatctaatc     780
gtcttcgatc ccttaacttt cgttcttgat caatgaaaac atccttggca gatgctttcg     840
cagttgttcg tcttccgtaa atccaagaat ttcacctctg acaacggagt acgagtgccc     900
ccaactatcc ctattaatca ttacttcggc tccaaaaacc aacaaatag aaccggaagt      960 cctattctat tattccatgc tgaggtatct aagccttcca aaggcctgcc atgaacactc    1020
tattttattc acagtaaaaa atgtcgcccc gctggctgtt caattaagaa cagaccttgt    1080
ggcgacaaga ctgggcccga cacgctaaaa gcttttaag actattccgc aggccgggcc     1140
cgaattcgac tacgagcttt ttaactgcaa caactttagt atacgctatt ggagctggaa    1200
ttaccgcggc tgctggcacc agacttgccc tccaatggat cctcgagaag gggtgtaaat    1260
tatcctcatt ccaatgaaca gactcgatcg agccgccat cgttatttct tgtcgctacc     1320
tccctgagtc aggattgggt aatttacgcg cctgctgcct tccttggatg tggtagccat    1380
ttctcaggct ccctctccgg aatcgaaccc taattctccg tcaccgtca acaccatggt     1440 aggccactac cctaccatcg aaagttgata gggcagaaat ttgaatgatt taccgccggc    1500
caaaattaga aagccatgcg attttgggaag ttatcatgat tcatcccgcc acgccctcac   1560
gaaggaggac gattggtttt tgatctaata aatcccgttg cttttcttct ggtatccttc    1620
agatgagctt ctttattttt tttttaaaa gaaatccatc tgaaggatac cggagaaaca    1680
acgatggggc atgtattagc tctagaattc ctacggttat ccacgtagcg ccgcacgatc    1740
aaataaacta taactgttgt aatgagccat tcgcagtttc acggtacaaa atcgttcgta    1800
ctgagacatg catggcttaa tc                                             1822
```

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
cagtagtcat atgcttgtct taag                                              24

<210> SEQ ID NO 4
<211> LENGTH: 27
<212> TYPE: DNA
<213> ORGANISM: Artificial Sequence
<220> FEATURE:
<223> OTHER INFORMATION: primer

<400> SEQUENCE: 4
agcttgatcc ttctgcaggt tcaccta                                           27